US008202981B2

(12) United States Patent
McKay et al.

(10) Patent No.: US 8,202,981 B2
(45) Date of Patent: Jun. 19, 2012

(54) COMPOSITIONS AND THEIR USES DIRECTED TO PTPRU

(75) Inventors: Robert McKay, Poway, CA (US); Ravi Jain, Fremont, CA (US); Kenneth W. Dobie, Del Mar, CA (US); Sanjay K. Pandey, Encinitas, CA (US); Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/009,626

(22) Filed: Jan. 19, 2011

(65) Prior Publication Data
US 2011/0112171 A1 May 12, 2011

Related U.S. Application Data

(62) Division of application No. 11/915,309, filed as application No. PCT/US2006/020388 on May 24, 2006, now Pat. No. 7,897,583.

(60) Provisional application No. 60/684,398, filed on May 24, 2005.

(51) Int. Cl.
*C07H 21/04* (2006.01)
*C07H 21/02* (2006.01)
*A61K 48/00* (2006.01)
(52) U.S. Cl. .................. 536/24.5; 536/23.1; 536/24.31; 536/24.33; 514/44
(58) Field of Classification Search .................... None
See application file for complete search history.

(56) References Cited

U.S. PATENT DOCUMENTS

| | | | |
|---|---|---|---|
| 5,705,623 A * | 1/1998 | Wiggins et al. | ............. 536/23.2 |
| 5,801,154 A | 9/1998 | Baracchini et al. | |
| 6,277,640 B1 | 8/2001 | Bennett et al. | |
| 6,582,908 B2 | 6/2003 | Fodor et al. | |
| 2001/0053519 A1 | 12/2001 | Fodor et al. | |
| 2003/0228597 A1 | 12/2003 | Cowsert et al. | |
| 2005/0019915 A1 | 1/2005 | Bennett et al. | |

FOREIGN PATENT DOCUMENTS

| | | |
|---|---|---|
| WO | WO 93/24510 | 12/1993 |
| WO | WO 94/26764 | 11/1994 |
| WO | WO 2004/094636 | 11/2004 |
| WO | WO 2005/026735 | 3/2005 |

OTHER PUBLICATIONS

Aguiar et al., "PTPROt: An Alternatively Spliced and Developmentally Regulated B-Lymphoid Phosphatase That Promoted G0/G1 Arrest" Blood (1999) 94:2403-2413.
Amoui et al., "Expression of a Structurally Unique Osteoclastic Protein-tyrosine Phosphatase Is Driven by an Alternative Intronic Cell Type-specific Promoter" J. Biol. Chem. (2003) 278:44273-44280.
Avraham et al., "Characterization and chromosomal localization of PTPRO, a novel receptor protein tyrosine phosphatase, expressed in hematopoietic stem cells" Gene (1997) 204:5-16.
Beltran et al., "Expression of PTPRO during mouse development suggests involvement in axonogenesis and differentiation of NT-3 and NGF-dependent neurons" J. Comp. Neurol. (2003) 456:384-395.
Branch et al., "A good antisense molecule is hard to find" TIBS (1998) 23:45-50.
Chin, "On the preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crossland et al., "Molecular cloning and characterization of PTPπ, a novel receptor-like protein-tyrosine phosphatase" Biochem. J. (1996) 319(Pt 1):249-254.
Czauderna et al., "Structural variations and stabilising modifications of synthetic siRNAs in mammalian cells" Nucleic Acids Research (2003) 31(11):2705-2716.
Gait et al., "Applications of Chemically Synthesized RNA" RNA: Protein Interactions, Ed. Smith (1998) 1-36.
Gallo et al., "2'-C-Methyluridine phosphopramidite: a new building block for the preparation of RNA analogues in " Tetrahedron (2001) 57:5707-5713.
McArdle et al., "Protein Tyrosine Phosphatase Genes Downregulated in Melanoma" J. Invest. Dermatol. (2001) 177:1255-1260.
Mori et al., "Identification of Genes Uniquely Involved in Frequent Microsatellite Instability Colon Carcinogenesis by Expression Profiling Combined with Epigenetic Scanning" Cancer Res. (2004) 64:2434-2438.
Motiwala et al., "Suppression of the protein tyrosine phosphatase receptor type O gene (PTPRO) by methylation in hepatocellular carcinomas" Oncogene (2003) 22:6319-6331.
New England Biolabs 1998/1999 Catalog, cover page, pp. 121 and 284.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.

(Continued)

*Primary Examiner* — Amy Bowman
(74) *Attorney, Agent, or Firm* — Knobbe, Martens, Olson & Bear LLP

(57) ABSTRACT

Disclosed herein are compounds, compositions and methods for modulating the expression of PTPRU in a cell, tissue or animal. Also provided are methods of active target segment validation. Also provided are uses of disclosed compounds and compositions in the manufacture of a medicament for treatment of diseases and disorders. Also provided are methods for the prevention, amelioration and/or treatment of diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease by administration of antisense compounds targeted to PTPRU.

22 Claims, No Drawings

OTHER PUBLICATIONS

Scaringe, "RNA Oligonucleotide Synthesis via 5'-Silyl-2'-Orthoester Chemistry" Methods (2001) 23:206-217.

Stepanek et al., "CRYP-2/cPTPRO is a neurite inhibitory repulsive guidance cue for retinal neurons in vitro" J. Cell. Biol. (2001) 154:867-878.

Suhr et al., "Antisense oligodeoxynucleotide evidence that a unique osteoclastic protein-tyrosine phosphatase is essential for osteoclastic resorption" Journal of Bone and Mineral Research (2001) 16(10):1795-1803.

Taniguchi et al., "The Receptor Protein Tyrosine Phosphatase, PTP-RO, Is Upregulated During Megakaryocyte Differentiation and Is Associated With the c-Kit Receptor" Blood (1999) 94:539-549.

Thomas et al., "GLEPP1, a Renal Glomerular Epithelial Cell (Podocyte) Membrane Protein-tyrosine Phosphatase" J. Biol. Chem. (1994) 269:19953-19962.

Wang et al., "Molecular Cloning and Characterization of a Novel Human Receptor Protein Tyrosine Phosphatase Gene, hPTP-K: Down-Regulation of Gene Expression by PMA and Calcium Ionophore in Jukrat T Lymphoma Cells" Biochem. Biophys. Res. Commun. (1997) 231:77-81.

Wang et al., "Transcriptional regulation of a receptor protein tyrosine phosphatase gene hPTP-J by PKC-mediated signaling pathways in Jurkat and Molt-4 T lymphoma cells" Biochem. Biophys. Acta. (1999) 1450:331-340.

Wang et al., "Characterization of PCP-2, a novel receptor protein tyrosine phosphatase of the MAM domain family." Oncogene (1996) 12:2555-2562.

Wharram et al., "Altered podocyte structure in GLEPP1 (Ptpro)-deficient mice aswsociated with hypertension and low glomerular filtration rate" J. Clin. Invest. (2000) 106:1281-1290.

Yan et al., "Physical and Functional Interaction between Receptor-like Protein Tyrosine Phosphatase PCP-2 and B-Catenin" Biochemistry (2002) 41:15854-15860.

Zhang, "Protein-Tyrosine Phosphatases: Biological Function, Structural Characteristics, and Mechanism of Catalysis" Crit. Rev. Biochem. Mol. (1998) 33:1-52.

European Search Report for application EP 06771266.1 dated Oct. 6, 2010.

International Search Report from PCT/US06/20388 dated Jan. 3, 2007.

* cited by examiner

SEQUENCE LISTING

<160> NUMBER OF SEQ ID NOS: 258

<210> SEQ ID NO 1
<211> LENGTH: 5637
<212> TYPE: DNA
<213> ORGANISM: H. Sapiens

<400> SEQUENCE: 1

| | | | | | |
|---|---|---|---|---|---|
| aattccgggc | gccagtcccg | ctccgcgccg | cgccgctccg | ctccggctcg | ggctccggct | 60 |
| cgcctcgggc | tgggctcggg | ctccggggc | ggcgtcccg | ccgccgggcc | ccgggacggg | 120 |
| cggcgacgct | ccaaccatgg | cccgtgccca | ggcgctcgtg | ctggcactca | ccttccagct | 180 |
| ctgcgcgccg | gagaccgaga | ctccggcagc | tggctgcacc | ttcgaggagg | caagtgaccc | 240 |
| agcagtgccc | tgcgagtaca | gccaggccca | gtacgatgac | ttccagtggg | agcaagtgcg | 300 |
| aatccaccct | ggcacccggg | cacctgcgga | cctgccccac | ggctcctact | tgatggtcaa | 360 |
| cacttcccag | catgccccag | gccagcgagc | ccatgtcatc | ttccagagcc | tgagcgagaa | 420 |
| tgatacccac | tgtgtgcagt | tcagctactt | cctgtacagc | cgggacgggc | acaggccggg | 480 |
| caccctgggc | gtctacgtgc | gcgttaatgg | gggcccctg | ggcagtgctg | tgtggaatat | 540 |
| gactggatcc | cacggccgtc | agtggcacca | ggctgagctg | gctgtcagca | ctttctggcc | 600 |
| caatgaatat | caggtgctgt | ttgaggccct | catctcccca | gaccgcaggg | gctacatggg | 660 |
| cctagatgac | atcctgcttc | tcagctaccc | ctgcgcaaag | gccccacact | tctcccgcct | 720 |
| gggcgacgtg | gaggtcaacg | cgggccagaa | cgcgtcgttc | cagtgcatgg | ccgcgggcag | 780 |
| agcggccatg | cgccaacgct | tcctcttgca | acggcagagc | ggggccctgg | tgccggcggc | 840 |
| gggcgttcgg | cacatcagcc | accggcgctt | cctggccact | ttcccgctgg | ctgccgtgag | 900 |
| ccgcgccgag | caggacctgt | accgctgtgt | gtcccaggcc | ccgcgcggcg | cgggcgtctc | 960 |
| taacttcgcg | gagctcatcg | tcaaggagcc | cccaactccc | atcgcgcccc | cacagctgct | 1020 |
| gcgtgctggc | cccacctacc | tcatcatcca | gctcaacacc | aactccatca | ttggcgacgg | 1080 |
| gccgatcgtg | cgcaaggaga | ttgagtaccg | catggcgcgc | gggccctggg | ctgaggtgca | 1140 |
| cgccgtcagc | ctgcagacct | acaagctgtg | gcacctcgac | cccgacacag | agtatgagat | 1200 |
| cagcgtgctg | ctcacgcgtc | ccggagacgg | cggcactggc | cgccctgggc | cacccctcat | 1260 |
| cagccgcacc | aaaatgcgcag | agcccatgag | ggccccccaaa | ggcctggctt | ttgctgagat | 1320 |
| ccaggcccgt | cagctgaccc | tgcagtggga | accactgggc | tacaacgtga | cgcgttgcca | 1380 |
| cacctatact | gtgtcgctgt | gctatcacta | caccctgggc | agcagccaca | accagaccat | 1440 |
| ccgagagtgt | gtgaagacag | agcaaggtgt | cagccgctac | accatcaaga | acctgctgcc | 1500 |
| ctatcggaac | gttcacgtga | ggcttgtcct | cactaaccct | gagggcgca | aagagggcaa | 1560 |
| ggaggtcact | ttccagacgg | atgaggatgt | gcccagtggg | attgcagccg | agtccctgac | 1620 |
| cttcactcca | ctggaggaca | tgatcttcct | caagtgggag | gagccccagg | agcccaatgg | 1680 |
| tctcatcacc | cagtatgaga | tcagctacca | gagcatcgag | tcatcagacc | cggcagtgaa | 1740 |
| cgtgccaggc | ccacgacgta | ccatctccaa | gctccgcaat | gagacctacc | atgtcttctc | 1800 |
| caacctgcac | ccaggcacca | cctacctgtt | ctccgtgcgg | gccgcacag | gcaaaggctt | 1860 |
| cggccaggcg | gcactcactg | agataaccac | taacatctct | gctcccagct | ttgattatgc | 1920 |
| cgacatgccg | tcaccctgg | gcgagtctga | gaacaccatc | accgtgctgc | tgaggccggc | 1980 |
| acagggccgc | ggtgcgccca | tcagtgtgta | ccaggtgatt | gtggaggagg | agcgggcgcg | 2040 |

```
gaggctgcgg cgggagcgag gtggacagga ctgcttccca gtgccattga ccttcgaggc    2100
ggcgctggcc cgaggcctgg tgcactactt cggggccgaa ctggcggcca gcagtctacc    2160
tgaggccatg cccttttaccg tgggtgacaa ccagacctac cgaggcttct ggaacccacc    2220
acttgagcct aggaaggcct atctcatcta cttccaggca gcaagccacc tgaagggggga   2280
gacccggctg aattgcatcc gcattgccag gaaagctgcc tgcaaggaaa gcaagcggcc    2340
cctgaggtg tcccagagat cggaggagat ggggcttatc ctgggcatct gtgcaggggg     2400
gcttgctgtc ctcatccttc tcctgggtgc catcattgtc atcatccgca agggagaga    2460
ccactatgcc tactcctact acccgaagcc ggtgaacatg accaaggcca ccgtcaacta    2520
ccgccaggag aagacacaca tgatgagcgc cgtggaccgc agcttcacag accagagcac    2580
cctgcaggag gacgagcggc tgggcctgtc cttcatggac acccatggct acagcacccg    2640
gggagaccag cgcagcggtg gggtcactga ggccagcagc ctcctggggg gctccccgag    2700
gcgtccctgt ggccggaagg gctcccccata ccacacgggg cagctgcacc ctgcggtgcg   2760
tgtcgcagac cttctgcagc acatcaacca gatgaagacg gccgagggtt acggcttcaa    2820
gcaggagtat gagagcttct ttgaaggctg gacgccaca aagaagaaag acaaggtcaa    2880
gggcagccgg caggagccaa tgcctgccta tgatcggcac cgagtgaaac tgcacccgat    2940
gctgggagac cccaatgccg actacattaa tgccaactac atagatggtt accacaggtc    3000
aaaccacttc atagccactc aagggccgaa gcctgagatg gtctatgact tctggcgtat    3060
ggtgtggcag gagcactgtt ccagcatcgt catgatcacc aagctggtcg aggtgggcag    3120
ggtgaaatgc tcacggtact ggccggagga ctcagacacc tacggggaca tcaagattat    3180
gctggtgaag acagagaccc tggctgagta tgtcgtgcgc acttttgccc tggagcggag    3240
aggctactct gcccggcacg aggtccgcca gttccacttc acagcgtggc cagagcatgg    3300
cgtcccctac catgccacgg ggctgctggc tttcatccgg cgcgtgaagg cctccacccc    3360
acctgatgcc gggcccattg tcatccactg cagcgcgggc accggccgca cagggttgcta   3420
tatcgtcctg gatgtgatgc tggacatggc agagtgtgag ggcgtcgtgg acatttacaa    3480
ctgtgtgaag actctctgct cccggcgtgt caacatgatc cagactgagg agcagtacat    3540
cttcattcat gatgcaatcc tggaggcctg cctgtgtggg gagaccacca tccctgtcag    3600
tgagttcaag gccacctaca aggagatgat ccgcattgat cctcagagta attcctccca    3660
gctgcgggaa gagttccaga cgctgaactc ggtcacccg ccgctggacg tggaggagtg     3720
cagcatcgcc ctgttgcccc ggaaccgcga caagaaccgc agcatggacg tcctgccgcc    3780
cgaccgctgc ctgcccttcc tcatctccac tgatggggac tccaacaact acattaatgc    3840
agccctgact gacagctaca cacgagtgc ggccttcatc gtgaccctgc acccgctgca     3900
gagcaccacg cccgacttct ggcggctggt ctacgattac gggtgcacct ccatcgtcat    3960
gctcaaccag ctgaaccagt ccaactccg ctggccctgc ctgcagtact ggccagagcc     4020
aggccggcag caatatggcc tcatggaggt ggagtttatg tcgggcacag ctgatgaaga    4080
cttagtggct cgagtcttcc gggtgcagaa catctctcgg ttgcaggagg gcacctgct    4140
ggtgcggcac ttccagttcc tgcgctggtc tgcataccgg gacacacctg actccaagaa    4200
ggccttcttg cacctgctgg ctgaggtgga caagtggcag gccgagagtg gggatgggcg    4260
caccatcgtg cactgcctaa acgggggagg acgcagcggc accttctgcg cctgcgccac    4320
ggtcctggag atgatccgct gccacaactt ggtggacgtt ttctttgctg ccaaaaccct    4380
ccggaactac aaacccaaca tggtggagac catggatcag taccactttt gctacgatgt    4440
```

-continued

```
ggccctggag tacttggagg ggctggagtc aagatagcgg ggccctggcc tggggcaccc    4500
actgcacact cagggccaga cccaccatcc tggactggcg aggaagatca gtgcctcctg    4560
ctctgcccaa acacactccc atggggcaag cactggagtg gatgctgggc tatcttgctc    4620 cccccttccac tgtgggcagg gcctttcgct tgtcccatgg gcgggtggtg ggccaaggag    4680
gagcttagca agtctgcagc ccagccccac ctccataggg tcctgcaggc ctgtgctgag    4740
aggcctggtg ctgcctggca gagtgacaaa ggctcaggac ggctggctct ggggactca     4800 ggccaagccc cttggcacca tcctggcttt tggcagggat gagtgaggcc ctgcagagag    4860
catcccaggc caaggttccc actcagcctg cccctctgc atgtgggtag aggatgtact     4920
gggacttggc atttaggatt ccatctggcc cagcccctga aggtcctggg gaagcaggtc    4980
tcaattctga atagccagtg gggcacactg actgtcctcc caggggaac tgcagcgccc      5040 tcctccccac tgcccctgc agccctgag atattttgct cactatccct ccccacttgc       5100
ttccctgata tgtgctctga gcttccctga accaggatct gcctattact gctgtgcccc    5160 atgggggct ccttccctgc ctgacccact gttgcagaat gaagtcacct cgccccctc       5220 ttcctttaat cttcaggcct cactggcctg tcctgctcag cttgggccag tgacaatctg    5280
caaggctgaa caacagcccc tggggttgag gccctgtgg ctcctggtca ggctgcccgt     5340
tgtggggagg ggcagtgtta gagcagggct ggtcataccc tctggagttc agaggaagag    5400
gtaggaccag tgcttttttg tttcttttgt tattttggt tgggtgggtg ggaaggtctc     5460
tttaaaatgg ggcaggccac acccccattc cgtgcctcaa tttccccatc tgtaaactgt   5520
agatatgact actgacctac ctcgcagggg gctgtgggga ggcataagct gatgtttgta    5580
aagcgctttg taaataaacg tgctctctga atgccaaaaa aaaaaaaaaa aaaaaaa       5637
```

<210> SEQ ID NO 2
<211> LENGTH: 5618
<212> TYPE: DNA
<213> ORGANISM: H. Sapiens

<400> SEQUENCE: 2

```
aattccgggc gccagtcccg ctccgcgccg cgccgctccg ctccggctcg ggctccggct      60
cgcctcgggc tgggctcggg ctccggggc ggcgtccccg ccgcgggcc ccgggacggg       120 cggcgacgct ccaaccatgg cccgtgccca ggcgctcgtg ctggcactca ccttccagct    180
ctgcgcgccg gagaccgaga ctccggcagc tggctgcacc ttcgaggagg caagtgaccc     240
ctgcgcgccg gagaccgaga ctccggcagc tggctgcacc ttcgaggagg caagtgaccc     240
agcagtgccc tgcgagtaca gccaggccca gtacgatgac ttccagtggg agcaagtgcg    300
aatccaccct ggcacccggg cacctgcgga cctgccccac ggctcctact tgatggtcaa    360
cacttcccag catgccccag gccagcgagc ccatgtcatc ttccagagcc tgagcgagaa    420
tgatacccac tgtgtgcagt tcagctactt cctgtacagc cgggacgggc acagcccggg    480
cacccctggg gtctacgtgc gcgttaatgg gggcccctg ggcagtgctg tgtggaatat     540
gactggatcc cacggccgtc agtggcacca ggctgagctg gctgtcagca ctttctggcc    600
caatgaatat caggtgctgt ttgaggccct catctcccca gaccgcaggg gctacatggg    660
cctagatgac atcctgcttc tcagctaccc ctgcgcaaag gccccacact ctcccgcct    720 gggcgacgtg gaggtcaacg cgggccagaa gcgtcgttc cagtgcatgg ccgcgggcag    780
agcggccgag gccgaacgct tcctcttgca acggcagagc ggggcgctgg tgccggcggc    840
gggcgtgcgg cacatcagcc accggcgctt cctggccact ttcccgctgg ctgccgtgag    900
ccgcgccgag caggacctgt accgctgtgt gtcccaggcc ccgcgcggcg cgggcgtctc    960
```

-continued

```
taacttcgcg gagctcatcg tcaaggagcc cccaactccc atcgcgcccc cacagctgct    1020
gcgtgctggc cccacctacc tcatcatcca gctcaacacc aactccatca ttggcgacgg    1080
gccgatcgtg cgcaaggaga ttgagtaccg catggcgcgc gggccctggg ctgaggtgca    1140
cgccgtcagc ctgcagacct acaagctgtg gcacctcgac cccgacacag agtatgagat    1200
cagcgtgctg ctcacgcgtc ccggagacgg cggcactggc cgccctgggc cacccctcat    1260
cagccgcacc aaatgcgcag agcccatgag gccccccaaa ggcctggctt ttgctgagat    1320
ccaggcccgt cagctgaccc tgcagtggga accactgggc tacaacgtga cgcgttgcca    1380
cacctatact gtgtcgctgt gctatcacta cccctgggc agcagccaca accagaccat    1440
ccgagagtgt gtgaagacag agcaaggtgt cagccgctac accatcaaga acctgctgcc    1500
ctatcggaac gttcacgtga ggcttgtcct cactaaccct gaggggcgca agagggcaa    1560
ggaggtcact ttccagacgg atgaggatgt gcccagtggg attgcagccg agtccctgac    1620
cttcactcca ctggaggaca tgatcttcct caagtgggag gagccccagg agcccaatgg    1680
tctcatcacc cagtatgaga tcagctacca gagcatcgag tcatcagacc cggcagtgaa    1740
cgtgccaggc ccacgacgta ccatctccaa gctccgcaat gagacctacc atgtcttctc    1800
caacctgcac ccaggcacca cctacctgtt ctccgtgcgg gcccgcacag gcaaaggctt    1860
cggccaggcg gcactcactg agataaccac taacatctct gctcccagct ttgattatgc    1920
cgacatgccg tcaccctgg gcgagtctga aacaccatc accgtgctgc tgaggccggc    1980
acagggccgc ggtgcgccca tcagtgtgta ccaggtgatt gtggaggagg agcgggcgcg    2040
gaggctgcgg cgggagccag gtggacagga ctgcttccca gtgccattga ccttcgaggc    2100
ggcgctggcc cgaggcctgg tgcactactt cggggccgaa ctggcggcca gcagtctacc    2160
tgaggccatg ccctttaccg tgggtgacaa ccagacctac cgaggcttct ggaacccacc    2220
acttgagcct aggaaggcct atctcatcta cttccaggca gcaagccacc tgaaggggga    2280
gacccggctg aattgcatcc gcattgccag gaaagctgcc tgcaaggaaa gcaagcggcc    2340
cctggaggtg tcccagagat cggaggagat ggggcttatc ctgggcatct gtgcaggggg    2400
gcttgctgtc ctcatccttc tcctgggtgc catcattgtc atcatccgca aagggaagcc    2460
ggtgaacatg accaaggcca ccgtcaacta ccgccaggag aagacacaca tgatgagcgc    2520
cgtggaccgc agcttcacag accagagcac cctgcaggag gacgagcggc tgggcctgtc    2580
cttcatggac acccatggct acagcacccg gggagaccag cgcagcggtg gggtcactga    2640
ggccagcagc ctcctggggg gctccccgag gcgtccctgt ggccggaagg ctccccata    2700
ccacacgggg cagctgcacc ctgcggtgcg tgtcgcagac cttctgcagc acatcaacca    2760
gatgaagacg gccgagggtt acggcttcaa gcaggagtac gagagcttct ttgaaggctg    2820
ggacgccaca aagaagaaag acaaggtcaa gggcagccgg caggagccaa tgcctgccta    2880
tgatcggcac cgagtgaaac tgcacccgat gctgggagac cccaatgccg actacattaa    2940
tgccaactac atagatattc ggataaaccg agaaggttac cacaggtcaa accacttcat    3000
agccactcaa gggccgaagc ctgagatggt ctatgacttc tggcgtatgg tgtggcagga    3060
gcactgttcc agcatcgtca tgatcaccaa gctggtcgag gtgggcaggg tgaaatgctc    3120
acggtactgg ccgaggagact cagacaccta cgggacatc aagattatgc tggtgaagac    3180
agagaccctg gctgagtatg tcgtgcgcac ttttgccctg gagcggagag ctactctgc    3240
ccggcacgag gtccgccagt tccacttcac agcgtggcca gagcatggcg tccctacca    3300
tgccacgggg ctgctggctt tcatccggcg cgtgaaggcc tccacccac ctgatgccgg    3360
```

```
gcccattgtc atccactgca gcgcgggcac cggccgcaca ggttgctata tcgtcctgga   3420
tgtgatgctg acatggcag agtgtgaggg cgtcgtggac atttacaact gtgtgaagac   3480
tctctgctcc cggcgtgtca acatgatcca gactgaggag cagtacatct tcattcatga   3540
tgcaatcctg gaggcctgcc tgtgtgggga ccaccatc cctgtcagtg agttcaaggc   3600
cacctacaag gagatgatcc gcattgatcc tcagagtaat tcctcccagc tgcgggaaga   3660
gttccagacg ctgaactcgg tcaccccgcc gctggacgtg gaggagtgca gcatcgccct   3720
gttgccccgg aaccgcgaca gaaccgcag catggacgtc ctgccgcccg accgctgcct   3780
gcccttcctc atctccactg atggggactc caacaactac attaatgcag ccctgactga   3840
cagctacaca cggagtgcgg ccttcatcgt gaccctgcac ccgctgcaga gcaccacgcc   3900
cgacttctgg cggctggtct acgattacgg gtgcacctcc atcgtcatgc tcaaccagct   3960
gaaccagtcc aactccgcct ggccctgcct gcagtactgg ccagagccag gccggcagca   4020
atatggcctc atggaggtgg agtttatgtc gggcacagct gatgaagact tagtggctcg   4080
agtcttccgg gtgcagaaca tctctcggga ggggcacctg ctggtgcggc acttccagtt   4140
cctgcgctgg tctgcatacc gggacacacc tgactccaag aaggccttct tgcacctgct   4200
ggctgaggtg gacaagtggc aggccgagag tggggatggg cgcaccatcg tgcactgcct   4260
aaacggggga ggacgcagcg gcaccttctg cgcctgcgcc acggtcctgg agatgatccg   4320
ctgccacaac ttggtggacg ttttctttgc tgccaaaacc ctccggaact acaaacccaa   4380
catggtggag accatggatc agtaccactt ttgctacgat gtgggcctgg agtacttgga   4440
ggggctggag tcaagatagc ggggccctgg cctggggcac ccactgcaca ctcagggcca   4500
gacccaccat cctggactgg cgaggaagat cagtgcctcc tgctctgccc aaacacactc   4560
ccatgggca agcactggag tggatgctgg gctatcttgc tccccttcc actgtgggca   4620
gggcctttcg cttgtcccat gggcgggtgg tgggccaagg aggagcttag caagtctgca   4680
gcccagcccc acctccatag ggtcctgcag gcctgtgctg agaggcctgg tgctgcctgg   4740
cagagtgaca aaggctcagg acggctggct ctggggact caggccaagc ccttggcac   4800
catcctggct tttggcaggg atgagtgagg ccctgcagag agcatcccag gccaaggttc   4860
ccactcagcc tgccccctct gcatgtgggt agaggatgta ctgggacttg gcatttagga   4920
ttccatctgg cccagcccct gaaggtcctg gggaagcagg tctcaattct gaatagccag   4980
tggggcacac tgactgtcct cccagggga actgcagcgc cctcctcccc actgcccct   5040
gcagcccctg agatattttg ctcactatcc ctccccactt gcttccctga tatgtgctct   5100
gagcttccct gaaccaggat ctgcctatta tgctgtgcc ccatgggggg ctccttccct   5160
gcctgaccca ctgttgcaga atgaagtcac ctcgccccc tcttcctta atcttcaggc   5220
ctcactggcc tgtcctgctc agcttgggcc agtgacaatc tgcaaggctg aacaacagcc   5280
cctggggttg aggcccctgt gctcctggtc aggctgcccg ttgtggggag gggcagtgtt   5340
agagcagggc tggtcatacc ctctggagtt cagaggaaga ggtaggacca gtgctttttt   5400
gtttcttttg ttattttgg gtgggtgggt gggaaggtct ctttaaaatg gggcaggcca   5460
cacccccatt ccgtgcctca atttccccat ctgtaaactg tagatatgac tactgaccta   5520
cctcgcaggg ggctgtgggg aggcataagc tgatgtttgt aaagcgcttt gtaaataaac   5580
gtgctctctg aatgccaaaa aaaaaaaaa aaaaaaa                             5618
```

<210> SEQ ID NO 3
<211> LENGTH: 5607
<212> TYPE: DNA

<213> ORGANISM: H. Sapiens

<400> SEQUENCE: 3

```
aattccgggc gccagtcccg ctccgcgccg cgccgctccg ctccggctcg ggctccggct      60
cgcctcgggc tgggctcggg ctccggggggc ggcgtccccg ccgccgggcc ccgggacggg     120
cggcgacgct ccaaccatgg cccgtgccca ggcgctcgtg ctggcactca ccttccagct     180
ctgcgcgccg gagaccgaga ctccggcagc tggctgcacc ttcgaggagg caagtgaccc     240
agcagtgccc tgcgagtaca gccaggccca gtacgatgac ttccagtggg agcaagtgcg     300
aatccaccct ggcacccggg cacctgcgga cctgccccac ggctcctact tgatggtcaa     360
cacttcccag catgccccag gccagcgagc ccatgtcatc ttccagagcc tgagcgagaa     420
tgataccac tgtgtgcagt tcagctactt cctgtacagc cggacgggc acaggccggg      480
caccctgggc gtctacgtgc gcgttaatgg gggcccctg ggcagtgctg tgtggaatat      540
gactggatcc cacggccgtc agtggcacca ggctgagctg gctgtcagca ctttctggcc     600
caatgaatat caggtgctgt ttgaggccct catctcccca accgcaggg gctacatggg      660
cctagatgac atcctgcttc tcagctaccc ctgcgcaaag gccccacact tctcccgcct     720
gggcgacgtg gaggtcaacg cgggccagaa cgcgtcgttc cagtgcatgg ccgcgggcag     780
agcggccatg cgccaacgct tcctcttgca acggcagagc ggggcccctg gtgccggcggc     840
gggcgttcgg cacatcagcc accggcgctt cctggccact ttcccgctgg ctgccgtgag     900
ccgcgccgag caggacctgt accgctgtgt gtcccaggcc ccgcgcggcg cgggcgtctc     960
taacttcgcg gagctcatcg tcaaggagcc cccaactccc atcgcgcccc cacagctgct    1020
gcgtgctggc cccacctacc tcatcatcca gctcaacacc aactccatca ttggcgacgg    1080
gccgatcgtg cgcaaggaga ttgagtaccg catggcgcgc gggccctggg ctgaggtgca    1140
cgccgtcagc ctgcagacct acaagctgtg gcacctcgac cccgacacag agtatgagat    1200
cagcgtgctg ctcacgcgtc ccggagacgg cggcactggc cgcctgggc caccctcat     1260
cagccgcacc aaatgcgcag agcccatgag ggccccaaa ggcctggctt ttgctgagat     1320
ccaggcccgt cagctgaccc tgcagtggga accactgggc tacaacgtga cgcgttgcca    1380
cacctatact gtgtcgctgt gctatcacta caccctgggc agcagccaca accagaccat    1440
ccgagagtgt gtgaagacag agcaaggtgt cagccgctac accatcaaga acctgctgcc    1500
ctatcggaac gttcacgtga ggcttgtcct cactaacct gaggggcgca agagggcaa      1560
ggaggtcact ttccagacgg atgaggatgt gcccagtggg attgcagccg agtccctgac    1620
cttcactcca ctggaggaca tgatcttcct caagtgggag gagccccagg agcccaatgg    1680
tctcatcacc cagtatgaga tcagctacca gagcatcgag tcatcagacc cggcagtgaa    1740
cgtgccaggc ccacgacgta ccatctccaa gctccgcaat gagacctacc atgtcttctc    1800
caacctgcac ccaggcacca cctacctgtt tccgtgcgg gccgcacag gcaaaggctt      1860
cggccaggcg gcactcactg agataaccac taacatctct gctcccagct ttgattatgc    1920
cgacatgccg tcacccctgg gcgagtctga aacaccatc accgtgctgc tgaggccggc    1980
acagggccgc ggtgcgccca tcagtgtgta ccaggtgatt gtggaggagg agcgggcgcg    2040
gaggctgcgg cgggagcgag gtggacagga ctgcttccca gtgccattga ccttcgaggc    2100
ggcgctggcc cgaggcctgg tgcactactt cggggccgaa ctggcggcca gcagtctacc    2160
tgaggccatg ccctttaccg tgggtgacaa ccagacctac cgaggcttct ggaacccacc    2220
acttgagcct aggaaggcct atctcatcta cttccaggca gcaagccacc tgaaggggga    2280
```

```
gacccggctg aattgcatcc gcattgccag gaaagctgcc tgcaaggaaa gcaagcggcc    2340
cctggaggtg tcccagagat cggaggagat ggggcttatc ctgggcatct gtgcaggggg    2400
gcttgctgtc ctcatccttc tcctgggtgc catcattgtc atcatccgca agggaagcc     2460
ggtgaacatg accaaggcca ccgtcaacta ccgccaggag aagacacaca tgatgagcgc    2520
cgtggaccgc agcttcacag accagagcac cctgcaggag gacgagcggc tgggcctgtc    2580
cttcatggac acccatggct acagcacccg gggagaccag cgcagcggtg gggtcactga    2640
ggccagcagc ctcctggggg gctccccgag gcgtccctgt ggccggaagg gctccccata    2700
ccacacgggg cagctgcacc ctgcggtgcg tgtcgcagac cttctgcagc acatcaacca    2760
gatgaagacg gccgagggtt acggcttcaa gcaggagtat gagagcttct ttgaaggctg    2820
ggacgccaca aagaagaaag acaaggtcaa gggcagccgg caggagccaa tgcctgccta    2880
tgatcggcac cgagtgaaac tgcacccgat gctgggagac cccaatgccg actacattaa    2940
tgccaactac atagatggtt accacaggtc aaaccacttc atagccactc aagggccgaa    3000
gcctgagatg gtctatgact tctggcgtat ggtgtggcag gagcactgtt ccagcatcgt    3060
catgatcacc aagctggtcg aggtgggcag ggtgaaatgc tcacggtact ggccggagga    3120
ctcagacacc tacggggaca tcaagattat gctggtgaag acagagaccc tggctgagta    3180
tgtcgtgcgc acttttgccc tggagcgagg aggctactct gcccggcacg aggtccgcca    3240
gttccacttc acagcgtggc cagagcatgg cgtcccctac catgccacgg ggctgctggc    3300
tttcatccgg cgcgtgaagg cctccacccc acctgatgcc gggcccattg tcatccactg    3360
cagcgcgggc accggccgca caggttgcta tatcgtcctg gatgtgatgc tggacatggc    3420
agagtgtgag ggcgtcgtgg acatttacaa ctgtgtgaag actctctgct cccggcgtgt    3480
caacatgatc cagactgagg agcagtacat cttcattcat gatgcaatcc tggaggcctg    3540
cctgtgtggg gagaccacca tccctgtcag tgagttcaag gccacctaca aggagatgat    3600
ccgcattgat cctcagagta attcctccca gctgcgggaa gagttccaga cgctgaactc    3660
ggtcaccccg ccgctggacg tggaggagtg cagcatcgcc ctgttgcccc ggaaccgcga    3720
caagaaccgc agcatggacg tcctgccgcc cgaccgctgc ctgcccttcc tcatctccac    3780
tgatggggac tccaacaact acattaatgc agccctgact gacagctaca cacggagtgc    3840
ggccttcatc gtgaccctgc acccgctgca gagcaccacg cccgacttct ggcggctggt    3900
ctacgattac gggtgcacct ccatcgtcat gctcaaccag ctgaaccagt ccaactccgc    3960
ctggccctgc ctgcagtact ggccagagcc aggccggcag caatatggcc tcatggaggt    4020
ggagtttatg tcgggcacag ctgatgaaga cttagtggct cgagtcttcc gggtgcagaa    4080
catctctcgg ttgcaggagg ggcacctgct ggtgcgcaca ttccagttcc tgcgctggtc    4140
tgcataccgg gacacacctg actccaagaa ggccttcttg cacctgctgg ctgaggtgga    4200
caagtggcag gccgagagtg gggatgggcg caccatcgtg cactgcctaa cgggggagg     4260
acgcagcggc accttctgcg cctgcgccac ggtcctggag atgatccgct gccacaactt    4320
ggtggacgtt ttctttgctg ccaaaaccct ccggaactac aaacccaaca tggtggagac    4380
catggatcag taccactttt gctacgatgt ggccctggag tacttggagg gctggagtc     4440
aagatagcgg ggccctggcc tggggcaccc actgcacact cagggccaga cccaccatcc    4500
tggactggcg aggaagatca gtgcctcctg ctctgcccaa acacactccc atggggcaag    4560
cactggagtg gatgctgggc tatcttgctc ccccttccac tgtgggcagg gcctttcgct    4620
tgtcccatgg gcgggtggtg ggccaaggag gagcttagca agtctgcagc ccagccccac    4680
```

-continued

| | |
|---|---|
| ctccataggg tcctgcaggc ctgtgctgag aggcctggtg ctgcctggca gagtgacaaa | 4740 |
| ggctcaggac ggctggctct gggggactca ggccaagccc cttggcacca tcctggcttt | 4800 |
| tggcagggat gagtgaggcc ctgcagagag catcccaggc caaggttccc actcagcctg | 4860 |
| cccctctgc atgtgggtag aggatgtact gggacttggc atttaggatt ccatctggcc | 4920 |
| cagcccctga aggtcctggg gaagcaggtc tcaattctga atagccagtg gggcacactg | 4980 |
| actgtcctcc ccaggggaac tgcagcgccc tcctccccac tgcccctgc agcccctgag | 5040 |
| atattttgct cactatccct ccccacttgc ttccctgata tgtgctctga gcttccctga | 5100 |
| accaggatct gcctattact gctgtgcccc atggggggct ccttccctgc ctgacccact | 5160 |
| gttgcagaat gaagtcacct cgccccctc ttcctttaat cttcaggcct cactggcctg | 5220 |
| tcctgctcag cttgggccag tgacaatctg caaggctgaa caacagcccc tggggttgag | 5280 |
| gcccctgtgg ctcctggtca ggctgcccgt tgtggggagg ggcagtgtta gagcagggct | 5340 |
| ggtcataccc tctggagttc agaggaagag gtaggaccag tgctttttg tttcttttgt | 5400 |
| tattttggt tgggtgggtg ggaaggtctc tttaaaatgg ggcaggccac accccattc | 5460 |
| cgtgcctcaa tttccccatc tgtaaactgt agatatgact actgacctac ctcgcagggg | 5520 |
| gctgtgggga ggcataagct gatgtttgta aagcgctttg taaataaacg tgctctctga | 5580 |
| atgccaaaaa aaaaaaaaaa aaaaaaa | 5607 |

<210> SEQ ID NO 4
<211> LENGTH: 91089
<212> TYPE: DNA
<213> ORGANISM: H. Sapiens

<400> SEQUENCE: 4

| | |
|---|---|
| ccgctcttgg ccaggtgatg agcgccctgt tcctggaggt atgtagaaca cgcatttgaa | 60 |
| ggcgccaagg tacaagggat tcaggcatcg gatgggacag aggccgggtg tccctgggtc | 120 |
| accgtccctg agagcgctgt acgggagcta ggcgtgggcc atgagcgtgc tcgcctggca | 180 |
| gtgttggtgc ccggtccgtg gagacgtccg tgggcgtcca gacccagccg cggggcctca | 240 |
| tggcggggag gatgcgggag cggggaggg gcgcgccagg gctagcgggc ggccggaccc | 300 |
| gctgcagcac ccgccgtggc cagcaggag cgccgcgaga ccgccgaacc gcggccgggg | 360 |
| cctgacgtca gcgccccgct tgctccggct cgcgctctgg actcggcgcc agtcccgctc | 420 |
| cgcgccgcgc cgctccgctc cggctcgggc tccggctcgc ctcgggctgg gctcgggctc | 480 |
| cggggcggc gtccccgcg ccgggccccg ggacgggcgg cgacgctcca accatggccc | 540 |
| gtgcccaggc gctcgtgctg gcactcacct tccagctctg cgcgccggag accgagactc | 600 |
| cggcaggtaa gcgcgcggcg gccggaccga gcctgccccg ccgagcctcg gggcccgtgg | 660 |
| cgtagctcgg aagaaagtgt gagtgttgag tgaccgggcg ttacgagcgt gctccctgtg | 720 |
| tgtgtctgag cgtaggatgg gcgattgtgt gcccggggtt ttgcgtgact gcgaatgttg | 780 |
| tgtgtccgtg agttctgtgc gcaagaaaag gtgatgtgtg tcggcgagta tgttgggggt | 840 |
| gaatgttgtg tgcatcgagg cattgggtgt gcgctgagtg tcttgtgggt ctgccagtgt | 900 |
| gtagtgtttg tgtggccaag tgggttgtgt gtgcatctga gtttggttgt gttgcgggag | 960 |
| ttgtatctgc taatgtgttg catttgtttg cattttgtat gcctggccgg gagtgctgtt | 1020 |
| tgttttgtgt ctgcgagtgg gttgtgtgtt tgtgttatgc ctgtggccaa gggtgctctc | 1080 |
| tggatcccgc ctgagtgtgg atccgggaac gcgtgtgtgg cgtgtgtgct tttgagatcc | 1140 |
| gtgtacatgt gtgaaggcgt gggaacgggt ccggaacgtg tgtgtccgtg cgctgtgtac | 1200 |

-continued

```
gtgtggggag tgtctagggt atgtggtgtg tgctgccggg ggccgcgtgg gtccgagtga    1260
atgccaagtg tgccgggaat gcgtgtgtgg gagcgagtct ggaacggatg tgagtgtgtg    1320
cgaatgtgtc cgtgtgtgct ggctgcgcgt ccaggaatgt tgcgagtgtg gagcgcgcct    1380
gggccgcggt tgcgagtgtg ccctggtccc ggggccgccc gaggggggcgg tggcaggacg    1440
tgtgtgcgcg cgtgtgcgtg tgcgcgtgtg tggcgcgctg ggccggaaca agttgtcgcg    1500
gcggcgcccc ctgggctgcc cgggtcgggc agggcccgag gctcagggga ggaccgggcc    1560
ccgcggccgc cgcctcgggc atgtcggact gtttgttgtt tcgcaagttc cgcgcggcgc    1620
tggcgggcgg ctgatccgag gcggcgccgg ggctgcgggg cgcccgggcc agcgggcccc    1680
agcgaggggc cggcgggcgg gcaggggagg gccggaccgg cgggcgctcc tgcggtggcc    1740
gggccgcggc tgcgccccgg gcggccggcc ggggctgtc cccgggctgg gctgcgacgt    1800
ccgggcgcgg gcagggcctg gctcgccgcc ggggacggc gcccctccc ttggcgcgca    1860
ggacgcgcgc gggacgcccg ggcctccgg gacactccct tggtggagcc tgcaactttg    1920
tgcggcctcc cggccggccg ggaccgccag gtgtgtgctt gagtgtgagc gtgagtgtga    1980
gcgtgtggct ccgcgcttgt ctgctgtgtg gtcgcgttct ccgggtgtgt tcggagtct    2040
ggtgtctttg gtgtgcgtgc gcgtgtgtgt gtgcgcgcag ctgaatgtat gtatacggag    2100
cctgtgtttg tgtgtccgtg tgctcgtcgg agtgtggacg gtgtgtcgga tgtgtgtgcg    2160
tgcgcgtgtt ccacatccca ccctgaggcc tgggatccta daccgcggcc ccttcccgcg    2220
gagtttcggg gccctgctcc gggtgacctc ccccgccctc gccaccggcg gggctgctcc    2280
gcgggctccg ggtagccggg agacgcccgg ggcgggatcc gagccgagac acgtgctgga    2340
gcggagccgc ttcctcacgg tcgccagccg cagacaactg acctccccgg catcgcgttc    2400
gcggccctgc tgctggctcc ggtgtctcgg gccggaactc ctgtggctcc agcgttcgcg    2460
ccggccactg gccagcgctt gggcctcgcc ctgcagctcc ggggccatag gcacagctt    2520
tagctttgac ctccccgttc ccgaaaggac gcccaaggcg acctcccacc ccatcctccc    2580
caacttctcc cccatgtcct gcggcaactt tgcctccctc tcccaccgtg aaatcaaacc    2640
cgcggggttc tgtatgcgcc ccatcccccgc tcctaccacc atcgctttga tttcaagaac    2700
actcacaagc cccaagccct gccagcagga ggactgtcag gaactgaagt ttgggagtga    2760
ggcctagagc aggttactcc cattcttgat gcctcagttt cctcttctgc ctcatagcca    2820
tcatgataat ggtgtatggc acttttggta gataccaagt accttgtaaa gtaaggctct    2880
gtctgtgagt gccagggaac aaaaaatgga tttgagagtt gttgcaaagc cccagacaga    2940
ggctgtgatt taaagctggg gtattaggtg tcaaattctg cctctgctac ttgctattca    3000
tgtgatgtct ggcaaatcac ctcacttgta aagttcctgg cccccttgt tattcttaga    3060
gatgaactca gaagcccaag tagaatagat gtgataccc ttgtccccag tctggacaga    3120
gtcagcccag ctccctgaat ggctccgag cttccgggta ggggcggtgt gtgatgcctt    3180
ctcagccttg caaacctggt agttatttat tctgctgtgt tcttgctatt ttgtcctttt    3240
ggtcgcagga gttgtggacg gcaggaatga gggagtggct gcccagtggt ttcaggttgg    3300
gcaataaagg cttgtctggg catccctccc tttttccctgg ggctagggga ggggacttag    3360
caggaagcag tgacagtggc cgaggtgggg acgctgagct cctggacagc tgctgccca    3420
gctctggtgt cagaaaaaac ctagggcaag catcgtgctt gatggagaca ggccaccatc    3480
cttccatgat tttcatcagc tcagctgggc atatggggtg cctttccat gcaggactgg    3540
gttggccaga gttgcagggg gtaccttgtg ctcctccttc ctccccctcc cccttttcc    3600
```

```
tagttgccct cctgcatcct ggaacgtcct gtctgccctc tcagagactc tttcatctgt    3660
ctccttctgt ccgtcctcag ctatctttca cctgcaggaa gactccagcc tcctccttcc    3720
ctctttccct catggtgcca gggatctttg taaagtacat tttaactcaa agggtttaaa    3780 acccttgaa ggctccccat tgccttcagg gtgaagtcct tatcccttgg ccctgttgct    3840
ggctctagct cctgcctgcc tgtccagctg catcttgttt tgtgtcactg ccccttgcat    3900
cctatgatct ggccagcctg accttcttac caaagaccca aatgcccaca gcctgctgtc    3960
tcctctctgg gcctttgggc aagccgtgct ttctctgcag aactttctaa ctccagcttt    4020
ttgctggtga actcctgcaa cttgatgggc tctcagctgt aagcatcatc cagtccctga    4080
agccttcctc ggtgatgccc tgtcctagcc taggaagtcg gggggtgggg gtcaattgga    4140
tttttacata gcattgtaat tattgtaatt acagtttatt agtgctgtct cccttaccag    4200
actgagagct gaggacagag actgggtttt tagtttactt ctgaatctta gtgccaggta    4260
caaggcctgg cccaccgggt ctgaataaat atatatggcc tgaaagaata aagtttaagg    4320
gggccaggtt cagaggtgga gatgccagat gggggtgcac tgattccact gaaggtagag    4380
attgaagaac caggtttccc tccaggaatc tggaaaattc ctggagggtg gggatggtg    4440 ttatgttgtg aaaaggccat gttgagagtg tcatctggga gctttgagtt ggggaggttg    4500
agtccctggc aagagactga agggaacggg cctcctgcct gccagcccct cccccaggct    4560
ctggccccac ccctagcagc tggcagggcc cttccagccc ccagtctcag gcttttgtga    4620
tggggcctgg cagttggtga gacgttgagt ctcaacggtc tgtgtgagtg gctggggagg    4680
agggagggag cccgcagggc cctgtgttag gagagggagg gaagcttcct ggaagaccct    4740
cccttagtcc tcagtcctag atcctagggt gggcgggtgg ggtcacagcc tctgttctca    4800
ccgcttgtgc accggaggga agggaggaga actgcatccc gtggtggccc tggcagatgg    4860
ggttggggag gctggctgag gtgtgtgcag atgtgactct agcatctggg cagtcagagt    4920 gggggtgtg tagggattgt aactaggggc atggacacat gtgacctgtt agggtgtcta    4980
gccatctggt tatcgtgtgg tgtggcagga tctgagtttg gagtagggag gtaaccagct    5040
gctttgaccc ctggggagcc tggtgctaag ggtgtctggc tatccaagta tcacattcct    5100
ggagttgggt gcagagctat ttggatgggt ggtgtctcgc tatctaggtg tggacaaccc    5160
agtaccagca tgtgggagga tcagggtgtg cagacagagg ctatcccagc atccctgggg    5220
ctggaggtgg gtgtatccat gtgtctggga gtcctcaggt tagtgggtat ttataagtgg    5280
ggagtgtctc tgtgttgtgt ccaggtatgg ggctggccag gtgcctgagt gtctggttgt    5340
aggggtcccc aagtgtccgg gtatctgagg gtgggggtat ctgtgtatga acaacaggg    5400 acccagtcat tgaagtatcc agttgttagt gagtctgggt gtggggtgcc atgtgtctat    5460
tttttttttt tcttcttctt cttcttcttc ttctttttttt tgagatggag tctcactctg    5520
tcacccaggc tggagtgcag tggcgtgatc ttggctcatt gcaacctccg cctcccgggt    5580
tcaagtgatt ctcctgcctc agcctcctaa gtagctggga ttacaggcgc acgccaccat    5640
gcctggctaa ttttttgtatt tttagtagag actgggtttc gtcatgttgg tcaggctggt    5700
cttgaactcc tgacattgtg atctgcctgc cttggccttc caaagtgctg agattacagg    5760
cgtgaaccac agcgcacggc cttttcttct ttttattca gatggagtct cgctttgtca    5820
cccaggctgg agtgcaatgg catgatctcg gctcactgca acctttgcct cctgggttca    5880
agcgattctc ctgcctcagc ctcccgaata gctgggatta caggcacccg ccaccatgcc    5940
tggctaattt ttgtattttt agtagagatg gggtttcacc atgttggcca ggctggtctt    6000
```

```
gaactcctga cctcaggtga tccacctgct tcggcctccc aaagtgttgg gattacaggt    6060
gtgagccact gtgcctggcc tcatgtgtct atttgtatgt ttagatgtgg aggtgccctt    6120
gtgacctatg gtggtgtcca tgtatccagg atgtgtccac aaggggtgtg acgtgttgg     6180 gtgggaatgt cctggtggct gtacccaact caacctctgg tagcccttc cctgggactt     6240 gcctcctgat cgctcttcag actccaaagc cagaagcctt ggaaggggcc ccgatagttc    6300 tgttttcaa cggtcagcct agagctgtgt tatctaatag aaccttctgt ggtgatggaa     6360
attgtcctct acctgcattc tccaatacgg tggctcctga gtcatgtatg ggtattacat    6420
ttaaattaat taaaataaaa attcaatccc tcagttgcac tagtcagatt tcaagtcctc    6480
aagagtcata tgttgctagt ggctctcatt gtactggtta atgcaggcag agaacatttc    6540
catcctctca gaaagttctg cagacagcac tggtctagag gcatgaggcg gcctgcagca    6600
ccttcagtga gtcctgggca tctctgggag gggaattggt ctggatggac catgactcag    6660
tggctcttga caaaggtttt tgttcaatcc aggcccttc tctgcagcct tattagatct     6720
tgcctggact attgcagtag cctggtagcc ttcttggcct ctactctgcc tgccatcacg    6780
ctctcggttt ctttttttttt ttttgagatg gagtctcact ctgtcaccca ggctggagtg    6840
caggggcacc atcttggctc actgcaacct ctgcctcctg ggttcaagca attcttcagc    6900
ctcagcctcc caagtagctg ggactacagg cgcgtgccac cacgctcggc taattttttg    6960
tatttttaat aaagacgggg tttcactgtg ttagccagga tggtctccat ctcctgacct    7020
catgacctgc ctgactcggc ctcccaaagt actgggatta gaggcatgag ccccgggcc     7080 cggcccaggc ttttggtttc taatgcttcc accaccctgt ggctggaata agcttctaag    7140
gcagacatag gatgctgcca ctcctttgtc ccaagctgaa ggctccccag aactcagggg    7200
acaaacccca aaccctagca tagcacatga ggccctgcat gaccagccct tctttctga     7260 agcagcttca catgatgcct ttcttccctg atcccactcc tgcctatccg ctgtctgctc    7320
caaatcacca ggcaaattgc tgatccagga gcctgccatg ccagttcaca cctctctacc    7380
tttgcacaca ctgtgcccct ccctacttct cacctcgtgg tggggtggg ggatctacct     7440 acttgttcag ccttcacagt tcagctccat tgtcactgat gcagcgaagc cttcccagcc    7500
ctctcccggt gcagttggtg aaatttctcc catagtggac gtctgacaat gtgctgcggt    7560
tttccatctc cttttttccac taggctggga gcccccaggg gctgagctgt gtctttgtca    7620
tctgtggtcc ccagggccta tacgtgggag atgcccacta agtggctgca tctcgatgcc    7680
tctgggtgca cagggaaggc ttggaggggt gaatgcagga gctgggttc tgcagcacag     7740 tcatgggtgg gctggctatg cctcctcctc tggctctggg ttggggggctg ccatttcctg    7800 cagaatgact gtgggaggac ccctgagggg gacagctcag aagatgctgc ttccagatga    7860
cgcaggaggt cttgggcaga ttcccaagat gcaaaccaca agaccttgtg atgactcaga    7920
agggacaagg agaagggggg cttggagggc cgctgaggct tggagttttg agggcagaag    7980
ctggggagaa agattgagat ggggctgtta ggaagggggag atgctgagga tatttgacag    8040
ggcaagatta aagctagggg tggggtgaca gctcagcccc cggggctcc cagactagtg      8100 gaaaaaggag acggaaaacc gcagcacact gtcagatgtc cactgtggtg ggtgacagct    8160
gaggcctggg ggaccactgg cggatagaag atagctggtg ggaaagatat acctggggga    8220
tgggacagct gacagtgaag ggacaggcgg tattggggga acaactgagg gttggggac     8280 aggtggatga tagaacaagg agatgtgggt gataagataa gaggtggaga taagaggtga    8340
caactgggag ctatcagaaa cctagtggat aggacaggtg agtctcagct gagagtggga    8400
```

-continued

| | |
|---|---|
| aatacattgc ttagaatgtg tatgtatgtg tgtttacagg agcgtgcatg tggacttgtg | 8460 |
| gctgggcatg cctgtcaata tgtgtttgtc tagcgtgtgg tggttaagag catgggttca | 8520 |
| gggcccagac catctgggtt ctaatcctaa gcccaccact tctagctgtg tgatactttg | 8580 |
| gtaagttact gacctctctg ggcccttaga gttctcattt gtggaatggg gataataata | 8640 |
| ggacacactg catgcgtttg tcatgaggat atgttttatg gttatgatta tgtaggttag | 8700 |
| aacaggtcct gcacatagta agcactgtgt aagtgatcac tgttatgatg tgtgtatttg | 8760 |
| catgcgtgcg gtcatcctgt gtgcccagaa aagtttgttc ttggtttctg atgaagtcca | 8820 |
| ggcctgggag ggagtaatag tggtggggac ggggtggtg gttggggagt gcctagccag | 8880 |
| gttgattgag tctggctctt ctctgacatc ctaacctctt gttcatccta cttcctgctc | 8940 |
| accctgtccc agggccttat ccaataatag gtctttctct ctatctctcc tctgtcctgc | 9000 |
| cctgggctgg gggccagggg ctgtacttta attgtctgag agctttacca gcagaatttg | 9060 |
| aattcattgt tttcctgcca gcatgctggg attctgctca gttataatac ctggacaatg | 9120 |
| tgctcgattc tagatggcct atcctgtggg tggcagtggc ttcagccttt gcccttggag | 9180 |
| agtcactggg gtgaagatg ttggaggag ggagacaagc cagatgagat tcggccccc | 9240 |
| aacttgtggg gtgagccagc gtggccgggc agagctgtag gtagagagtt ttccagggat | 9300 |
| ctgagctccc ctctcctcca gtgcatcaca gggaggcatc atgaccctcc cagcaacact | 9360 |
| gttgcagcgt gccaggctct ggactgctct ggatgtgcac tgtctgggat tcctgggtcc | 9420 |
| agcctccttg cacagccctg tgtctcagcc ctctacttca ctgggattgc tgcattgcat | 9480 |
| tgagggtgtg cgttctcctg agtttctgca tgctctgcct ctgcattgtc ccattggacc | 9540 |
| gtgcctccat cctgccatga tcctgccatg gtcctgccat gtgtgtgtct ttgctgctct | 9600 |
| cttgtatact gtgtcactct gctggatgtc agtgttgcat tgggaaggtg aattctcctg | 9660 |
| ggtttctggg cggagctgct cacactgcac cactgtctga gatcaacaca tggttttctg | 9720 |
| tggccacatt gcatgtttgt gtcatagagc atttatattc tgcaccccat tgcctcacca | 9780 |
| ggcagtctac attgcattgg gcacatggac tcttttgggg tttgggcata gctcctcgca | 9840 |
| ttgcagcact gcaccgtgcc aacagatggc atgctaccac aacattgcat cttggcatca | 9900 |
| cacagcatct ctgtactgca ctgcactatt gcatggacgt cagtattgca tcaggactgt | 9960 |
| gaacttttcc tgagtttctg ggcatggccc tctgcattc cacagttgca ttgtaccaac | 10020 |
| agtgcacttt gccccatata gcacttctgt gcatgtgcac tgctttgctg cactggatat | 10080 |
| gtgcctcatg gcccagccct tgcactgcac cactgctgct gaaacgctgc ccctatggtg | 10140 |
| tcctggcctt tcacgctcct accaccatgg tatctgtagg ctggcgtcct tttccaggtt | 10200 |
| tttgttgtca gccctacgtg aacaacatct ttgcattgag tgtcctcact gccccacgtt | 10260 |
| gcacatgact cagggagtct atatctatag tacagcttgg gaccactttc ttgggcttca | 10320 |
| ggactggctt aggtttgcaa aggcagcacc actgcacagt atctgacatt gcattcgtgc | 10380 |
| actgcacagg attactgccc agggcctcta ccctgcaacg aacctgttca ctgttgggtt | 10440 |
| gtgtgcactc taccggattg cgggaccag agccttgcg ttgaatccac tggttccaca | 10500 |
| cagcatctat ttttttttt ttaagatgga atctcactct gttggccagg ctggagtgca | 10560 |
| atggagcggt ctgggctcac tgccacctcc gcccctggg ttcaagtgat tctcctgcct | 10620 |
| ccgcctcctg agtagctggg attacaggca tgtgccacca aacccagcta attttgtat | 10680 |
| ttttactgga gacgaggttt caccatgttg gccaggctgg tctcaaacct ctgacctcaa | 10740 |
| atgatccacc tgcctcggcc tctcaaagtg ctgggattac gggcatgagc tactgcgccc | 10800 |

| | |
|---|---|
| agctccacac agcatcttaa ttgtactcca ttttgtgcca cttcctaccc atgcctcgag | 10860 |
| tctgcacata ctctgttcct caggactgta tttattgggc ttatatgcta ggctgggttg | 10920 |
| ccgcaccctg cagtttcttc ttcactcact gccccttcc catcccctta tctctctgtt | 10980 |
| gttctgtgtg cctgtgctgc atgtctatgc agggcacaca cccttcccct gagaatgcat | 11040 |
| gaagcttgaa ctagtaaggc ttaaacttac catcttggca ttcctccata cacctatcac | 11100 |
| gtagcactgg gtgccagccc agtgtaccac taaatgcact gcagtggcgc ggtgtgcctt | 11160 |
| gtgcagctct gggtcatgcc catgatggat gtggcacttc catggtgcat catggccctg | 11220 |
| gccagttctg ccatgctgta ccagatgtct gtaatgaggc ctgtgcacac tgtgggctct | 11280 |
| gctccctgca ttgtataaca gtattctgtc tctacactgc aaagctgctg tactgcaccc | 11340 |
| tccacacact gcactgtggc acagcagagg cctctctcca tggacccttta tgaagtacag | 11400 |
| atcgtcacac tgctcgggtt tgtgcacagc cccatgcccc tctactctat actctgtctt | 11460 |
| cgtatgtcgc agggtgtctg tggggcagat ctgtgaactc tttgcaccac tgcaccactg | 11520 |
| cacaacatag tcctccattc ggccctttc ctctgtctgg catccagccc tggcctgtgc | 11580 |
| cttcccctca tactgccagt gtggcagctc tactgctaac tctgggattt gcagcacata | 11640 |
| ttgatcaggg agatggggag tgggcctggc ataaggtccc ctgctgtact tggtttcctt | 11700 |
| ccattctccg tggagatggc aagatgttgg cattgtcagg ctgtgtgttg gctctgtggg | 11760 |
| tggtgctagc tcaactttcc ctgtggccca gccctgggcg atctttctgg ttgcagctat | 11820 |
| ggtgactcct gggtgattag aaaatgggca tactgctccc agccctgact acaattaatg | 11880 |
| acccatcagt ttgtcagggc tcttcgggca gctctggag cctcagctta ggtctagatg | 11940 |
| agttgacttg ggcaaggaga gtagcaaggt gggctgggcc gggcctctgg gctggagtca | 12000 |
| tggtcctaga gctgggtgtg gttggtgagg gtcagactag ctgggatcat ggggtcaata | 12060 |
| agtccaggca ctgttggcta tacacagggc ttgggatggg gttcaaatgc atgagacgtg | 12120 |
| gtccttgacc tcaggcaggg aggaggtagg gattagacag gcctgagatg gagctgtagc | 12180 |
| tggggtggag aacccaggat ggggctgggt taggcaagaa agtcagggt gagtccagtg | 12240 |
| ttggttccag gcttgggctg ggctgctgag aatagggta caaccttgga tgatgaaata | 12300 |
| gtccagtatt gttgttgggg ttgtatttga attcccccac ccacaactgg gcatgtacct | 12360 |
| gggcttgggt gaaatcccag cccctaaatg tgcaacctgt tgggaaaagt tttgcttctc | 12420 |
| ctgggaccac tcttgggaat tggatgttct attgacaaac caagggcag aaaagtctca | 12480 |
| ttgcaaacag gctctgtttg ccaggtgtct tcagaaaata ctggttgcag ctgcagccgc | 12540 |
| attgggcatg gagtgctgtt ccctgtctgg tgtgaggaaa gtctggtgca cagtgcttgt | 12600 |
| gttcacactg acacatacac gtatgcacaa ctcccatcta ccttactgca cacacccacc | 12660 |
| tcccccttag gtgcaggctt accactaaat atgccctgta cctttgcttg taaatgcacg | 12720 |
| tctatacacc cacggcttca cagcgcctgc ccgggagacc tcccctttcc gacacccatg | 12780 |
| cccaccctca tgcacctctg cccccaagatg actcttgctc acgtgcacac tcacgcaact | 12840 |
| gcaaccggtc atctgacctt agcggtcccc actctcattt tacaggtgag gaggtaagga | 12900 |
| ttcagagagg gcaagtcacc tgcccaaagt cacaaaggga cttagaggct cagtgggaaa | 12960 |
| aagatcccgg tcttccgcct cccatttgaa tacttgaaac tcagtaccag gctgtcctgt | 13020 |
| catcttagag ccatgagtgc acgtgtgcac acacacacac gcacacctgc acacactcac | 13080 |
| acgcacacct gcatgtggac acatgcatgg ggaggtgtgg agcccctccc accagggaga | 13140 |
| cccctcccac actcctccag aggcagctct gccccttaca tcaccccatc ctgagcccag | 13200 |

```
ccggatgtgg ctaaaccatc ccctgcctt cccaaattgt ggctgacggt tgctcaggca    13260
accgcctgcc agactgggga gattagctga ggaatgtagc tgggccagtt tgaactgagg    13320
ctgggggagc ccttgggggt cttgggttga ttcaattcac cctctcaggg aggcctctgt    13380
agagatgggg tgcccaaggg caggcattct ccctgttccc agtctgaggc tgcatcccca    13440
ggcttggccc aggctgcaga aagggagtgt gtgtgaacac tgagcgcggg gctcagggca    13500
tatgtgtgtt gtgtgctgtg cacctctctg agtgtgattg gagggtgtgc cgtttacatc    13560
ctggaagggg acttgaggcc cctgtcctca ccagtttctg acatctgact ctggacccct    13620
tggtggcttg gtcccaagat ccctctggat cctgctgtgc tctctggaga caccacctgc    13680
cctactcatg gcttatagga tatatcattt atctcatctg aatccaggat gagataaact    13740
ttcctactca aacacctact gtggcttctc aattcaaaat gaggcccagc tcctcaccct    13800
ggcgttcagg gtcctccatg attggcctca acctcccttc cctccagtca tagctcccat    13860
ggctttagcc aacctgggct cctttctgtg ccctggacaa actgtgttta ttgaccacct    13920
tgctttgctc ccctgggtct tttgccacaa atccttccac ccatctctac ctatccttct    13980
tggctctgct tagatgccgc ctcttccagg aggcctttcc cctctacctg gcccctccc     14040 ctggaccccc tcttgtggcc ttgactcttc ccttattccc tcattccctc ttcctcaccc    14100
tcactgggac taggaggtcc ctgagggcag ggcagagtct tcatcatcct tgtacctcta    14160
atagtgccag cctgggacct gctttgtact ggcagggaaa atcccctgt gaatgaagct     14220 gaattaacac ttatggccag cagaagggca ggctttgttt tgtttgtgcc cagtctcctg    14280
gaataaagat aggaggttta agtctgagct tctgcacatt gtagctgcat ggccttgagt    14340
aagcagctgt atctctctga gcctgtttta atctgtaaat taggaataat aatagtacct    14400
aataaactaa caataagaca aaaataatac tacctacctt ctgagttgct gaggattcac    14460
cggctcaggt ggtcatggtg gtaattcaca gccccttcat agaggtattg atgtgtatat    14520
gtgcatgtct gtgcccatgt ctgtgttgat ggagtcaaga aggattcctt gctaccattc    14580
ttgctctgaa ctcaaagtcg gatttagtgg cctccagcag gagttgagtc tctagcagag    14640
ctgggacttg gctttggggc ttttggctcc tagctgacca ttcccatctc aagggaccag    14700 gggaagggt gagggtgggg ctctccttag ggagcctgtc cccagagatg ttacccacta     14760
tgagctggag ctagaactgg gtctggccca gagacacagg tctagagacg gacatgggtc    14820
agggagaggg agtgaatctg gttaaggaat cactctgagg ctgggtacag tggctcatgc    14880
ctgtaatccc agcactttgg gaggccaagg tggaggcacc acttgaggcc agaagtttga    14940
gaccagcctg gccagcatgg tgacatcccc atctctacta aaaatacaaa aacaagctgg    15000
gtatggtggc acgtgcctat aattccagct actttgcagg ctgaggcacg agaatagctt    15060
gaacctggga gctggaggtt gcagtgagcg agatcatgct actgcacttc agcctgggca    15120
acagaatgag actctatctc aaaagaaaaa aaaaaagga atcactctgg atgcggtcag    15180
tcagtcagcc catccagagt gactccttgg aggtcacctt ggccggggtc agttgtaggg    15240
gtcatttggc agaggtcagg ggtcactgtg gctgggtgt gcaggtctgg ggtcagtcag     15300
tctgatggtt attctggccg aagtgagata gtctgggggt catctgtatg aggcagaggc    15360
cactttcaac agggacagtc agctgggagc caggctggct gaggtcggcc tatttggggg    15420
tcaccaactt ggatcagtct ggctggggat cataggactg ttgtcagtct atctggggc     15480 tcctgtgact gaggtcaggt ggtctgggtg tcactctgac caggttagtc agtctgggag    15540
tcctggccgt tcgtgtggcc tggctcagga tgaacaagag gaagccaagg ggctggcact    15600
```

```
cccaggctct ccccagggtg gtgagtgaga catcagggca gcggctttgt tacttgtgaa    15660
ggaacaggaa aggcctgaac cccatccagg gctttagatc ctgggcttcc ctttctggca    15720
acccctctac ctcaaggagg ccttggctaa gagccttagg gcaggcccag ctcaagctga    15780
agtcagctgg cctcctcctc caggaagtcc tccctgacca ccatgctctc tctctgtact    15840
tgccatgttc tttctctctg ctgcactgtg ggtcttttc tacaggggaa gctgaggccc      15900
tccaggtaca gatggggtta atacccacct cctacaggca atagggtatg atgctgacca    15960
gggattttca aacaaagagc caaagagctc agccaaggtc ctgcctcagc tctggaaaga    16020
gtcttctgtt acttcatccc aactgcttgg tgccatcctc acacccacat ctcaccattt    16080
caggagaaga ccgggagccc ccagcagtga ggagccctt tgtgcctggc tcttctgggt     16140
gtgtttttct ttttcttc tttttttttt ttttgagaca gagtcacact ctgtcaccct       16200
ggctggagtg cagggtacc atctcagctc actgcaacct ctgcctgctg ggttcaagtg      16260
attcttctat ttctgcctcc caagtagctg gactatagg catgcgccac cacacccagc      16320
taatttttta attttagta gagatggggt ttcatcatgt tggccaggct ggtcttgaac      16380
tcctgacctc aggcgatctg cctgcctcgg cctcccaaag tgttgggatt acaggtgtga    16440
gccaccgcgc ctggcctggg tgtgttttc atgtgctact tcacatcatc cgcatcaccg     16500
cctagaggag ttgcagctgc agatgaaaca gtagagcctc ctaaaagtga agtcgcttgc    16560
tgcgtgtgaa gatgcctagc actgggcctg tgacatagca ctcactcccc aggtgctgtt    16620
gtttgggaaa agctctctca aacggtgttt ttcctctgcc ctcccaccac cacagcagca    16680
gtcatcaaca caggaggcct ctgtgaccaa atgtgtgggg gcttctcccc accaccaagc    16740
aagcaattaa ttctgtagca gacaccaggt gggtgtcctc caattcagtt ctagcacaag    16800
agtcagatcc catgggttga gggctcagtc cccatgactg cctcctcctc cagacaccag    16860
tcgcaagtct gggcctccag aacttctggc cgacccgctg caggttgggg ttcccacgac    16920
cccctctttg agtttgatta atttgctgga gcagctcaca gaactcaggg aaacacatta    16980
actggttaat tataaaggat attgcaaagg atacagatga agagatgcat agggtgaggt    17040
atgggagaag ggacatggag cttccttgcc ctttctggac ccaccatcct ccaagaagct    17100
ccatgtgttc agctgtctgg aagctctccg aaccctgtcc ttttgggtat ttacggaggt    17160
ttccttacat aagcatgatg gacaaatgtg attgcacata aaacacctga tctaaaccca    17220
gcaaggcctg tctgcttaga cttacttgg cctttccgtg gcattccttc ctctagggta     17280
tggggcagga ccctctctgg aatgacccat gattagatta gagccctgcc ttggacaggt    17340
gaaaggagga caggaatagg tcagagagaa attttgtttc ctgaggcctg tttctgaggc    17400
ctaaagtgtc caacattata acataagact gtacaaaggg ttttatatat ataataaat      17460
atgtattatg ttgtgcaaaa gtaattgctg tttttgccat tactttaaaa aaatggcaaa    17520
aactgcaatt acttttgcac taaccaaata tatgtaaata tcacaactat ctatacctct    17580
ccctcttctt cttgagattg ggaagcagct caggtctgct ccttctggta tcgaaacctc    17640
ttttggtggg aagcttggac ttcatcatct gacccacatg gattcaaatc ccacctctgt    17700
tccctagtag acttgcatgg tacacataag agctgctatt tcctgagtgc ttaagtatgc    17760
taggcgttgt gctaagtggg ctactacatc aaatcctcaa caagcctatg tgcagatagg    17820
gaaacagagg ctcagaaaga gaagccacct gcccctggtc acaaggtttg gcaaattgca    17880
gtcaagattt gatcccaagt ctgtgatgcc aaagcccact cattgatcca ccacgtggtg    17940
ctgtggacaa atcccttcac tcctcagatc ctcagtcaca tcatctgtca aatcgggagg    18000
```

-continued

```
agtaccagtg gctggcaggt acccaggaca gggtctggca tggtttgcgc ttgcttcctc   18060
gccacttgct tgggcatttt cctgggtttc tgatgcctca ggctcctgat ggggctccaa   18120
acactaaggt ttgggagtga gtgccaggga gaagcttgca attcctttct gaaccaatag   18180
tgttctcagg tttatcaggc aaccagctca ggcctttgat gaactcacta agatatatgg   18240
acctcattac caaccaaagg actcacatgt atttcaatcc tcacttcctc ccctctttct   18300
catttcaact gttagtactg gttgcaaatc atgggaagtt gcttcatcta gtcagtcata   18360
catgtgccta gtccacacat gactgtgctt ttgcatgtca cattcctgca ggcagagacc   18420
taatttggcc gactttgggc aatgactgaa ttccattgac atctgtcaag taggaaaaat   18480
agtggtgcct gactcagaac gcgtggcctg aacgaggctc tgtacttacg ccatttagca   18540
ttgtgcccgg cttgagtgga ttggcggcaa ctgttgtttt taaaggagat ctcattgggc   18600
tggattatgg catgcatggt cctgccaggc ccagggccca ctgtctgtcc tctatgggaa   18660
gatagagggg caggtgacag aacactgagt aacaatccgg agatctcagt tcaaacccca   18720
cctccatcac cagtgacctg cgtgacccta atgaagtcac tcagccttt ggggtctcag    18780
tttccttatc cacaaagtgg agatgattct attcctgatc ttatggggttg ttgtgaagtt   18840
ccaataatat agcaatcctg ataactagtt tttgaggagg gtctttgatg gatgactgag   18900
ccagtggtgg ttgggggggtc ctgggaagta ctgggggagt tggcagtgta gggacatctt   18960
ggtattggga ggggaccttg gtagagggag agggtggagg agggagaatt tcactagagg   19020
gagggagcag tgtggggaag ggcctgaaga gagggaggag ggcaggtggg cctgggtaga   19080
agggagagtg gggctaccct ccaggagccc tcctggccag cagccctgcc ttagcctggg   19140
ctaaccaggc cctgctctca cagctggctg caccttcgag gaggcaagtg acccagcagt   19200
gccctgcgag tacagccagg cccagtacga tgacttccag tgggagcaag tgcgaatcca   19260
ccctggcacc cgggcacctg cggacctgcc ccacggtaag tctactctcc atcgccatta   19320
cccccttcttc tccttccaga ggcacttcta cccacctgct gtgtgacctt gggcacatta   19380
cttaacctct ctgggcccca tctacatttg catctttaat gacatacgtg acactgaatg   19440
tggcttttctc tggacactgt ctaattgtgc atgtcagcta gtttcgtgtg taaaatgagt   19500
gcaggccctc atggctgtga gctaaaactc acttccaatt actccccttg ctgcctagct   19560
caggatccaa accactccca ctctcagttc ttcctaaatc ctccatcttt gagaggctct   19620
cttcagagat tcttttctcc caaagagccc ctgaatcctg gtctctccag gacttgaaga   19680
tgctgaaaga gcagtaacac tgggactaga tgtgtataaa accttccttc ctctgccctc   19740
ttcctcctgg aagtcccaga ttcttctcga cttctacctt gctgtgttcc tatttcaaga   19800
tggggcacct ttgtcatcct gagctctgga ctggagtcca ggagactaat aatatggatt   19860
ctagtactga cttcctgctt tcatcatggc ccctagaaca ctcattccag agtcacgaag   19920
acctgggctc aaaccctgtc tccagtcact ttaccagcag tgtcacttaa cgtatctgag   19980
cctccattgt cttcactgta aaatgaggca aacaggactc catttcagag ggtcatgaga   20040
tgatgcatat aaagtacaga gcacaggggt ggcatgcagg ggtcagttat ttaattgcta   20100
tggttgaggg tctttggggg ccctgattac tagtactgct cttcactgga tgcaggatca   20160
actgggaatt aaaaaagaat gagacaaata aaggccaaat tgtcaacttt attactgata   20220
agggctgtgt cagaggacaa atcaaatggg cttttccgagt gaatcctgaa attccacagc   20280
ctgaagccca ctccctttgc cccatcacac tagtgcccag ggtgtttact gcctagctca   20340
cgtcatggct gagattgcat ctgttgtcag ggaggggcag caaagattct cagtggtggg   20400
```

-continued

```
gccaggactt gaagccacta ggagagaaga ccttcatgac ctggcacagg cgcctcctgc    20460
ggactctcat ggcttgcccc gcctcccctt ctgtgcattt gctcacactg tgcccttcct    20520
ggggcactta tctctgcctc tgcaggtgtt agtgggtatc acagtttgcc ttctctgaaa    20580
ataatctgta aaggtaccca ccatggcagg gacctcgtgt gggcctctcc atattcccag    20640
ggcccagcct cagtctgata catggttggc agtcaggtac aaggcagctg attggaattc    20700
acctcttata gtactgacca ccctgagtgc acactgcctc tcttgtcacg tgcaagcaga    20760
gacataccca gtgagaaagg ggagagggga atttagcaat tagtgtgagc cttgtgctag    20820
gtcttgagga tgtggtggtg agccagatgg acagtctttg tcctcctggt tctcacattc    20880
taggaatggg agctggtggt ggagggagaa gaaaggaggg agattcacac tcagagatgg    20940
agagaggaga aggaagagcg acaggacaaa agggagtaaa tgaaagagaa ggggagggat    21000
gtagtgagcc gaggaggagg cagagggagc aggaggagga ggaaagaaca aagtgtcaga    21060
ttggaagagg gagaaagatg cacacagctg ctcgcaggga gaggagagag aagtagcatg    21120
agtgggccaa gagggagtgt gttgggggtt gagaagtgcc ccttcctggg tggggatggg    21180
gacttgagtt tagtttacta ctgccctgct gggactgatc caggagccgc tccataggg    21240 cttctagctt acagagatga atgagatcgc ctccagcaga gtccctgggg agccctcctg    21300
gagcggggat ctgagtgagc ttgtgttggc tggcagccaa gcccgggagg aggcagcgct    21360
gggtggtttc gggtgccctt tgggaagccc aaatcccccc gccaggtcct gagccagcct    21420
agtccacttc tactccacca gtacccagcc tgggtctctg gggaagggac aggctgcctt    21480
tctccaggtt ggaagtcaag gggatttgta ttccaggaat ttagactcag ggatggggc    21540 tggaagggaa gttggaatcc tttcattcaa tctctgttct acatattcat tcagcttgcg    21600
tcctgaggcc tcacagcctg gtgggagaca cacaggcact ttagtaatga cccaggggc    21660 aggagagaag cccagggtgg gaggcagagg gagggctttg gaaggggtgg cctttgaggg    21720
actgttgtgt gccaagctct tgactccagg gatgaatgac ctagtccctg tctccaggga    21780
tagctcagaa catggggaaa gctgtggtta ggctgggcat gggcattgtg acctgtagat    21840
tgtaaggagc cataattttt tttttctttt tgagaccgag tcttgctctg tcacccaggc    21900
tggagtgcag tggcgtgatc ttggctcact gcaacctctg cctcccaggt tcaagcaatt    21960
ctcctgtttc agcctcccga gtagctggga ctacaggcac atgctaccac accctgctaa    22020
tttttgtttt tttagtagag acagggtttt accatattgg tcaggctggt ctcgaactgc    22080
tgacctcagg tgattcaccc acctcagcct ctcaaagtgt tgggattata ggcgtgagcc    22140
accgcgccca gcctttaaat ggttttgaca aagtcaggtt tgtgtgtttt ttactgctcc    22200
aggtctcctg tgggaaacag atgctaggaa gtgaagggac tcacccaggg aggtggagct    22260
ggggccagaa ctcagaatcc ctgactcctg gtgggtcccg ttgcctggag tcctcctcag    22320
tgctcccctt gccctggccc tgtccctccc ctgaggtctc ctcatctcct gcctcttcct    22380
cctctctttc caggctccta cttgatggtc aacacttccc agcatgcccc aggccagcga    22440
gcccatgtca tcttccagag cctgagcgag aatgataccc actgtgtgca gttcagctac    22500
ttcctgtaca gccgggacgg gcacagcccg ggcaccctgg gcgtctacgt gcgcgttaat    22560
gggggccccc tgggcagtgc tgtgtggaat atgactggat cccacggccg tcagtggcac    22620
caggctgagc tggctgtcag cactttctgg cccaatgaat atcaggtggg ctgggttcag    22680
tcagcggtca gcctgtgcct ggaggtgggg cagatggatg tcaaattgag gttggagtag    22740
atgagtggct gaagttagaa tgtgtctgca ttcagtatca gaggcaacct gtggtcaagg    22800
```

```
ccaggggtca gtctggggcc agtctgggtt cagcatctga ggtcattgtt cctaggaata    22860
gcctctggcc caggtcaagg gtgagttgga acagtgctga cctggaaact ctgtctggct    22920
gcttgagggt aactgtccag gatttgggtg gaaactggcc tccaccttgt tcactatggg    22980
cgctgggacc ccaccccaa ctagctggct tgggagggag ggtcagtgtg agctgggctg     23040
acctctgcta gttgaggcag aggaggctga ggccgagctg aaagtgggca cctccccagg    23100
caaggctgga ggaatatcag tatgatagga gccctcccgc ctcccccagg tgctgtttga    23160
ggccctcatc tccccagacc gcaggggcta catgggccta gatgacatcc tgcttctcag    23220
ctaccccctgc ggtgagtccc agcccactgg gggcgcaggg gtaagggtg tgggcggccg    23280
cggctcctgc ctgcaggggg tgcaggccca gctcacgatg cagctctaac cccgcagcaa    23340
aggcccaca cttctcccgc ctgggcgacg tggaggtcaa cgcgggccag aacgcgtcgt     23400
tccagtgcat ggccgcgggc agagcggccg aggccgaacg cttcctcttg caagtgagcg    23460
ggagcggtga tcttggctgg gggcggggtg ggaggggtt ggtggctgct tctggccctg     23520
actccccca gattgctgag tccctgcttc atactccagc actgcgcaca gcgtcccggc    23580
cctcccctag ctctgctctg cgctttcttg ggtcccccat tccccaggt tagagcgcgg     23640
ctccaggaac ctatgtccgc gcggtgtagt agggacggct aaatgggggcc cgggtcagag   23700
cgagatcggg acccctcgct ccgaggcgcc cctgaccccc tcactctctt ccctgcagcg    23760
gcagagcggg gcgctggtgc cggcggcggg cgtgcggcac atcagccacc ggcgcttcct    23820
ggccactttc ccgctggctg ccgtgagccg cgccgagcag gacctgtacc gctgtgtgtc    23880
ccaggccccg cgcggcgcgg gcgtctctaa cttcgcggag ctcatcgtca agggtcagct    23940
ggtggacgcc ggggagcgcc gggacctcac cctcgagggg cggggccggc gacgggggcg    24000
ggctctgccc gggggcgtgg ccgtgggggg tgggccggc agggtgtcgc tggggcgcta    24060
tctgaagatg ggcctgtgga aatggcagtg gcccagccgg gatgagatct gatctagggg    24120
tcggggctgg cttcgagggg gacggacagg gtcaaggtga gagcctaaag aggggtgggg    24180
ttctggctgt gtgacttctg tgttgatcct agctggcctg cggtccgctc caggaggcga    24240
ggatgtgggg gattaggagg ggcctgagag aggggttgtg ggctgatggg cgagggcggg    24300
gtcagccttt ggagccaggt gccccttagg gcccgggatt tagtgggggt aggagagcgg    24360
gtctggttga gggcttggta gcagcgtgag aggccctagg aggacggaga gggatttggg    24420
tgtggtggaa ctcagagttg ggtgctgggg tctcacagca gcatcggtcc gcctcgcctc    24480
tcccccatct cctcgcagag ccccaactc ccatcgcgcc cccacagctg ctgcgtgctg     24540
gccccaccta cctcatcatc cagctcaaca ccaactccat cattggcgac gggccgatcg    24600
tgcgcaagga gattgagtac cgcatggcgc gcgggccctg ggctgaggtg cacgccgtca    24660
gcctgcagac ctacaagctg tggcacctcg accccgacac agagtatgag atcagcgtgc    24720
tgctcacgcg tccggagac ggcggcactg ccgccctgg gccacccctc atcagccgca     24780
ccaaatgcgc aggtgggtgc agcagctacc cctggcctca gtctctggtg gcccagggc    24840
tatggagggc cgcattcgag aggtagcgtg gcctgtgctt gtaaaccttt ctaaaacatt    24900
gtgattttc ctcaacccctt gttatggtaa agataatgat agctaatact ttactttgtg    24960
tcaggcactt aaacatatct gtgtgtagac acacacaca acccatattt atagatttaa     25020
aacttacaac actaccacga tgtaggtgct cttgtcgtac ccattttaga tgtgactgag    25080
gtacagagat gttaagtgac tggcccaaga gcacacagct agtaagtggc agagatggga    25140
ttggaactct tgactggctg actccagaat ctgtgttctt aattctacat ctagataaaa    25200
```

```
taagcaacta aataccatca aatacaagta tattatacat tctagctggt ttctcttgtc  25260
tgggtgttga gcctgaggtc tgctcttcct tgttaaaaag ggcaaagcag ctgttggagg  25320
atggtacacc tgtgccagat gagggtcttt tttgtttaat cagaagagaa attgagaaca  25380
caataggttt ttcttttttgt gactttagta ttgttgttgt tattattttt ccttttgaga  25440
cagagttttg ctctgtcacc caggctggag cacagtggcg cgatcttggt tcactgcaac  25500
ctccgcctcc tgggttcaag tgattcttct cctgcctcag cctcccgagt agctgggatt  25560
acaggcatgc tccaccatgc ctggctaatt tttgtatttt tactggagac agagtttcac  25620
caggttggcc aggctggtca caaactcctg acctcaggtg atccacccgc ctcggccttc  25680
caaagtgcta agattatagg cgtgagccac cgtgcctggc ttagtgtgtt tttttaatgg  25740
acttactaag ataaatgtag agtcacatgc agttgtaaaa aaaatacaga aagattctct  25800
gtgcaagtca ccctattttc tgcagtggta acatgttgca aaactatagc ataatatcac  25860
agtcaagata ttcacattga tacaaaccac agatcttatt cagacttttc tggttttgct  25920
tgtacttgtt tgtgtgtgtg tatatgtgta tgtagttctg cacaatttat cacatgtgta  25980
ggtttgtgta ttcaccacta cagtcaaaat actgaatagt tcaatcccct taaggactct  26040
tttataacca cattcacctc cctttcttcc tctactcccc aacttttggt agtcactgat  26100
ctgtcctttc taaattttg ttgtttcaaa aatattatat gaatgaaatc agagtatata  26160
acctctagaa ttggctttt ttggataaca gctttattgc aatataatcc acatctcata  26220
caattcaatc cttaaaatgt acagttcagt ggttttagt atacggtagt ccccgtgtat  26280
ctgaagtttc tccttctatg gttttagtta cctgtggtca acttgaggct tgaaaaggtg  26340
agtacaatac aataagatat tttgagagag agagacagac cacatttgta taacttttat  26400
tatagtgtgg tgttgtaatt gttctatttt attattagtt attgttgtga gcctcttact  26460
gtgcctaatg tagaaattaa actttatcat aggtgtgtat gtataggaaa aacatagttt  26520
atctagggtt cggaactctc tgtggtttaa ggcatccact aggggtcttg gaatgtgtcc  26580
cctgcagata tggggggact actgtattga cagagttaca caaccattaa ctcaattaat  26640
taattgagtc aaccattaac cattaatcaa ttttggaaca ttttcatcac ctcagaagga  26700
aattttgtac tctttagcag tcatccccat ttcactcgca cacctctagc cctaggcaac  26760
cactaatttc ctttctgtcc ctatggattt gcctctctgt ggacatttca cataaatgga  26820
atcatataat atataatctt ttgtgactgg cttcttccat ttattttatt atttatttat  26880
ttatttatta ttaagacgga gtttcactct gtcgccaggc tggagtgcag tggcgtgatc  26940
tcggctcact gcaacctcca cctcctggga tcaagggatt ctcctgcctc agcctcctga  27000
gtagctgaga ctacaggcac ccaccaccat gcctggctaa ttttcgtatt tttagtagag  27060
atggggtttg ccatgttgg ccaggctggt ctcgaattcc tgacatgagg tgatccgcct  27120
gccttagcct cccaaagtgc tgggattaca ggcgtgagcc actgcacctg acccttcttc  27180
catttaacat gatgttttca aggtttatcc tcattgtagc atgtatcaat actccattct  27240
tttttattgc ttaataatat tccattatac aaatatatca catttatttt gtcattcatc  27300
agttgatgga aattggggtt gtttacactt ttcagctatt atgaacagta ttgctatatt  27360
tgtgtacagg tttttatatt gatatatgtt ttcatttttc ttatgtacca tatatatcat  27420
aagatatctc tgtgtttatt cattgaggaa ctgctggact gttttccaaa gcagctgtac  27480
cactttaaat ttccactact tgtctatgag ggttctagtt tctctgcatc cttgtcacca  27540
cttgttatta tctgtcttct tataagcact ctagtatata tgaaatggta tctcattgtg  27600
```

```
atttttgattt gcattaccct gatggctaat gatatatcga gcattttttc atgtgcttat    27660
tgaccatttc tatatcttct ttgtagaaat gtcttcagag tgttaaaaat gaccaattt     27720 taagttgggt tatttgtctt tttattattg agttgtaaga ttatttatat attctgagta    27780
ggccgggcat ggtggtggct catgcctgta atcccagcac tttgggggc cgaggagggc     27840 agatcatttg aggccaggag tttgagacca gcctagctaa catgatgaaa cccagcctct    27900
accaaaaata caaaaattag ccaggtgtgg tggtgggctg ttgtcccagc tactcaggag    27960
gctgaggcac aagaatcgct tgaacccggg aggtggaggt tgcagtgagc tgagatggtg    28020
ccactgcact ccagcctggg tgacagactg agattctgtc tcaaaaaaaa aaaaggagta    28080
tttatatatt ctggacacta gatgcttatc agatgtttat gtttgcaaat actttctccc    28140
attctgtgga ttatattttc tttttcttga tagtttttt ttgaagcacg aaagttttca     28200
atttatctat ttttttcttt tgttgtttgt gcttttgatg tcatccctaa gaaaccattg    28260
cctaatccac agtcatgaag atttactcct gtgttttttt ctaatagttt tatagtgtca    28320
gctattacat tcaggtcttt gatccacttt gagttaattt ttcaaatgtg gtgtgaggta    28380
gggatccaac ctcattcttt ttttttttt tgagacagag tttcacccctt gtcgcccagg    28440 ctggagtgca atggcgcaat ctcggctcac tgcaacctcc gcctcccagg ttcaagcgat    28500
tctcatgcct cagcctcctg agtagctggg attacaggcg cgtgccacca tgcccagcta    28560 attttttatat ttttggtaga cagggtttt caccatgttg gccgggctgg tctcaaactc     28620
ctgatgtcag gtgatccacc tggctcagcc tcccaaagtg ctaggattat aggcatgcgt    28680
ggccaacttc gttcttttgt atgtagatct ttattaccat ttgttgaaaa gtctattctt    28740
attgaattat cttggcactg gaattggttt cttttcattca gcatagtttc cttcatccaa    28800
gttgtgtata tcagtagttt attcctttt attactttt attactttt attccatgct      28860 gtggaaatgc cagtttgttt aaacattcac ctgttgaatg acatctgggc tggttccact    28920
ttttcattat tacaagtaaa gcttctgtga gcattcatac agaggttttt gcatgaacat    28980 aactttcat ttttctggga taaatgctca agagtacaat caatgagtca tatggtgatt    29040
gcatgtttag tttatcaga aactgccaga gtggctgtgt tgttttatac tctcaccaac     29100
aacgtatgag tgatccagtt ttctgcatcc ttgccagcat ttagtgttgt cactatttt     29160 tattttggac ttcctgagag gtgtgtagtg atatctcatc atggtcttaa tttgcatttc    29220
ttcagtgtct agtgatgtcg aacatctttt ctttttcctct tttttttttg agatggaatc    29280
tcactctgtt gcccaggctg gagtgcagca gcatgatctc agctcactgc aacctccacc    29340
tcccaggtac aagcaattct tgtgcctcag cctcccgagt agctgggatt acaggcacac    29400
accaccacgc ctggctaatt tttgtatttt taggacagat ggggtttcag catgttggcc    29460
aggctggtct tgaactcctg acctcaagtg ttctgcccgc ctcagcctcc caaaatgctg    29520
ggattacaaa catgagccac ggcacctgga caaacatctt tcatgtgct gtttgccatc     29580 tgtatatcct cttggtgca tcatctgttc atgtctttga acatttctta attggattat    29640 tcttttgtt gttgttgttg ttgttaagta ttgagagttt tttgtacatt ctaggtacca    29700 gtccttgtt aaatgtggag tttgtaaata tttcctccca gtagcttgtc ctttcaccct    29760
ctttatatgg actttcacag aactattttc aattttgatg aggttcaatt tgtaaaattt    29820 ccctttatg aattgtggtt ttggtatcaa gtctaagaac tccttgccta tccctgtctc    29880
ccaaagattt tctcctgggt ttttttttt ttttttttt tttttgata cggagtttca     29940 ctcttgttgc ccaggctgga gtgcaatggc atgatctcag cttaccacaa tctctgcctc    30000
```

```
ctgggctcaa gtgattctcc tgcttcagcc tcctgagtag ctgggattac aggcatatac   30060
caccatgcct ggctaatttt gtattttag  tagaggtggt tggtcaggct ggtcttgaac   30120
tcctgacctt aggtgatccg gcctcccaaa gtgctgggat tacaggcatg agccaccgcg   30180
cctggcctcc tgtttttttt ctaaaagtgt tatagtttta cattttacat ttaagtttat   30240
gatctatttt gggtaaagtg tgaggtttag gtcaatgtta tttgttgcta atcaatattc   30300
gtaagtgttt taaaaagcca atctgtgaat tatctaaaat ccagtttaaa gccacacttt   30360
gggaactcct tggatggtag gtctaaaatc tggtttaatg tcacactttg ggagacccct   30420
gagtggtggg tcagaatgtt ccagtgggaa ttgctttcta gtgaaggggt ctgggtcagg   30480
ttacttaacc tttctgagct tcagtccccc tgttttacaa catgggaata ataacattta   30540
ccatataggg ttagtttgaa gatttattca acgaatgctt attgagtgtc tattacgtgc   30600
gaggtgctat tgtggttggt agggatatat gactataacc aggacagaca aaggccacca   30660
acatgtgagt tcttcctgga actcacattt tggcaagagg agatagataa tagatgagta   30720
aacaagtgaa gtatacagtt ggcctttgaa catcacaggt ttgaattggg cagatccact   30780
tacatagatt ttttttcac  tcacacgtgc atcaaaaata cggtatttgc gggctgggca   30840
tggtgggtta taccttttat cccagtgctt tgggaggctg agatgggagg aatgcttgag   30900
gcaaggagtt tgagaccagc ctggacaaca tagcaaaacc ctgtctctac aacacaacag   30960
caacaataat tagctgaatg tggtggcatg tgcctgtagt cacagctatt caggaggctg   31020
aggcaggagg attgctggag cccaggagat caaggctgca gtgagctaag atttcacact   31080
gcactccagc ctggatgaca gatcaagatc ttatctagag acaaacaaac cagcaataca   31140
aaaaactcca gtgtttctag ggcctgtata tatgaagggc caactatggg acttgaatat   31200
gtgtgaattc ggttatatgt aggggtccta gaaccaatcc ctggcatata ccgagggagg   31260
actttatggc ctgtcagatg gtgataagtg ccgtgaagaa gaaaagcagg gagtggggcc   31320
tggagggttg ttattttaa  aagtctcaag ggaaggtgac atttgagcag agatctgaag   31380
gaggtgaggg actgagccgt gcagagagct gggggcttgc tgggggaagc aagcaccagc   31440
ccgactgagc agccagcaca aaggcctgga ggctggagaa tgcttggcac gtgcaagggg   31500
catccaggag accagtgtca ctgtgttagt gactgagtgg gagatggcag gagaagaggc   31560
tgaagttgag ctgcagatgt gggacttaga gccgttgtac acagagagag ctggggagcc   31620
actgaagagt ttagagagca ggagtgagca tcatctactt ttgttaaaaa ggatcactct   31680 ggccctttg  tggagaatgt tctccaggag ggcaaaggtg ccgcagagac cagggaggag   31740
gctactgcaa tgatctgctt aagaggtggt gatggctggg agccgagtgg aagtggtggt   31800
ggtggggaga agtggtcaga ttctgggttt attttaaagg cagagctaac tgcatttgct   31860
gatggattga atatgggatg agagaaaggg aaatagaagt caaggatggc tccaaggtgt   31920
tttgctagag cagcaggaat gatggagctg tcatttcctg gagcggactg tggtggcagc   31980
tgatttgacg tgggtgtcat agatcaggag ttctgtgttg gaaatgttga cttcgagatc   32040
cctattagac attcaagtgg agatattcat cagcagatgg atacatgagt gtggagttca   32100 gggaagggt  tcgggctgca gatagaaatt tgaaagtcat cagtgtggag atggtataga   32160 tggcattta  agccctgagg ttggatgaga tcttttacgc taatggttct caactagggg   32220
caattttgtc tcctaggaga catttgacag tgactgagga cataaccgtt gtcacaactg   32280
ggtggcggca atggggtgtt actggcatct aaagggatag aggccaggga agctgctaaa   32340
catcctacaa tgcacagaca gccacataag aaagaattat ctagtctaaa atgttcatag   32400
```

```
tgctgaggtt gagaatcccc gattcagtcc ttagattttt agggaataaa tgtagatgga    32460
agaaagagga gttggaaagc ctgaaccttg gagcctccag tgttttgggt taaatgcaga    32520
caattgcagg gaaatgcatt aaatgcatgt gaagtatagc gcttaacaca cagtaagcac    32580
ccagtaaatg atggtgtttt taatctttca aaggcagttc tggtttgcca cttaggataa    32640
aaggaatcat agcacagggt tccgcagagg atctctattg cactcccctt agtgtacaga    32700
tggggaagct gaaacccaga gaggggaaga gacttggctg tgatcagaca gtgggtcaag    32760
aacccaggtt tcatgatgac ggctgttgat tattcccatt ttacagatga ataaactcag    32820
atttagagat ttagccactt gtacaaatct acacagtgag tccatggcag agcttgaatc    32880
aaaatttgaa tctcttgatt tctcatccag tgttttgttt tagttttttg ttttattttg    32940
tttttagaga cagggtctca ctctgtcacc tgggctggag tgcagtggca cgatcatagc    33000
tcactgcgtg cagccttgaa ctcctgggct caagtgatcc tcttgcttca gcctcctaag    33060
cagctggggc tacaggcttg caccaccatg cccagctaat ttatatacat atatatatat    33120
atatatatat atatatttt tttttttttt tttttttttt ttttgtagag acagggtttc    33180
actctgttgc tcaggctgat cttaaactcc tggcttcaag ggatcctcct gtttcagcct    33240
cccaaagtgc tgggattaca gacaggagcc agtgcatcca gcctaatcca gtgttttttaa   33300 cagcagcagc agcagctgct gctgccacca tcatgggctg aatgcccact ttgtgctggg    33360
cactgtgaaa cagttttcat aggctggcca ggacggaagc tggggcaggg gcctggcaga    33420
cagggtgcaa acacctcccc ctgcccttct gaattacacg gttctctttg ttgacatcat    33480
ggcccctccc tgcttaggcg cgttggccgg cagttgtttt gctgttggcc agctgtgttg    33540
tcatctcctc catccccatg aaactcccct cgcactatat tatttactgt aaaaacaata    33600
atatagcatc aggcgaaggc attttttaaa ataagcactc cgaagctcat catcctagcc    33660
caacagctgt tttaattttt ctgacttctt cacatctctg cccatatgcc tgcagtagac    33720 attttacac ccttgcattg ggatgtagaa agcatttcgt atgctgcttc atttgcttgg     33780
tgttgttacg tgtgttatgt tgtttataat tatgtttact gactctagaa gtccattgaa    33840
tgtccccatt tagctggact gttttgcctcc agacttctat aatgataaat aatactatat   33900
tgagaaacct agcgcttgta gttcttccct tctcccccca ccctgagtta tttctttagg    33960
ataaagtgtc aggagtggtt gaagaaaggg cttttaaata tattgcttta aaaatggtt     34020 gtgccaattt atactgctac tggcatctca tgttaatgca cacatgttta ttaattacta    34080
tagactggta atgactgtag gctggtaatg actgtaggct gggcaatttg actcatatta    34140
tctcatgtaa ctctcacatt tgctctttaa agtaggcatc ataatctcca tttgtttgtt    34200
tttgtttctt tttttgacag agcctcactc tgtcacccag gctggagtgc agtggcatga    34260
tcttggctca ccgcttcctc tacctcccgg gctgaagcta ttcacccacc tcagcctccc    34320
aagtagctgg gactacaggc gcgcaccacc atgcctggct aattttttata ttttttgtaga  34380 gatgaggtct cactactatg ttgcccatga aggtctcgaa cccctgagcg atcctgcctt    34440
ggcttcccaa aatgctgaga ttacaggcat gagctactgc acccagccat aatctccatt    34500
ttttagtgga ggaacctgac atcaacattc aaaggggggtt aagtaacttg cctgaagcca   34560
cagaactatg gccaggtgca gtggctcatg cctgtaatcc cagaactttg ggaggctgag    34620
gcaggtggat cacttcagct caggagattg agaccagact ggggcaacat ggtgaaaccc    34680
tgtctctaca aaaacacaa aacaaattaa ccaggtgcat ggtggcacat gcctgtggtc     34740
ccagctactc aggaaggtga ggtgggagga ttgagactgc agtgagccaa tgatagcacc    34800
```

```
actgcactcc agcctgggtg acagtgagac tgtgtctcaa aaaaacaaac acaaacaaac    34860
aaagaaaaaa aagaactaat gagaggtgga gataggatgt gaacttgggt gtaccagatc    34920
ccagtccaaa gctcctccca tgagaaaaag ttgaacattt cagggttatt gcatcttgtt    34980
tagccttact aaagtcaaca catggtggcc taattcaaca gctgttaaat gttatcctca    35040
ttgttttaat gtgcattttg acctctgatc tcggagtgac ctgtagccct gtgtaattta    35100
gagggatggg gctttgaggt ccccaagttc tgttttgtca gcgtgtgttg acagttgaag    35160
agagtgtgtc tgggtgccag atggttttta gaaacgtgga gaaactcatg gattcacacc    35220
cctcaatcaa catatcagtc tgtagtcaac aaactatttg agctccctgg atctgtccag    35280
atatgatcag ggtaggcagg aagaaaaaag aaaagtggac cttcttttca aagagctctc    35340
agtctacctg ggtggatggg aggtggcaca gttgtcaaag aatgagatgc ctaagtctga    35400
agttgggagt tcatcctcc aaagttgcta tcttgggccc tgtaaggtga tttgaagaag     35460
cttgagtagg ttgccagtat ttaaaaatct ggagatttca cataaaaatt ggaatttctg    35520
gctcctcttg aaaaatggga ggatctggca actctgaacc tgtagtcctg cctggcaaca    35580
gtcatctaga ggtgagcagt agctgcccct tttggatggg acactactgt cctgtttgcc    35640
gtggtcttta cccagcatac gtcccccgtt tacatggaac ttctcctgcc cttctgtaaa    35700
tgctgcagga ggactaggaa gcagaatgct tctgccaagc cctagaggct ggaaaggaat    35760
gcagggcagc attccagggg gtggggatgg tgtgagctga gctgcaggga acagagagcc    35820
actcccagta gtgcaaataa agcagtggta cctcggctct tgtagactcc caggacagtg    35880
cacacagggc agccacctcg gctcttgtag actcccagga cagtgcacac agggcagcca    35940
ggaccacagc cagagagttg aagaataacg cgaggacctc tgggaaagat ggcaagtgag    36000 cacacccccag atctgcctcc tctggcgcaa acatagaaga atgatggctt aaaacaaaac  36060
tacattaaaa aaattagaaa aatctctatg ggccaggaat gggagagaaa acctaagtgt    36120
ggtgaatggg cttgcagccc acagtaccca ggatacaggg agcagtggca gccagcccct    36180
cagtgtccat atgggatggg atttggtggg tccctgcttg tggggagaag ggagccagtc    36240
aggaggcagg cttttgttcct agtgagtgct gaaatctctc ttcgatggct ccatgtataa    36300
ctggagacat gctgcttgcc tgcattccag ggaagaaagg aaaccttctg ggtggaaaca    36360
gaatcttgta ttgtgctgta catggggcca gtgttgaaaa ctgtgttact ggtgcactcc    36420
caagatagga gcagcctggg cgaatgcttt cctttgcatc ttcttcataa ggggaattct    36480
gaacaaatta atcacataaa aaatgccact aggggctggg tgcggtggct caagcctgta    36540
atcccagtac tttgggaggt agaggcagga ggatcagttg agcccaggag tttgagatga    36600
gcctgggcaa cacagcaaga ccctgtctct acaaaaaata caaaaattag ctgggcttgg    36660
tggtacgcac ctgtagtgcc agctacttgg gggactgagg caggaggatc acttgagccg    36720
gggagatcaa ggctgcagtg agccgagatc ctgccactgc actccagctt ggatgacaga    36780
gcaagacctt gtctcaaaaa aaaaaaaaa aaaaagaaa aaaaatgct cctagggggtt      36840 gtacttaatc ttcttaagag attgtatagc ggtgctttct cacctgttca ttaagggatg    36900
ctgaggtccc tctagctggg gacactttgc aggcgatcac agaacttgag agtaatgaaa    36960
ctatacttca tggaatcaga gtgtaagaga gaaaaggatc agttgatgca gtcttggtgt    37020
cttccctcat tttactgatc cagaaattga ggcccagaga tttgcccaag atcacacagc    37080
tggtcaatgc agatgcagga ctaagggctg agtcctgggc tccatcttgc ctttgcttca    37140
gaagccttga cttttctttt ctattctttt ttttcgagac agcgtctcac tgtgtcgccc    37200
```

```
aggctggagt gcagtggtgc gatcatggct cactgcagcc tcaacctccc aggtttaagc   37260
aatactcctg cttcagctcc ctgagtagct gggaccacag gcatgtgcca ccatgcccgg   37320 cttattttg cgcttttagt agagatgggt cttctccatg ttggccaggc tggtctcaaa    37380
ctcctgacct caggtgatcc acctgccttg gcttccaaa gtgctgggat tacaggtgtg     37440
agccaccacg cctggccaac ttttatttt ttgtagagat tgtgtcttgt tgtgttgccc    37500
aggctggtct caaactcctg gctccagcg attctcctgc ctgggcctcc caaagtgttg    37560
ggattacagg catgagccac tgtgcccagc ccagtttctt tatttataag atgggatag    37620 cattctggtc catagagtca tcaagaaacc gtaaaacata acatgcacct cccttctgct    37680
ggggtagctc gctctctcct gaggcatcag tgaattccta ttggggaggt ggggagtggt   37740
ggttaagagc atggatttcg gagccagcct gaccaggttt ggatcccagc ttcaccactt    37800
accatctctg tgactgtggg caagttactg aatttctctg tgccattgtt ttcatatctg    37860
tatgataggg ctaataatag cacttgtctc actagattac aaggattaaa tgagataaag    37920 catttttgt ttttttggg acggagtctc gctctgttgc ccaggctaga gtgcagtggc     37980
acaatctcag cttaccgcaa cctctgcctc ccaggttcaa gagactcctc tgcctcagcc    38040
tcccaagcag ctgggaccac aggcttgcgc caccacgcct ggctaatttt tttgtatttt    38100
tcttttttta atagagacgg ggcttcacca tattggccag ctgggcttg aactcctgac     38160 cttgtgatcc gcctgcctcg gcctcccaaa gtgctgggat tataggcatg agccaccacg   38220
cctggtcgag ataaagcatt ttaaagactc gagaacaatg cccagcctat ccaaaacccc   38280
caatacatgt taactgcctt tattatcatt atcattatat aatagattgt gtttcccttt   38340
ttgctttgac agccagggaa cccaccactg aatttgaacc ttatctttag acctccacat   38400
aggacctaat gtcatgtatt tctgtttctg tttccctgtc attctctggc tttatttaac   38460
tatttggctc tcatttccct cattaccctg atttctgtat gttattatat tatatgtatt   38520
actatacatt gtttcagaac aagtttggaa ttaatacctt aagaaaaata tatcaacagt   38580
ttgattcaga ctggcctgtt gtagtccagg gtgatcttga attaggaggt gaactgtgct   38640
attaaaaata aattattggc cgggtgcggt ggctcacacc tgtaacccaa gcactttggg   38700
aggctgaggt gggtggatca cttgaggtca ggagttcaag accagcctgg ccaacatgtg   38760
aaacgctatc tctaccaaaa atacaaaaat tagccaggcg tggtggtgta cgcctgtaat   38820
cccagctact tgggagtctg aggtggaagg attgcttgaa cctgggaggc agaggttgca   38880
gtgagcctag atcatgccat tgcactccct cctgggtgac agagtgagcc tctgtcaaaa   38940
aaaaaaaaaa aaaagctaat atttttgagg gcttattgta tattagccat tgtcatgcat   39000
cctttgtgtg tatttcctta aaccttacaa tgatcctatg aggcagggcc tattatcttt   39060
tcattttgca gttgaggaat ctaaggatca gaggggtgaa gtgattcagc cagcagttgc   39120
cagctgcaag tggcagagcc aggattcaaa tgtagtccgc ctgactccaa agcacatact   39180
tttactccct gtttgatgtt ctaggggtcc cctgagctct tggggcaat ggagggatga    39240 tttcaggcag ctgactgatg ctttctctcc ctgttcttct tcctcttctc ttcccatttc   39300
ttctaacttc ttctctctgc ttcctgcatt ctccagagcc catgagggcc cccaaaggcc   39360
tggcttttgc tgagatccag gcccgtcagc tgacccttgca gtgggaacca ctgggctaca   39420
acgtgacgcg ttgccacacc tatactgtgt cgctgtgcta tcactacacc ctgggcagca   39480
gccacaacca gaccatccga gagtgtgtga agacagagca aggtgtcagc cgctacacca   39540
tcaagaacct gctgccctat cggaacgttc acgtgaggct tgtcctcact aaccctgagg   39600
```

-continued

```
ggcgcaaaga gggcaaggag gtcactttcc agacggatga ggatggtaag agtctcagtc   39660
ccaattcccg gggccctgtg tacctcccac agatacgcca tgtctgagac tgaaatttac   39720
tgagggtatt tttttctttt ttttgcttag gattaaacca actgtataac accaaagtag   39780
tgatagctcc tatttttttct ctggaagact ttgggttaga ttggtctaat ttctttcctt   39840
aagtgtttga aagaattcag cagtgaagcc atttgggcat agagttttct ttgtggcaag   39900
gtttttagta aattttagtt tttaaaatag atattgggat attcagattt ttttattctt   39960
gtatcagttt agatggactg tatttttttaa ggaatttgtt cattcaccct aaattgtcaa   40020
atttcttgag ataatgttgt ttataatttt tttatttat ttagagacag agtcttgctc    40080
tgttgcccag gctggagtac agtggcacca tctcagtttg ctgcagcctc ctcctcccag   40140
gctcaagcga tcctcccacc tcagcctcct gagctgggac tacaggcatg caccaccacg   40200
ccaagctagt ttatttattt ttgaggcagg gactcacact tttgtccagg tgggagtgca   40260
gtgtcatgat tatggctcac tgcagcctcg acctcccagg ctcaaatgat cactctacct   40320
cagcctccca agtagctggg actatagacg tgcactgcca tgcctggcta atttttttgt   40380
attttttgta gagacggggt tttgccatgt tgcccaggct ggtctcgaac tcctgggctc   40440
aagtgatcca cccaccttgg cctccaaaag tgctgggatt acaggcatga gccacttcat   40500
ttgccaatat tctttattta tatttattta atgtccatag gctctatagt gatatcatct   40560
ttttcatttc tgatattggt aatttctgtt ttctttttc ttgtttaccc ttgtgaagac    40620
tgtataaatt aatctttcca aagaaccaac tgttggctta cttgattttc tttattttct   40680 atttttatt tcctttgtta tacttctttt ggagttgatt tgctgttctg tttgccttt     40740 gagatagaag tttcttagat cattaatact gagcccttct tcatttctaa tatacgtgtt   40800
taaagctaca cattttcctc taagtcctgc tttagctgtg tcccacaagt tttgatattt   40860
cctatcttca ttatcattca gttcaatttg ttgtctatac aattgaactg ttatttctgt   40920
tataatttct gctttgacct aagagttact tagaattatg ttgcttaatt tctaagcaat   40980
tgggactttt cttttttgtt tgtttttgag acacagtttc actctgtcac ccaggctgga   41040
gtgcagtggc acaatctcgg ctcactgcaa actccgcctt ctgggttcaa gtgattctca   41100
tgcctcagcc tcctgagtag ctgggatttc aggtgcccgc caccacgcct ggctaatttt   41160 tgtatttttta gtagagacag ggtttcatca tgttggccag gctggtctcg aactcctgac   41220
ctcaggtgat ctgcccacct tggccctgca aagtgcggag attataggca tgagccactg   41280
cacctggcca gcaattggga cttttctaat tgtctttta ttattgattt ctaggttaat     41340
tccactgtag tcagagtata tactctaaat tttattttgt gaaatttcat ctttacttta   41400
tggcccaaca tattgttaaa ttttggtaaa tgttccagtg tatttgaaaa gaacatgtat   41460
tctgttgctg ttgaatgcag tgttctacat atgtcaaact aatatttagc ccttagcaca   41520
ttcaagcacc attctgaatg gttttgatat attactgcat ttaatacccca tgacaaccct   41580 atgtggtagg ttactatttc tattcccatt ttatttctat tcccatttta cagaagaagt   41640
cacagaaagc ctggctttct aacctgacca tctggcttca cagttgtcat tcttttttttt   41700 tttttttttt tttttttttt ttttgagat ggagtcttgt tctgttgccc aggctggaga    41760
gcagtggtgc aatctcaact cactgcaacc tctgccttcc tggttccagc gattctccca   41820
cctcagcctg tcgagtaact gggattatag gcacctacca ctacgccggc taattttttg   41880 tattttttggt agagatgggg gtttcaccat gttggccagg ctggtctcga actcctgacc   41940
tcaagtgatc cgcctgcctc ggcctcccaa aggtgctggg attacatgcg tgagccaccg   42000
```

```
tgcccagcca gttgtccttc ttaagagcta cactcgaatg ctatcacagg tccaaagcct    42060
ttccctgggt tcctacagat tccagttacc actaagctcc ttggtttatg gctttgtctt    42120
gctgccgcac gtgcacagtt ttctgttctg cacagcattg gcctagattc aaaattcagc    42180
tccttcttta ctttctgctt ttctctgcct taggacttca gcttcCccat agtggtttat    42240
caaggtattt tcccaagcaa agatcattct cttcctaaat gacactcctg tgcctgccat    42300
taacagtata catttacaca agaaaaacaa aacaaagcca tgcctgcaag tgttaatgct    42360
aaaatgttaa cagtatctct gggtgataca attgtagatg ccattaattt tctttaagct    42420
cattttgatt ttctacattg aacatgtcat ttatgtaatt agaaattttt agacgagaaa    42480
atatcgccac ccataatccc aataccgcaa tgcaattgct gttttcattt ctctggccca    42540
tgtgcatatt ttctgaaaac tacccaactg gaacaaaatt ggagccttca aacgtatttc    42600
tctcctgaat gcaacctaca cagtaatgaa aatgccagct atccattttg agtacttagt    42660
aataggttga accatatgca attgctgatg tttgccttgg ggctttatgt acatcacatc    42720
atttgagtcc tggcttgaga ggggttatat cattcccact tcacagctga gttaagtaag    42780
gtgcagagag gctgaatagt ccatgagaac caggtaggaa gcggcaaggc tggaattaa    42840 acccaggtgt ctggcaccaa agcccacttt cccctggccc ctgctgcctt tcccttgcag    42900
tgcccagtgg gattgcagcc gagtccctga ccttcactcc actggaggac atgatcttcc    42960
tcaagtggga ggagcccag gagcccaatg gtctcatcac ccagtatgag gtgggtttgg    43020
gaccctatta cagtggggga ccctggtgga aggtgagagg tggccctctt tctctctgct    43080
gctacagtag gaggtgcatg ggaggacaga tgtgattgtc atagtttctt caactatggc    43140
caggtctgtg ccctgtgtat tctagaggag ggtcctgaag gcaggaggga gagccgaaga    43200
tgactagaag cctggcttga tggcatccat agtctccttt gcttagcctt atctctcact    43260
tccctgggac atggtgggtg gaggctgctg gtcaggatg ctctgaccat ccagtgccca    43320
cctgcctgcc aatcctgccc ccagatcagc taccagagca tcgagtcatc agacccggca    43380
gtgaacgtgc caggcccacg acgtaccatc tccaagctcc gcaatgagac ctaccatgtc    43440
ttctccaacc tgcacccagg caccacctac ctgttctccg tgcgggcccg cacaggcaaa    43500
ggcttcggcc aggcggcact cactgagata accactaaca tctctggtga gccccacctg    43560
acccggccca gcctcttcgg aggtggccca gaatcccagg gttccatggg cagaagggaa    43620 atgggggca tcctgggggt agttacagag ggcccctgct gagataaata tgccatttag    43680
gagttaaagt caggctcagg gaggatgaag tcagaggagt caggagactg gtcagtgaa    43740 tcagaagatt gaggttgggg ctggtgcctg aggtcagggg ccagggtagc tcaggtcatg    43800
tcagcaggaa caaagaggct aaggctgaag taggggagat ctgaggactg tggtcaagga    43860
ggctggaagc ctggtcttcc tggtccagtg gccaagctcc agcttgtgac cctgtccct    43920 tctccagctc ccagctttga ttatgccgac atgccgtcac cctgggcga gtctgagaac    43980 accatcaccg tgctgctgag gccggcacag ggccgcggtg cgcccatcag gtgggaaagc    44040
ggggacggag gggtgggagt ccagggcctt aggaaagagg cccctcctct gacccagagc    44100
cccatcccag gccagctcac ccttttcctc cctcagtctc ccacgcaggg cttggagtgt    44160
ctggaggaga ttgttctgtg atgccttggca ggcaagaagc ctgcagtccc tcccctctga    44220
ggccatgggt ctcagatggt gactgtcagg aggaccctgg ataggtccag cctggagagg    44280
ggactgtcca ggcctgtcca gggggccttt cctcagacac cttggagaag tgaaactctg    44340
ggggccttat atcatcccag cctttctcctg gaagcacaga gatgggcttt ctagaaggct    44400
```

```
ggggcagcca gccagatagg gccatctctc tggaatggct aggagcttgg cttctccacc      44460
tcctctcccc agaggaagct gggcttgctg gtgccgtggt ggctgcctct gctggggaga      44520
gggtgctgga gacaagactg tgtgtgtgtg tgtgtgtgtg tgtgtgtgta tgtgggatgt      44580
gaaactgggt gtgtctttgt gataaagaca tgggatgtgt ggtgtgagtg tgtgtgagag      44640
gcgtatatgg gagacataag tgtgcatgtg tgtgagagtg tgagggtgtt tgtgcaactg      44700
tgtgcacgta ctgttagcca gaccccgtgc taggggcttt atctgcatga agccattat       44760 cctcatggca gccctgtggc atgggtatta ttaccttcat tttacatatc gggaaactga      44820
ctcagagcct gaatcacttg ccctcaaggc cacacagcta gtaagtggtg gagctgggat      44880
ttggaagcca ggtctatctg ctgtgcctgt acctttcta gaagttatag agcctccctg       44940
cccttctggt ccaccccttc cttccacgaa ggtacatgct ctgggagagg gtgacagcct      45000
ttaggtgggg ggggtgtgag ggtcctagtc agttccctag aagagagtg ggctgcctgg       45060 gtgaccatgg cagtccctca cctcctcact ccccactgta tcctctcctc ttctgctttg      45120
tcttccctgt atttgccact gcaaatcctg ccctgggctg attcccagac cctcagggaa      45180
gacccaggaa aaagtcacgg ggtctgcagg gccttttgcc tgttgctaga gcctcagggc      45240
ccttatgcca ctgagtctgg gatgggttgg gaacccttc tttcttgtcc tcttgaggga      45300
tcctgtgagc agcactggtc agggtccctc aggatgatga ttcaaggct aggtgggggc       45360 aggcttggtg ggaggggagc ggcaagatgg ctgcatgacc ctgggcatgt cccgttacct      45420
tcctgagcct ccgtttcttt atctgcacaa tggggattat tctagattaa gatgcacttt      45480
gttcatggct aatgttaatg attacctcct ggtgggattt agggctagga gaggcctgac      45540
cttagcctgg ggcaatggag gctgaaaggg gcttggactg gtgtttataa tgggctagtg      45600
acaagccatg ggctggtgtc caacactctg ggatgattcc ccacaacttg gatgctccaa      45660
agaaacatct ggtgagcaag gaaaaggcat ttctgcttcc ccaaggagag gctgtcagta      45720
tgggatgtca cacgccaaga cgtgaccgag actgtaactg gaaatattta aatttgtcag      45780
gattcactta tttactctcc actttgttct gcagaggatt tggaggagct catagcagaa      45840
acctatttag taaagagata aaatagaaac acagctggga ccaggagca cgaaccagag       45900 tgggcagtca ggatcctgaa acagcagggc tccgatttgc tgatcagagg ctgccttggc      45960
attgggaggg tgctagagac atagtgttgg gtgtccttgt ttgctaaatc actgtctctc      46020
actagaggtc agttttagga agcccagttg cctagtgtat agcacagggc tcatagtctg      46080
agctcagtca tctctttctg aatgaatgaa tgaatgaatg aatgaatctg ctaaccctg       46140 tcatttactg agtcccagaa gggagctttc agtagctttg gtttcccagg tcttgtgtca      46200
cacacacagg aggactcatg gaggaagcag gctgggcct tatggcttgg ttatattgag       46260
cagggtccac gatcctctta gcctggatta gtaacaggaa taaccgctga caggtgctgg      46320
ctgcttgctt aacttgcctg ttcttcccat ctatcttctg aacagtcttg caattactcc      46380
cattttatgg aggaagaaac cgaggcccag ggaggttagg ggacttgccc agctagtaag      46440
gagcagtgtg tggaagttag tccccaggag ggcttgacca caaagcccat gccttaact       46500 gccagctggc tctcccagtc ctctggccgc ctgtgatccc ctgtacgctc tcctccctgt      46560
ccagtgtgta ccaggtgatt gtggaggagg agcgggcgcg gaggctgcgg cgggagccag      46620
gtggacagga ctgcttccca gtgccattga ccttcgaggc ggcgctggcc cgaggcctgg      46680
tgcactactt cggggccgaa ctggcggcca gcagtctacc tgaggccatg ccctttaccg      46740
tgggtgacaa ccagacctac cgaggcttct ggaacccacc acttgagcct aggaaggcct      46800
```

```
atctcatcta cttccaggca gcaagccacc tgaaggggt gagggaccgg ccagggtcat    46860
ggtgggcgtg gttgggtgtg gggggatggc agacaggaga taccttggag caggcccagc    46920
gcagactcca ggcccggcac ttcccatagc cccacctccc atagcccac ctcccatagc     46980
tcctcctcct acagcccacc cccatagccc tacctcctgt agcccacct cccatagccc      47040
tggccccaca gttcctcccc cataaccttg cccctcccat agccctgcct ccttttgccc    47100
acctcccatt gccccacctc caatagcctt acctcccata gagccacccc cacggccccg     47160
cctcccacag ccccacctcc cagagtccgt cccatagtcc cttctcccat agcccctccc     47220
ccatggtccc acccctccca tagccagccc tcctgacccc aggctccttc ccacagagca     47280
ctacccccctt cctgagccctt ctttctcagg ctcctccttt ctatccaggt ccccagtcta   47340
gtctctgccc cttcctgagg ccctgccttc tatcttagat gcttctcttc ccagaggagt     47400
ccatctcaga ttccagcgtt cctgtgttaa ggcctaggac ccgcctcctc cctgaagccc    47460
caccttatcc tccaggctcc tccctcctct gcttcttgcc tggtttcttg cctggtttct    47520
gacttcctag ctggacctct ggccctaggc ctcgcccga tgcccgaggc ccgcccatt      47580
tccccaagac gtttgtttct cttttgcctc cgatctcatc cccctttcct aaggcactgc    47640
aggtgcctcc cctctaggcc ccgctctcaa gggtcccccc aggcctgcct tcgggtgggg   47700
tgtcccttga tgccatcagc acaagacaaa gccctgaaca ggcccaagaa acgctgtctg   47760
aggttcccac cctggggagg gagaggtcgg ggcttcagca acgctgagac ccccatctgt    47820
gcctccagga gacccggctg aattgcatcc gcattgccag gaaaggtaag tccgctgagt   47880
tcctgcagcc tttcagcggc aggtttctca cctgcccagc gctggggagg tggatcctga    47940
ggacctacgg ctgtgggagt agaggagggt ggttgggcag tcctggggcc aggagggct    48000
tcctgctggg tttccatgtg ccctacctca agggcgcctt ctcccagggt gacagcaggg    48060
gcctggagca ggcttgtgga gaggagccat tatagttggg ccttgggggt gatgggtaca    48120
gggtgctggt tctgggttac gtatctgtcc ggctttcctg tggtggggga aaggtgagg     48180
tcagcatggg ccctgtgcta taggtatctt tcctgcttcc agacaggaa tgtggttggt     48240
ttcccatcct gagatggact aaccatgccc taggtacaca attcctaatc cctgttacct   48300
cccaggaggg caagagggtg gggctgaagc ccaggtgtct gctctcccct atccactgag   48360
agctgggagg atctgagaaa gtgggaagcg agggaagcta ttcctggcaa aggagccata   48420
tcagtgagga ctgtggcgtg gaagtgcaga aggtatcagg gatggtgagg aggtagattt   48480
gctcaaaagg caggacacac attgaggatg tagggcggtt tgtgcagccc agtttgttcc    48540
ttgggcacag ccacctacag gaggggctcg atggtccctg tctttcctct gatcccttgt   48600
tctgctttgt tctccccagc tgcctgcaag gaaagcaagc ggcccctgga ggtgtcccag    48660
agatcggagg agatggggct tatcctgggc atctgtgcag gggggcttgc tgtcctcatc    48720
cttctcctgg gtgccatcat tgtcatcatc cgcaaagggt gagtgaggcc ggtgccctgt    48780
cccaccagtg gcttctaccc cttagaggcc tggtggcaca gaggaatagt ggctaagagc   48840
tggtagggca gctgtcctgc aggtgtgtgg agggctgcca gctgggcat cgcctctaca    48900
gatggatctg agctgggtgg tgggaagcca gagactggga agatggggct gccctggagt    48960
ggcatggctg gagtacagtt ctggctggtg ccaggtgctg ccatccaggg aggggtgctc   49020
agtgcctggt gccaaggagc tatgcctgct gggactgttt caatagggag gcatagagg   49080
tgacctggct ttgaacccct accctcctgc agacctcag ccaaggtgtc tgccctgctt     49140
atgggattgt gcagttgacc tgagcagagg atggagctca ctcctctta aaccaagggc    49200
```

```
cctgagccat ggctcttccc gggatccacc ttctctcagg ctcaacttgc cctggaccct    49260
gttcctgtgg atccttgagg agccctcctg ggctgtgac tgataaaccc ctccccctgc    49320
cgcccctact atccctcgtg tctcaaaggt ccagcctgtg tttgcatgaa atgtgtttcc    49380
tagcggattt gcagagggca gcatatatcc caggacattg tggaatccag aacctagaat    49440
cttgcagttt cagaaatgta ggatttagga ctctaggaat cttaggcttt agaattgtag    49500
aggctcagag ccccagaacg taagagctgc caggtagttc aaggccatct agtcagtgg    49560 ttttcaaatc tttttaaaga aacagaacct gccttcaaaa caccagaaaa cccttccctg    49620
ggagcctagt aaaatggagc agatgaaggc tgagcagcag tgctggtcgg aagctgagtg    49680
ggggcttctg ggacttttct gtttgccagc tctgccccac catgttcccc accaggcagc    49740
cgtgggacac tgtggtccaa gcgccttaaa tgagggatgg ggatgttgag gcctagaggg    49800
cacgcagggc tgcccaaggc tacccggaga gccagaggca gagccagctc caccccttccc   49860 cacctggggct ctggcttcta tagccccctac tgctgccagg ctgggcatac atggatgagt   49920
tggttgtatc tctgggctgc caggagcgga taataggatc caggaagatg agagagagag    49980
ctggctgggg ccaccttgcc tgaggccaga caccagcaag agagagagag tctaggggtg    50040
gagtgtgcag cggagtggag gagatggggg ggatggccca gccagggcga tacactctga    50100
tttttcccct cgttgttcct gcacagcttt aagagagact attttaaagt atcatttaat    50160
gagggattac tatgtgccag gagcttcaca cacatcatcc atgagtacat tagttattgg    50220
acatctactg tgtaccaggc actgttctgc actcagcatg cgtcagagaa catttccttc    50280
ttggatcttg actgactccc ttttttttgg atgaagaaac tgtaatgaaa gcaccttgcc    50340
caggccactt ggctgatgag cagtagggcc tgacttcaac tcaggctcgc ctacaaatgt    50400
gaaggcctca ctgagtctgg tgcataggca gtgcccccag aatggcaagc ccctgacttt    50460
cccccagcag ggggcctgag aagtgacttt aagtagggct ggggctggag agggctatag    50520 tggaggggc agatttcagt ttcaggtggt atttgaggtc ctagaaatct accctcaagg    50580
agaagaggat tggcagagtg aggggtgtca aagagagccc tgcaaagaga gcactgggcc    50640
caggacaggc tggatcagaa atgttgtcag ggcctcactg gaaaccttc cattatgtat     50700 ttgctacccc ataaacccaa gttatcccag atgcctccag gaaccctca tcccccatca    50760 ctctggacct ccttacttcc tctaaaagcc attcagtctc actgtgtagt acccactgca    50820 tgccctgga tctgagcctg gccttcaggg ccttccgtgc tcctcagggc ttttgcagtc    50880
tgcattgtgg gtatcatggg atgcagcagc cctggcaggg atggggtgt tcagatcaac    50940 gtggggtgcc aacataacta acaagagtag gaagttgctg aggagggcag ttaccacgcc    51000
cccaggaggg agtcccaggg ggattatggg taatagaggc cagctggaag aagatttcag    51060
attctccatc ctgccctgcc tctgtggacc atcagactgg atgcatctgc tgtaggggaa    51120
ttccagggcc tggaagggag gctggtgacc ccaggccagg tcagatcccc tggctgtgct    51180
tccagaagtc cccatacccc accccttctcc atggcagcac tttcttctcc ctgcactttg    51240
tcatttactt acttgtagtg ttttgctcaa tgcttgcctc ccctcctggg ttaagagctc    51300
catgaagggc agagaaagcc ctgtcttgtc tatatctcca cagtctagcc caggggagtc    51360
gggtctcccc actctgaggt gtagggagga gtggtttgtg ggcactgctg ggtgcttccc    51420
ggtgctgagg cctcacagca gtccctgtgg gagattatta ttaacctcac tgtgtatgta    51480
tgtttttttt tttttttttt ttaaatggac tcaagtctg tcatccaggc tagagtgcgg    51540
tggcgcgatc tcagctcact gcaagctctg cctcccaggt tcacgccatt ctcctgcctc    51600
```

```
agccttccaa gtagctggga ctacaggcgc ccaccaccac gcccagctaa ttttttttt     51660
atttttagta gagacggggt ttcaccttgt tagccaggat gggtatgtat gtatttttg     51720
agacagagtt ttgctcttgt tgtccaggct ggagtgcagt gatgcagtct tggctcactg    51780
caacctctgc ctcctgggtt caagtgattc tcctgcctca gcctcctgag tagctgggat    51840
tacaggcgcc caccaccata ctcggctaat tttttgtatt tttagtagag acagggcatc    51900
atcatgttgg ccaggctggt ctcaaactcc gacctcagg tgatccaccc gcctcggcct     51960
cccaaaatgc agggattata ggcctacctg agccaccatg cccaggctta acctcacttt    52020
ttaaagaaga aagtggaagc gcatggaggt gaagttcttt tatttatttt tcctcattta    52080
ttgattactc cattcaacaa aatatttatt gtgggattac aatgtgtggg gccctgggga    52140
aactgaggga gacaaaaaga caaggattct gtcctcctgt actttgtagc cagtggagag    52200
cctggcatga aattagaaaa agcacaaatg gaagagataa ttgcaaattg tgaaaagaac    52260
aggtgctgg gtgttgggg caaagagaat acaagagaca tcatgtagct ggcactcgtg      52320
ggagagtggt ccgggaaggc ccttttgaag gcacaatgtg tcaactgagg ccagaagaat    52380
gccatttctt cagccgtgtc ctccctcgtg gggcctctgc aacagcccca gcgccctaga    52440
ctctcccctc tctccctggg atggaggaga tgtgctctgt gacctggggc caagctcctg    52500
cctttgctgg tccgtcttcc gctctcctcc ccttcatctg caggatttcc tgtgaaggc     52560
cattctttgg ggtccctgct gacagggtga tgtggggca agtgaatgga ggcctctgga    52620
gagcctggga ggggagcaca gaggaagttc caggaccagg gtcctggggc aggtgtttgc    52680
tctggactct gccactgacc cccagagagg cccaggtagc ccatgctccc tgactcagct    52740
tccccgccta tgaaatggga atccaacctg ctttacactg tgggtgcttt gcggtaaggt    52800
agggctcttg atggaagctg tgccccaggt gctcccagag gggatgacct ggctcccttta  52860
gtggatccca cacccagggg caggcagggt aggtaagggt gggccctagt tgtgtcctgg   52920
gcatacatct ggagtcctct ccatcctgcc ccctttctgt ccccacccag gtggaggtgc    52980
aggcaaaggg ctgacccctt atgggcagag ggccgtgcag ggtgggaggg tggggatga    53040
gaacagcccc ggtaagcaca gttagcctag agagtatgag tctgtgtgtg tcaggggatg    53100
tctaatgtgt gtgtgtgt gtttgtgaat atatgtctaa gtgagtgtgt gtcaagtgtg     53160
tctgaataca tgtgtatgca tgtctgcacc tgtgtgtctg catttgtggg tgttgatatg    53220
tgtttctcca tgtatgagtg tgtatgtgag catatatcta catgtgtgtc tgtgtgagtg    53280
tgcatatgtg tatgactgtg tgaaagtctc tgcggccccct aggtcctttt cccacctcct   53340
cctcactcct gcagtaggct tggggaaggt ttcagaaggg ccttgggtcc tggtcattaa    53400
tatctgagcc tgaccaggga ggtcctcctg acctgttcag tccctggcca gcccctccc    53460
cagcccggga ggtacccagg ccccaccctg ctgcctgggc attgcctcag cccggccttg    53520
gtggacggac ctcggacaca actgtgctgt tctctctttg cacgctgcca ggagagacca    53580
ctatgcctac tcctactacc cgtaagtagc tctaccttgc ctgggagtcc ccggccctgc    53640
ctaggggag atcccctgtc cccgccttct ctggttgggc ttagtctcgc tgcacccagc    53700
ctggcctggt gtccacccgg ttctctctgg tcacctcggc ctctgacttt ctttcctctg    53760
ctctgtcctt cccctctgca tcttcctcct caagtcgtgg tcatgagtgc tggttctgcc    53820
cctaagaggc atgggttcag agctggccct gctgagtcac ccccagcaag tccctgagcc    53880
tcaatgtccc cttcaccacc agagcagccc cttacgtcta ctgttcctcg tggttagaag    53940
tatgtcctga cctccaacca aatccacgtt caggacacgc tctggagccc acgtccatgt    54000
```

```
gcatgtgtgt gcttgtgtgc atgtgggtgg ggcctacctg ttctgagact ggcagcttct    54060
cccacagcac aggcaactct caggccccta caagtccctt ctccagccag gcagcccag     54120
ctctgcagac ccaccatttc ctgggagcct cctctgggcc aagccctgtg ctcagttctt    54180
gacagagtcc tcacaacagc tctgagaaat aggagctttt atcactccca ctttactgat    54240
gaggaaactg aggctcagag agaccaaggg agttgtggga ggttgcaaaa tgcactggaa    54300
ctgggataca acccaggccc ctgctgactc cacagcctgc cgatgctact ctgtcttctc    54360
tctctgtctt ctactctgca agccttctgg aacattcctc ctgcccctgt gctggttttc    54420
cctccctcga agtgcaggcc cagagggcgc caggccagcc ctgaggacag tgggtctctc    54480
acctcctcct ccctggacag ctccttacct tagtgtttcc tgacacgagc ttttccaaca    54540
actcaacacc cagcgactcg cgctgagccc ccagctcggc tcctgcaggg gctgtggaca    54600
ggcagctctc cctgctgctt gcgcagttag ttttcaaaac cagatgcaga acttctcaaa    54660
gaatctgtat taaattccat ctgcttaatc tcacattgag ctcagctgga tgccaacagc    54720
attaggtgtc cctcccgggt tccatcttct ggggatcggg ttggtttgtt tctgtagctc    54780
ttcttccagg taggccagga atcctgggct gggaacagag cctgtggcac accccctggag  54840
accaccctct aggccagcat ctgctcagtg acgggtcctc tctgggctcc atgttcagcc    54900
aggctggctg gctgtcctct gtccatggcc ctatctcccc acctcctttt ctccctccca    54960
cttcctcca agttccttcg aagtcacaaa ctgccatcct catccgtgaa gctgggcctg    55020
gagggagagg aggtctctct ttctcttccc tgctgctctg agcagcagga cggactggtg    55080
ggcagtggtg ggaatctgga ccttctgtgg gtctctttac aagtctgtgg tggtctatgc    55140
tgggaccatc ctaggtgcta ctgggagtag ggagaagcca agggtggagt tcattctgtg    55200
cgtggggaa gccccccgagc tctggctgag cacaagctag actctctgcg gggaaggagg    55260
ggtgtagtcc ctccttcctg caggagaagg aggagtctgg agagtggtcc ctgtttaaca    55320
cggggaggag agaggtgggg acatgctggg cctggagctg ggccagccat tttcctagtt    55380
tggggtgcag tgggggtgag ggggctgtct gctgtgacac caaattagcc ctggagtgac    55440
tttctttccc atttcctaag cccagggggc cagtgaaact taggagtgag atcccagcct    55500
gaagccactg ctgctccacc cctttccctt agcaaaggtc cctaggacgg gctctgccaa    55560
gcccttttca gggaagaagc agctctgggt ctaatgagtg aaggatgggg gcagagccct    55620
cagcatccag agatgcttct aggacagctg ctggctcctg gccttgaggt ccccttactc    55680
cagggcctcc ccagccacct ctgggtgctg tccagcccca cacaatgcct gtgtctcccc    55740
tcaaccccccc tctccaggaa gccggtgaac atgaccaagg ccaccgtcaa ctaccgccag    55800
gagaagacac acatgatgag cgccgtggac cgcagcttca cagaccagag caccctgcag    55860
gaggacgagc ggctgggcct gtccttcatg gacacccatg gctacagcac ccggggtgag    55920
tgcccggccc tcctaccccct tcttcatggc tctgggctc ccaacctgag acaataggt    55980
ccccacatca ggtgagttct gtaacacctg caaccaaaag tgaagcatct gtggtgctcc    56040
tgctggatac cttctggata tagagccagc acaggtggcg tttttgcatt gtgtactaga    56100
ggagcttgca aggaattctg ctagcaaaag aggaatgcaa ggtccattgt gacagtcgtc    56160
aaggaggagg tgctgctgta ggatcagagg gatcagagtg gcctcacccc ttattgagca    56220
cctgttatgt gagaggtggg gatacagtgg ctgagagaga ccgatataga gtcagacctg    56280
ggcttacctc tccctttctt agctgtgtga cctgggcaa gtcacttaag ccctctggat    56340
gtctgtttcc ttgtgtataa aatgggaatg cagattgcct ctgctagtag ggccgatgtg    56400
```

```
aagactaaat gagataatgt gtgcaaaatc acttagggct gtgcttgtat tcacagaata   56460
tagtgagtca gccgttatgt actaggtctg tgtcataact tgcttcatcc cacatctttt   56520
tattctgttt agtgttgatt tgtacagaag agaatatgta atgtttatga aagtcataaa   56580
atcataacaa tacaacaaac agcaatgaac ctcattggtg aattagaaca ttatcttggt   56640
acacctccct ggctatatcc cctacctctt tcttagatgt aaatattccc ttgaaattgt   56700 tgtgttttt ttttttttt gtgagatgga gtctcactct atcacccagg ctggagtgca   56760
gtggcatgat ctcggctcac tgtaacctct gcctcccagg ttcaaacaat tttcctgcct   56820
taacctccca agtagctggg attacaggca cctgccacca tacccggcta atttttttgt   56880
ttttttgaga tggagtctca ctctgttgcc caggctggag tgcagtggtg tgatcttggc   56940
tcactgtaac ctctgcctcc agggttggag caattctcct ggctcagcct cctgagtagc   57000
tgggattaca ggtgtgcgcc accacaccca gataattttt gtatttttag tagatggggt   57060
ttcaccatgt tggccaggct ggtcttgaac tcctgacctt aggtgatcca cccaccttgg   57120
cctcccagag tcttgggatt acaggcgtga gccaccgcac ctggccagtt tttgtatttt   57180
tagtagagac agggtttcac catgttagcc acgctgttag ccacgctggt ctcgaactcc   57240
tgacctcaat tgatctgtcc gcctcagcct cccaaagtgt tgggattact ggcgtgagtc   57300
actgtgccca gctccccttg aaatttgtgt ttataatttt cctacctttt tcggggtag   57360 tttttgttt ttttttttt tgagacggag tctccctctg tcacccaggc tggagtgcag   57420
tggcgcaatc tccgctcact gcaagctccg cctcccgcat tcatgccatt cttctgcctc   57480
agtctcccta gtagctggga ctacaggcgc ccgccactgc gcccggctaa tttttttgtat   57540 ttttaataga gacgggattt caccgtgtta gccaggatgg tctcgatctc ctgacctcgt   57600
gatccacctg cctcgacctc ccaaagtgct gggattacag gcgtgagcca ctgcgcccgg   57660
acttttgggg gtagttttac catgtgtaca tatatcccca acaacgcat tgtatagttt   57720 tgctcatttt catcctttat aaaaatgaaa tcacacacta cttaactcca catcatattt   57780
aaatttaccc atgtggatgt tttgctgcag ttcatttact ttctctgatg cgtagttcc   57840 cattgtatgg ctgtatcaca attgacttct ccattctgcc atccatgggc attcgattgg   57900
tttttagttt tcttgttatc acaaatgaga ctgctgtgaa tattctgatg tggatgtcta   57960
gatgcacctg cacacaaggt tctagaaata gaattgctgg attatggagt acgtgcatct   58020
tcagcttaat aagagtgcca agttgctttc caaagcaact ctgcctgttt tctttcctag   58080
cagcagtgtg taagactttc tgttgctcta catcaagatc aaaatttgcc agccttttc   58140 acttctgcca cattagtttg tataaaatgg taattctcta tagtcttaat ttgcatttca   58200
ctgatgacta atgaagttga acgtattttc aagtcatcaa tggccattca ggtctctttt   58260
tccatgaaat gcctgttcat gtctttcacc taattttcta ttgggttttc tgttgctttc   58320
ttagtggttt ttaggagttc tttatatatt taggataata atcatttgtc acttgtgaat   58380
tgcaaatatc tcctcccaat ttgtggctta tcttcctagg ttatttatag tgtctttgga   58440
tgaacagaag atttttattt ttgtgtattt aaattcatca gtcttttttct ttgtgatttc   58500 tacttttgt gttttttaaa gaagttttcc ctatccaaag ttataaaata ttttttgctt   58560
tttttctaga acttataaca ttttacattt tatatttaaa tctttatcca tctgaattg   58620 attttgtgt gtggtggtat aagttaagga tttatttttt tccatggtga taagccactg   58680
tcccagcatc atttattata gttcacgctt tccctgctga tttgcagtgc catctttctc   58740
gcacacccca tttctacaga taagtagatc attttttcagt tccctgtttc tttcattggt   58800
```

```
tggtttggtt gattcctaac cacacggtct aattatcgag gctatttaag tcttgatatc    58860
tgaaacatga agctgtgcca actttgtgct tcatcaagga tgtcttggct attttttgtt    58920
tcattctctc tctctgtctt aatgagatag gatctagctc tgtcacccag gctggagtgc    58980
agtggcacaa tctgggctca ctgcaacctt cgtcttccgg gctcaagcga tctcccacct    59040
cagcctcccg aggagctggg actacagggg cgcaccacca tgcctggcta atctttgcat    59100
tttttttttt ttggtagaga cggggtttca ctatgttact ccaggctggt ctcaaactcc    59160
tgggctccag tgatctgccc gcctcagcct cccaaagtgt gggattaca ggcatgagcc     59220
atcacgctcg gctaattctc tttgttataa attttagagt catctcttta gtttcttga    59280
aaaactttgt tggatggttt tgtattgaat ttatagatca atttggaaga atcgccatct    59340
tatgaaattg tctttccacc catgaaagtg atttatattg ccccatttat ttaggtcttg    59400
aatgtctttc aataattctc tccataaaat cttgtacatc tttttttaga tagatgtccc    59460
taggttcttt attttttgact tctattgcaa atggtacact tttcaaatat tacatttcca    59520
tttcttatat agagaaatgc agtttatttt tgattgcata ttgatcttac attcatactt    59580
cttttttttt tgtgagacgg agtctcactc tgtcacccag gctggagtgc agtggcgcaa    59640
tctcagctca ctccaacctc tgcctccctg gttcaagtga ttctcctgct tcagcctccc    59700
aagtagctgg gactacagac gtgcgccacc atgcccagct aattttttgta tttttttta    59760
gtagagatgg ggtttcacca tgttgaccag gccagtctcg cactcctgac ctcaggtgat    59820
ccacccacct tggcctctcg aagtgctgag attacaggca tgagccaccg tgcctagcct    59880
tatatacata cttctcgata tgcttttctta ttctcatttc tctgtagaat gtttcaggct    59940
ttctgagcag ttaaaggatc tgtgaatatc ctttgcagaa gaaatagttg tttttttcttt   60000
cccacttctt attcttttttc cccatgtttt tttggctggg acctccggta ctgtgttgaa    60060
tagactggtt gtagctggaa tccttgtctt cttttcctga ctttaacagg aatgtttcta    60120
acatttaaac acagaatgaa gattgctttg gggttttggt agaaatgttt ttatcaggct    60180
aaccaaattc cttttagttt ttagtttgct gagaggtttt aagtgggcat taaacttacc    60240
aaatactttt ttctgcaatt attgtgataa ttatttttc cccttttgtc tgctaatggg    60300
atgagtgaca ttttagatt tttaaaaaat taccttaaat tcctgggata aattcaactt     60360
ggtcatgatg attatgatgt ttcctttcct ttctttttttt ttttttttc ttttgagat     60420
agggttttcac cctgttgccc aggctggact atagtggtgt gatcatggtt cactgcaacc    60480
tcgacctcct gggctcaagt gatcctccta cctcagcctc ctgaatagct gggatgcag     60540
gtgcccactg tcatgccttg ctactttgtt tttttttttt ttgtattttt tgtagagaca    60600
gggttttgtc atgttgtcca ggttggtctt gaacccctgg gccaagcga tttacttgtc     60660
tttgcctctc aaagtgctgg gattacaggt gtgagccacc gtgtctggcc agattttaaa    60720
gttctaattt ggtatattta aaggactaaa caactattca ggctttctat ttttttaaaa    60780
atagaaagtt atattttga taagttatat ttgtctaggt atttggccat tttatttatg     60840
tttttaaact cagtgttatg cacttattaa tcatattctc cttgtaatct ctcttattaa    60900
attttcacca ttttatacca ttttaccctg cttagtagct gtttttttttt tttttttttt   60960
gaaacagggt ctcactgtgt cgcccaggct ggagtgcagt ggtgcaatcc tggctcactg    61020
caaccctctg cctcccgggt tcaagtgatt ctcctgcctc agcctcccta gtagctggga    61080
ctacaggcac ctgccatcat gcctggctaa ttttgtatt ttttgtagag acggggtttc     61140
actatgttgg ccaggctggt ctcgaactcc tgacctcaag tgatccaccc gtcttggcct    61200
```

```
cccaaagtgc tgagattaca ggtgtgagcc accgcacctg cctgcttagt agctgttatt   61260
aacccttcag cttacaaatc aggaaacaga ggcttggaga ggggaagtca cttgtccagg   61320
ttaaatagcc agaaagtggc agagtcagga cttaaatgca agtctttctg aattgcaaat   61380
ttgtttctac tgcatcatgc tgcacctcga gggatgggta ggattcagac cgcagagatg   61440
ggaaggaaag gcatgtgta gaggaggcac tgtatgtgca aatgtgtggt gataggcatg   61500
ggaggagaca gggagaggtg tgactgcact aaatcctcca gtgggtgcta gagagagcgg   61560
gagatcaggg tggtgtgggc tcatgcctaa ccgctgagtc ttgctgagag acagagagag   61620
gcaggaaaca tgggctctgc tcctgggatt cactgatgag ttggggagtc aggactgacc   61680
cagggaagtc gggaccaggc taattgctat gtggatagtg gggacaatca gtgctgttag   61740
ttttgagaaa atatgccctt gggcaggagt ggtcagcatt ttggtgagat gggtatggtt   61800
gactgatggt gaggaggaag gggcactgag cctgggcaga ggtgatggtt ggaaactcaa   61860
aaggtgctag gcgcggtggc tcacacctgt aatcccagca cttgaggagg cagaggcagg   61920
cagattgctt gaggttagga gttcaagacc agcctggcta acgtggtgaa accccgtctc   61980
tactaaaaat acaaaaatta gccagggatg gtggcaggca cctgtaatcc cagctacttg   62040
ggaggctgag gcacaagaat tgcttgaacc tgggaggcag aggttgcagt gagccgagat   62100
cactccactg cactgcactc cagcctggca gacagagcaa gactctgtct caaaaaaaaa   62160
aagacaaaaa aaaaaaaacc aaaacgtgtc caggagatga gctgagctgt gcctcagcac   62220
attctctctc tttattcttc tctgccctcc acttgctggt ctgccttcca cttccttctt   62280
ttccaaacag tggaggccag gttttttgtgg tttagaatgg aaagccatgt tgattttggt   62340
ggatccttct atgcaaattt taaatgaagg acttatcact gtgggtaact ggtggcgggg   62400
ctggtgtgaa aaagccagct ggaaccttcc caaggtgttg aatgagccc tgttgtctct   62460
gaaatcctgc ctgcgaaaac cctcagatcc tcctgggcct tgtacgtctg gagctattga   62520
ctcctgtggg tgccagtcgg tgttggccaa attgtttgtc aaataagtgc caggtttttt   62580
catgcccatc aatgcccctt aatcagggaa gcagagagag cagtggggac agcagggtct   62640
cagagtcagg tggattcaag cctgggtttg aatcctagtc cttccattta atgagcaagt   62700
agcttaactc ttctgggcct cagttttctc gtttgcacaa gaggaacaat ggtagtgccc   62760
ctgccatacg gatattctaa ggaataaatg acttaagaat tgtgctgggc actcaatatg   62820
ttagatatgg ctagctctta ttacaggctg tgcttctgta ggaaagaaac ttacttgcta   62880
attgcaaaca gtggaggaaa agtttggggt gctaccacat tgaataactg ggggcctctc   62940
ctcatctgag ggtggtggga atcagggaaa gtgccaccac tgagggaggg ctgaggattt   63000
tcatttccag aagaagaaac tgagacccag agaggtcaag gaacttgagc cagaatttga   63060
attcaggtct ctctgactcc aaacctagtg ttctttttc tgggcctcag ccctccccat   63120
aaagcatcag ctgtccagtg ttactcaca gaagatgttc cacagtcacg atggtgctag   63180
gaagagcctg ggagagtccc aaagtggaga ctttgaaggt gggcctatgg gcaaactggt   63240
ccttaggggt aggggatggg gtgggtagg aagtgtgtct caagtcccac agggggaactc   63300
ataggcaagg agagtaggga cctgtcctct ctgggcccag gaattggagg gtccttttgg   63360
gaacatcatc atcccttcct ttcctggtgg tcttatttgt agaacatctt gtgttattct   63420
taggctcagc tgtcagctgc ccagatgtgg ctctggcttt ccaggcggga cttttttgctt   63480
gtcctcagcc actgtgcact gattgcatgc ctccttgtgg ggctgtgcca gggctgccag   63540
cctttcagga tctctgggat aaaactcttt g attctctgcc accctcattt gctcctttct   63600
```

```
ctgccaggag agctctctgt ggagctgtcg gcccactttc cacaaagagc acgagggctt   63660
ctccatctcg ccagtttctt ctctgagttc tttgagccaa cagaagtccc tcttcttgaa   63720
actgttgcac ttgcctggtg gtgcgttacg gacactcctt ggaatcatct tttcaagctg   63780
ccttttaggt cccagaccca agatcttaca gcagagaagc accaagactc ttgtcagcca   63840
gctgccatgg ctttctggca ctcaggggct tccttccttt cctggaaatg actagtaatg   63900
tcaacagttg cccttgcagg tgctcgctgt gtgccaggca cggggctggg tgctttatat   63960
acattattat atttaatatt tacatcatca tattggattg taacaatttt taccttcact   64020
tgacatgtga gaatggaagt ttggagagag taggtaacat ccccacggtc acatacagag   64080
ctgggaattg atctgaagtc tttccagagc ccatctctca gtgtctacat tgcacagtgt   64140
tctcctgagg atgtttcatg aaacaaacaa gaaaagccct ccgtggcaaa agatgtttat   64200
gaaacattgc tgtttccact cctctcttga agatttaaaa tgcaaacaaa catgccgaaa   64260
gccccgagag gtcttgcagg gaagaaacct gtttgttttt gtttaaacca gaatttcaca   64320
gactccttta aaacacagaa ttcctcttcc tcctcttgct cttcttttta atgggacacc   64380
acttaatcat cttgcatacc tacgattttc tgaaacactt tggcaaccac caaattaggc   64440
cagtcttttc tctttggacc tcagtttccc catctgtaaa attaagggtt tgggcatccc   64500
accacaatgg cataactggt acttgatttg ccatccagct gtaagcaacc agtaatccag   64560
ctaaaatata ggaatcaatt gctttcagac attgaactat aggcagctga agaccgtggt   64620
tcctgagagc agagaagcaa atgaggtgaa gtcatcttca aaccatggca caggaaggtg   64680
gaacccaagc acaatggggc agcctccctg ccctggttgg agtttgagga agttgagctc   64740
atcagggggt ctcctggtga tcctgcattc attctaccag ttagttgctg agtaggaatt   64800
ctaggccagg caccggagag ggttcttgcc gggagggtca tttcagttga gagttgaagg   64860
atgagtatga gttcatcagg caagaaaagt aggggggagga ggagttttgg agggagaagg   64920
acagcatatg tgaaggcaca gggagtgggg gcaggttatc taggccccac tgacagtccc   64980
ccactggacc ctgccagctt agatctgggc agagattggc ttgaaaatgt ggggagggct   65040
ggagttgaat aagcccctca cagcctcacc cagagcagga ggagggacat gcgtacaatc   65100
atgcactgca taatgaagtt ttggtcaaca atggaccacg tataccatgg tggtcctata   65160
agattataat ggagttgaaa aactcctatg acctagtgac attgtagcca tcataatgtc   65220
atcgtgcaat gcattattca cttgtttgtg gtgaagctgg aataaaccta ctgcattgtc   65280
agttgtaaaa aagtctagca catacaatta tgtgcagtac ataatagtta atgatgactg   65340
tgttactggt ttatgtattt aatatactat taatcattat tttagagtgt acttattttt   65400
taaaagtta actgtaaaac agcctctggc aggtccttca ggaagtgtcc cagaagaagg   65460
caccattttc tttctttctt tttttattgt actttaagtt ctagggtaca tgtgcacaat   65520
gtgcaggttt gttacatatg tatacatgtg ccatgttggt gtgctacacc cattaacttg   65580
tcatttacat taggtatatc tcctaatgct atccttcccc cctcccctca tcccatgaca   65640
ggccccggtg tgtgatgttc cccgccctgt gtccaagtgt tctcattgtt caattcccac   65700
ctatgagtga gaacatgtga tgtttggttt tctgtccttg caacagtttg ctcagaatga   65760
tagtttccag cttcatccat gtccctacaa aggacatgga ctcatccttt tttatggctg   65820
catagtattc catagtgtgt atgtgccaca ttttcttaat ccagtctatc actgatggac   65880
atttgggttg gttccaagtc ttagaaggca acgttttcat aggtgatgac ggctacgtgt   65940
gtgttattgc ccctaaagac ctcccagtgg gacaagatgt ggaggtggaa gacagcgata   66000
```

```
ctgatgatcc tgaccctgtg caggcctagg ctaatgtgta tgtgtgtgtg tgtgtgtgtg    66060
tgtgtgtgtg tgtcttagtt tttaacaaaa aaaatttaaa aaacgaaaaa aaattttaaa    66120
tagaaaaaag tatagaataa agatagaaaa tattttgta tagctgtact atgtgcatgt     66180
cattacaaaa gtcaaaaaat tcaaattaaa acatttcagt aagctaaggt taatttatta    66240
ttcaagaagg aaaactattt ttaaataagt gtattgtagc ctaagcatac agtgtttata    66300
aagctcacag tagcgtacag gaatgtccta ggccttcata ttcacttacc agtcactcag    66360
tgactcaccc aggacagctt ccagtcctgc agcttcattc atggtaaatg ccttatacag    66420
gtgtatcatt tattatgatt tttttttctt tttttgaga cagagtctcg cactgtcacc     66480
tgggctggag tgcagtggcg cgatcttggc tcactgcaac ctctgcctcc caggttcaag    66540
tgattctcct gcctcagcct cccaagtagc tgggattaca ggctcgtgcc atcatacca    66600 gctaattttt tgtatttta gtagagacgg ggtttcacca tgttggccag gttggtcttg    66660
aactcctgac ctcatgattc acccacctcg gcctcccaaa tttctgggat tacaggtttg    66720
agccaccaca cccggcccat ttattatttt tatagcgtat ttttagtgtg cattttctat    66780
gttaagatac ataaatactt accattgtgt tataattgcc tacagtattc agtacaggtt    66840
tgtagcgtag gagcaatagg ctatgccgtg cagcccaggt ccatggagta ggctctacta    66900
tctgagtttg tgtaaataca ctctgtggtg ttcgcacaaa gaccaaatca cctaacaatg    66960 cattttcgg aatgcatccc tgttgttaag cgatgcataa gtattaaatg agtgagtggg    67020
cgtgcgtgtc ccaaggcggg tgtggctatt ttctcagtcc caggacctga tctccaagac    67080
cagagtggga cgtccttggg aatgctgaac agaacagccg gggacggggt ggtcctgggg    67140
gctcggggga ggatggtttc ccagggtgtg tgaggagctg tggacctctc cacccactcc    67200
cccactggct gcggccccgc acaggctgac ggtggaactg cctgcgcagg agaaaggcgc    67260
ctattcgggt gcctggtgtt aatctgcaga ggggttggca gcagctgcta atttctgatt    67320
tgcctgtctt tgaatggggg taattgctgg gagttgccag tgttccaggt tgttctctgg    67380 aagagggga ggaagaagca gctgtcatgg gctctgcgga gtgctgcctt ctgcaggtag    67440
catggtgaag cctcgctgga tagagtgagg ggataatgaa atctagccag gcagggccgc    67500
aagggccctc ggaggccacc tgatctgacc ggctcattct acaggtggaa ccgagatttg    67560
gagggaggga atgtgttcag gaccacacag ggtgggcctg gctaggctgc ttggctccag    67620
ccaacaaccc agctatgctt ggcattggct gtgcctcccc accccatag accccagtct     67680 ctccaggacc cccgaggctg gggcatgtgt gtcaagaacc cttttgtctt tctctgactg    67740
caggagacca gcgcagcggt ggggtcactg aggccagcag cctcctgggg ggctccccga    67800
ggcgtccctg tggccggaag ggctccccat accacacggg gcagctgcac cctgcggtgc    67860
gtgtcgcaga ccttctgcag cacatcaacc agatgaagac ggccgagggt tacggcttca    67920
agcaggagta tgaggtgcac gccggccccg ggccagcagg atccctgcag aggcctcacc    67980
tggctcttac tctctgtgga ctctgaccct ggcaaccctc agcctagtcc tggttggacg    68040
cctgctctga cagtttccaa ctcaaccttt ttgacctcga ctctgaccct catcctaatt    68100
ttagactgat ttggttttc actctcatgc taaccctgat ttgaaatctg accttgaatc    68160
tcgtctccat ctctatgtgg actgtgatcg ggatccttat tctgtcccta aactgaatct    68220
gcccactgac actgaccttg acctaatccc agcctgacat tgatcctgac tgtcatccta    68280
agctccattt gaactctgga tctcatccca cctctgtctg gactctgaca tcacccttat    68340
cctaatctaa atctgacctc accttaccct tctttctaac cgttattcta agcctgaccc    68400
```

```
ttattccaaa atgtctttga accctggccc tcttttcctc ttttctcatt tcccttcccc  68460
ccacatgcct tggttttgac cctggtccct ggctgataaa aggacccaca gtgacacagt  68520
gactttatct caggcccaag ttcagcttga atctggccct tatcatccca cccccatcct  68580
gcctacatca tccccactga ggggaagggg ccctcagtga gggtccctct ctcccactga  68640
ccaccacttt tctttctggt agagcttctt tgaaggctgg gacgccacaa agaagaaaga  68700
caaggtcaag ggcagccggc aggagccaat ggctgcctgt gagtcctggg gaagggcctg  68760
gggtccaggg cagtgggtgg gagggcatca ggagggggaa cacagccagg gtgagctggg  68820
gcagcctcag agatgatagt agcattggcc accttttatt gagggcctac cacacgtcac  68880
gccctgtgct tgtttcattt attcccttca atttccctgt gaaacgggaa atactataat  68940
ccctgtttta caaataagga aactgaggct tgggagatta agattcctgc ttaaggtctc  69000
agagccagta attgcctgag cagcatacac tcttaggcct ccttgactcc atagcccagg  69060
ctctaccccc tggtgtgtcc tgcctcccat ggtgcccaga gactactggt aagccctgag  69120
actctaggtt ccctggctgc cctgcctgtg ccctatcccc tagcctccag gaatccctcc  69180
ctgactgcct agctctgggc tccccagttc agccctgcc cacctgctct gtgtttacag  69240
atgatcggca ccgagtgaaa ctgcacccga tgctgggaga ccccaatgcc gactacatta  69300
atgccaacta catagatgtg agtgccttgc cctgtcattt ctgcagacct ggccctgccc  69360
gctccaggct tactatccag gcagggcaga aacctgtcgg gataaatggg ggttcaaatg  69420
gctgagttcg gagtgcccct atctctgcag tcagtgccag ggagctcaga ggagggagga  69480
cagtgagcag cagcttctgg aaggctttct gtaggtggga gttggcctga gagatgaggt  69540
gctttagaga agcaaagcaa agggaagagg cagacagcta ggccaagagg tgaggaaggc  69600
gggaggcatg gagaatggga ttctcatcgt gcaccatgag gctgaagagg taggcagggg  69660
ctggattgtg aagacctcaa atggcaggct caggagtggg ggcttttcc taggggcacc  69720
agggagttgt taaagtgttt tgaccatgat cagagtggtc ctttaagaat aataacgcac  69780
atttatccag cacgtactga gtgccaagca ctgtgctaag cactttacac ccaagatctc  69840
cttttctgta atccctccac ccaccctttg aggcagttag caccatgacc tcactttaca  69900
ggtgaggaaa ccggggctca gagcgtggaa gcgacttgtc ccaggttgca cagctagtga  69960
gtggtaaaga aaggacgcaa atctcagcct gtctgtgtct ctaaagcctt tgctgctgtg  70020
aggctgtcct gccccctgct gcagcagcag caggacttgg atggattgga gggagggggcc  70080
agagacagag caggcagcca ggaggcctgg gcttgggtgt caaagagagg tgatgagtct  70140
acttcctagg tgtggaagag gggcgaggcg ggacagggcc cctaatccct acagcaaacc  70200
aagtttggga gagcatcatt taatcacgta tgaaatatat tttgagcact tcctttgtgc  70260
catgcattgt gctgggcacc agggatacag atgtgaacaa gacagtcatg gcctctgctt  70320
tccttgaaca tatctatttg agtgggtgag acagatagac atgtttacaa atcaaaataa  70380
cttcagatta gatgagcaag tgcaggccag gagagagatc acacagcttg agtgttacac  70440
agcaggctag tggcagagcc agggctggtg tggcgggctt tgtggaggaa gcagggcttg  70500
agctgcctct gggtggctgg agaggagagg gaagagtgtc ccgggtgagg agctgcctaa  70560
gcaaaggcct gggggggccag gcagagcaag gcacaggtct gggagccgag gtagtcaggg  70620
tctctggagg tggcctctcc tctccctctt cttctcctcc tctgggccc agatgtgcca  70680
tgccatgttt cccagaatcc cttgctgcct ccccactca tcctgtccct tggttggagt  70740
cagggccagg cccagcctgg aagacttggg cagctttggt gacagcgggc ctctccttgg  70800
```

```
tcttgccaag gtcccagttg gctcctcttg ggccctggca gggacatgcc actccccact   70860
ctgtggctca gcccagcccg gcctgcccgt ctccgctctg cctgccctgc tcacatcgcc   70920
cattctggcc actcctgtgc tccgtccacc tccatctgcc cctggcctaa tatctgtctc   70980
ttttgctttg tactgtttcc tcactggaat cattaagatt cggataaacc gagaagtaag   71040
tatctctctc cccttctcct cctcctcctc ttcctcctgt ctgtctgact ggctgtatct   71100
cagactctct cacggtctct ggctgtctgt ctctctgtct ctgtccttcc tttctactta   71160
tgtgcccagc accaaccgtc catttcagca gcctggccag gggctgccca gggctgaaga   71220
ttcgagagtg ttcctattgt aagcagttcc ctcccatcct ccactgcctt gagcaggggc   71280
agcagtgttg ggggtgcttc ccctgcccat tctgcactgg tcacaacagt ctgtcacctt   71340
ccttccctgg ctccgccatt cccaaggagt cctccctagc ctccctagct gcaccttcta   71400
caggaccctt tggagggtgc aggggaagct gccctggagg gccctgtttc tgctgcttaa   71460
gggtcaagat cttggacagc cccaggtcag cctcctaaaa ctactttccc tagtgttcaa   71520
ataccttcat gatcagtttg cctgaaactc aaccccgacc attttaccct caatttagcc   71580
ttaatttgaa tgttttttgg tggaagcagt ttggatagtc tgttttaaa tattatgctt    71640
tttttttttt tttttttttt tttttgagg tggagtttcg ctcttgttgc ccaggctgga    71700
gcgcagtggc acgatctcgg ctcactgcaa cctctgcctc ctgggttcaa gtgattctcc   71760
tgcctcagcc tcccaagtag ctggaattac aggcatgcac caccacgccc agctaatttt   71820
tgtatttta gtagagatgg ggtttcacca tgttaggctg gtctcaaact cctgaccta    71880
ggtgatccac ctgccttggc ctcccaaagt gctgggatta caggcatgag ccaccacacc   71940
tggcccattt tttagccttt taaaattaaa aaaactaccc taattcatct agctattctc   72000
taatttgatt tcttttttct tttttttga caggttct tgctctggag tgcagggtg     72060
tgatcatggc tcactgcagc cttgaagtcc tatgcacaag caatccttct acctcagcct   72120
cctgagtagc tgggactaca ggcgtgtgct gccatgcccg gctaattttt tccttttttt   72180
ttttttttta agagatgggg tcttctcagc actttgggag gccaaggcag gcagattgct   72240
tgagtccagg agttcgagat cagcgtgggc aacatagtga gattgcctct acaaaaaata   72300
caaaaattag ctgggcgtgg tggctcatgc ctgtagtccc agctactagg gaggctgaag   72360
tgggagggtt gcttaagcct gggaggcaga agttgcagtg agtcgagatc gtgccattgc   72420
actccagact gaccaacaga gccagtccct gtctcaaaaa aaaaaaaaaa aaaagagag    72480
agagagatgg ggtctcacta tgttgcctag gctgggatt tttaatacat atatactgtt    72540
ttcataatat ttaatgactg gtgattattt gctattttgt gggtgctttt tccattttgt   72600
ctcctttttc ttttaaaaaa tatatttctt ggctgggtgc agtggctcac acctgtaatc   72660
tcagtacttt gggaggctga ggcgggagga ttgcttgagc ccaggagtta gaccagcctg   72720
ggtaacatag tgagacccca tttctacaaa caaaccaaca aacaaaaatt agttggatgt   72780
agtggcctgt gcctgtagtc ccagctactt gggaggttga ggtgggagga ttgcttgagc   72840
actgagggtc gaggctgcag tggagacagt ggcatggagc gacagcagga gggaattggg   72900
ctagacgtgg agaagttcca gtgctgaggg ctgagagtca ctgggaggct tttcgtcatt   72960
agtcactttg actatgtttt ggtcattttc gtgggaacag tgagcaggta tccagcagaa   73020
tctctgagtg tttgtcttgc tattatcctc atattgcaga ggagaacaaa ggcttagaga   73080
ggccaagagc ctggctactc aggatgtttt gaggccagca atatggacac cacctgggag   73140
ctggtgatgc ataatcccgg gccccacccc agacctttga atctgaatct gccttttaac   73200
```

```
aagatccccc gggagattta tgtctcaaga aagactgaga agcaccttct cagcgctcag    73260
agttacacag ctactgctcg gcatagctgt ggcaggacc caggtccatt caactccaag    73320
actcagattc ttcaccccat agtcaatcgc cttctgcccc agcaattctt gacttccatt   73380
tgatacactt gattcatttg tatcttcaag gatactgctt cagctttaaa atagtagtag   73440
taataataat ggctattact gaataagtac tgactttgtg ctagacacag tggcagacat   73500
ttaacatact actttatttg cttctcacaa cagccctcag aggtaaatgc tgtaattatt   73560
ccattttata gacatgaaaa tggaggcata gagaaatgaa ggagttttg ctcaaaggca    73620 cacagctagt gagaggtaga gctgggattt gaaccttggc agtctggccc ctgggctcct   73680
caggcctggg aagttcacga gaccggagga gttgctggga gctgtgttga gggtgtaaac   73740
ttgaggtagg gggctgggct agttttctca gcgccagccc tgcagtacta attcccttt    73800 ccgcattgcc cgcattgatg cccttggtat ctggtgaatt cttttgctca gaaagatgag   73860
gccttgtggc aggacctcat gggtggctgt ggccctgggg tggcttgtcg gagggcaggt   73920
ttctctcctc agcttggggg ctctggggat ggaggatgaa gtagctcttg gcctctctct   73980
cgtgggaggt ggtactggta aagtgcttag cacagtacgt gaccataaca gggtcattat   74040
tattgatctt aaagatttta acattttatc caagggccat gagtaatgtc tgtgcccata   74100
tacttccatc ctgaagccct catctaggcc ccccacgctc tgagtgactg aggagtaagg   74160
gggaggggta ctgtccattc tggttatccc aagtgtgggg gctaagataa ctgacaagct   74220
ctggttatcc cacgtgtggg atctgggttg attagagctt ctggaaccct gggaacaggg   74280
cagggccatt ggggactctg tctccgaaca acagcctggc tgaaagcaga tgcctctctc   74340
cactttatgg gtgggggtc cctctaggca cataaaggag tcatgtcctc cctggggttg    74400
cacagcccag gttggattaa gcccacgact ctggtgtccc agctgtactt ctccacttcc   74460
ttggggacct gggggatgc aaagtcatcc tgcttaggag gtcctaggga tgtgagggag    74520
cagttccctg gtgggtagg ggttctgctg ctggagggg agggtagagg aggtgtgggg     74580
gagtgagggg ctactccctg gggtctaacc gtgccctctc ctcctgttcc agggttacca   74640
caggtcaaac cacttcatag ccactcaagg tacctggcac ttctgcccac atgcgccttc   74700
ccatgtgcct cccagcgtgc tggaatgccc tcagcttgcc tttctgcctc ccctgctgat   74760
ccgcttgatt cctgaatgtc tccccaccgt cgccatattc tggctccctg cttgttcatc   74820
tgctcccgat tctgctggat ctcttggaat ctggccaact gcctttgtcc cctctttgtg   74880
tttgtgtctc cctgatgtgc tcagtccatc tgttgctcct ggtctacctg cctgtctcca   74940
aagtggtgtc tgtaaaaggg ccagctgggc tcaggcctca tgggtgtggg ttgggcctct   75000
cggtctggtg gctgcctgga ttcttctgtt tgcatccctt tccacgactg tccatctgtc   75060
tgtccctcct ggacactcat gccattgccc aaccatctgg tcctcctcca gggtcccatt   75120
caggatgagc gggctcttta gccaggccct tcctgatgc tacccaacct cagggcccta    75180
caggcatgcg tcagctgcaa gctgggtgtt gtgggcagca tgaagccccc gttggggctc   75240
aggaggcctc ctggcctggg gtgtggtgct ggatggtgct ggatgtgctg acctggggtg   75300
gagaccttgt ctcagggaca ggcaccctct gcctgcatcc ccagggccga agcctgagat   75360
ggtctatgac ttctggcgta tggtgtggca ggagcactgt tccagcatcg tcatgatcac   75420
caagctggtc gaggtgggca gggtaagccg ggctgtgggg cgagctgggg cgcatggcag   75480 gccaagggg cagcaaagag cccactgagt cccgtcctgt ggggcctcta ggtgaaatgc    75540
tcacggtact ggccggagga ctcagacacc tacggggaca tcaagattat gctggtgaag   75600
```

```
acagagaccc tggctgagta tgtcgtgcgc acttttgccc tggagcgggt gagtctcccc   75660
accgcctgtt ccctgcagag ggtgcctgag cagggattag agcccactcc cacttccccc   75720
agccctggga gcaggagggt gaggagcgca ccactgccca tcccagcaag gaagctactt   75780
ggtcactgtt ggctgggagc actctagaag ggcaggaagg tcactgcctt tgttggtgcc   75840
cataggagga agctgagaca atgaagggg tgacagtatc tgccaggtgc tggctcctac   75900
tctgtgctga gcctgttata aatattgttt cagtcctgga aagctccgtg tgattagccc   75960
agatacagaa agtgaggctc agagggctta tgccaggcag gagaggccac atagtcagtg   76020
gctggccagc gagtcctgtc cacgatccca tttgatctgc tctgtaaagt cctcagagga   76080
aagatagttt ttttccttt aaattaagac cctgggagtc aaaatgatat atgtttacac    76140
aacaacctgg tggcagaggt gagtatttca gcccaggt ttaggcatca ggcagaccat     76200
tgtccaaatc ctgcatgttg ttggtttctc taaccttggg aaagtggttt ctcctctttg   76260
agccttagtt ttcttgtttg tacaatggga cattaatacc tacttcatca gtaaattgat   76320
cattgggatt agttgagatt atacaatgag atgcttactg cagtgcctgg cacacagcag   76380
gtgtctaatg gtgacagatg ctgccaggga ctctgattat tattcccatt gtctccccag   76440
agaggctact ctgcccggca cgaggtccgc cagttccact tcacagcgtg gccagagcat   76500
ggcgtcccct accatgccac ggggctgctg gctttcatcc ggcgcgtgaa ggcctccacc   76560
ccacctgatg ccgggcccat tgtcatccac tgcaggtggg ggcaccggga atcccaagga   76620 gaaaggggc ccttctccct gggaatttgg gcttggggtc aggttggttc aggatctgta    76680
gtggggacca ggcctgggtt ctcctgctta gagatggagt gcaggaggga acgaccccca   76740
aaggccctgt cccctttggc ctttggctct gaggttggca tcttcatgtg cccccaaga    76800 cctgtgaagc cccttgaccc aggtgctgag gaggcactgg agatagggag gggcctccgg   76860
gccgctgagg cgccaggcac gattgagttc tgcctgcttt cagtaagcag ctttttgttg   76920
cacacctgcc gcgtgctagg cctggcctgg gggtgggaag gacttcactt ctctccacca   76980
aacccagtgg gccttgccta ccccttggcc ttcacacctt ctgcagaccc tgactggctc   77040
ccgtgacccc agctgcccct cctctctctg ctttctccct ggctccacat cttttctcttg   77100 cttcttaaat ggggacccag tacgctgtcc tggcctgccc tctgtctccc cctggagagc   77160
gtaaccccca acctttgtgg ctttgtccat ggcctctgtg tctcattgcg gttcctctac   77220
tgtgttctta tcagctcccc aaatgccgca tggtagagtc gtcctccctg ccctgccacc   77280
taaaccagct tctctttgat ttcttaggc ctctttaaga tgccatcttt taaaaacaaa    77340
actttattga tatataatac acttaaagca aagtgcagaa atatgtttaa aaatatgaat   77400
tttcataaac tgagcacact tgtgaaaaaa ccagctctac tgagattaag aaacagaaca   77460
ttggctgggc acaggggctc atgcctgtaa tctcagcact ttgggaagcc aaggtgggag   77520
gatcatttga ggcccaaagt tcgagaccag cctgggcaac atagtgagac ctcattgcta   77580 caaaataaa aaattagtg ggtgtggtg gcacaagcct gtagtcccag ctacctgtga      77640
ggctgaggtg ggaagtttgt ttgagtatgg gagttccagg ttacagtaaa ctgtaattgc   77700
accactgtac tccagcctgg gcaacagagc gagactctgc ctctaaaaaa aatttttttt   77760
ttaaagttaa gaaaggagca gaacatgaac agttcccaga agccccttg aacccgtttc    77820 tggcctgaat tcccccatcc ccagtcccag agaaatcact attctgactt ctaaagcgca   77880
gttagttgca catgttttg gacttgtcat aaatggaatc atacagcatg tgctctttgc    77940
tgtttgtctt ctttccctga gccttaggtt tgtgaggctc gtccacagtg gatcatcgtc   78000
```

```
catcaagtga ataaatgaca gtgtgtttgt ccattctgcc atgataggca tttgggttgt    78060
ttccagtctt aagctattat gagtagtgct gctaaggaca ttcgatcgta tgtcttttgg    78120
ccaagaaatg tatttctttc tgtgtggtat gtacgtagga gtagaactgt tatctgtgtg    78180
aacgttcagc tttaggagat attgctgagc agttttacaa gggggttgtg ctaagttaag    78240
ccccaccagg ggtatttggg gtattcagtt gctgtatgtc ctcgctagca cgtggatgcc    78300
actgttttca aacctgaaat cttgctgtca tctttgtcca ctctccttcc ccctcagctc    78360
tgcacaacct tgcgtgagga caatgatctt gatgtgcccc cagtcaagtt agggagacag    78420
ccacataaac aatgaccatg tagcaggaag agtgttttat tgaattaatt aattttttt    78480 ttttgagaca ggatcttgtt ctgtcatcca ggctggagtg cagtggtgtg gtcttggttc    78540
actgcaacct ccatctcccg ggttcaagcg attcttctgc ctcagcctcc tgagtagctg    78600
gaattacagg cacgtgccac cacacccggc tattttttgt attttttggt agagacaggg    78660
tttcactatg ttggccaggc tggtctcgaa ctcctgacct caagtgatcc acccacttcg    78720
gcctcccaga gtgctgggat tacaggcctg agccaccgtg cctggccacg aagagtgttt    78780
taataaaaac ctgcccacgt tgcttttggga actcaaaaga atgacatcat cctggaaggg    78840
tcagggatgc tccagtgggt atgtgaatgg gtatgagtgt gtgggctttt caaggatgtg    78900
taggagattt ggtggttttc aggaggaaag aacattcttg aattagctcg gaggatcatc    78960
attcctgttc tctcctaatc ttaagttgct aggttgagcc agtgtcacct ttgcattctc    79020
cccaccctct ctcctctcct tccctgaggc ccatcccatc tctgtcctct agcacatttc    79080
actagagctc ttccatccag cagcctgcgt cctggctcct tactcgggga ggggcagtca    79140
tctctgtgtc cgtgtcccct gtatggtgta gacatggcca gtgccctcct ctcttcttct    79200
ccttagtccc gggcttcctc cccaaagctc tgacctggtc tggggctgct ctctctccag    79260
cgcgggcacc ggccgcacag gttgctatat cgtcctggat gtgatgctgg acatggcaga    79320
gtgtgagggc gtcgtggaca tttacaactg tgtgaagact ctctgctccc ggcgtgtcaa    79380
catgatccag actgaggtgc ggggacctgg ccctgtcccc accattatta cttctaggac    79440 tggagttct cgtgaaggat cctggagccg gcagagcatg cccaaggggt gtcctgaggc    79500
tcttgccttc cctcagatca tccctgacct tgggccgcca actgcatagg gtcatcctga    79560
actgctcccc tgtgttctgt tgggtggggt cagacaaccg gtcctgtagc tgacatacct    79620
gggattgcat cctcagtgga tgtgtgaccg tgagctgtcc cccacctctc agagcactca    79680
cagagttgtt atagggggta gggatgaaat aggagataaa ggggcatgtc catggaggtt    79740
gtttcaggta ggcttggtcc agcctgtagt aacatggttg gcctccacct caggacaccc    79800
tgcttcaacc ttgagcttgc ttaagcccca tcaccacaga tctccagctt ctaggcccct    79860
cctcggcctc attctcatct cctgttccag gagcagtaca tcttcattca tgatgcaatc    79920
ctggaggcct gcctgtgtgg ggagaccacc atccctgtca gtgagttcaa ggccacctac    79980
aaggagatga tccgcattga tcctcagagt aattcctccc agctgcggga agagttccag    80040
gtgggggatg agtgcgtgtg tataggtgtg tgtgtgtgtg tctgtgtgtg tgttgggca    80100 tccttaatac tgcaggagtc attgagggcc aagaagcagg gaccagcctg aggccacagc    80160
tggagggaca gagctgagct accaggaagg actttgggac agcggaagat ggggtgcatc    80220
aaagcagtta agagcccagg ctttgaagtc agataaaccc aggttcaaat cctggcttac    80280
ctagttaaga gctgtgagta tccttgaaca gttcccttta cctctctgag cctcagtttt    80340
gttacccaga gaagagaagt agttaatatg tccctgggg tgtttgtatt cattgggatt    80400
```

```
cttttggttg tgagtgatga aaatccagct tttataactg aaaagtctga ggatcgtgca   80460
gcttcagttg tagctggatc caggggctca gatgatgatg ccaacaggtg gtttctgtct   80520
gccttggttc tgctctccta ttttttggctt cattctcaga cctgcacctg ccgccagca   80580 gtgctgggct cccatcatct ctattgtctg gtgacttagg aaaaaggcgc ttgctgctcc   80640
cagcatcccc ccaacagtcc tagatcagac tttcatgttc ccatccctgg accagtcaca   80700
ggttggagag gtggagctca ctgattgccc ctggctctgg tcacatgccc aaggcctggc   80760
tcttggggca ggaccagcct caccatatca catggctgag atgggaaaag gctggttctc   80820
cagagaagcc tgagagcgat cactgggtgg cagagacctc agaagtcccc tccactccag   80880
ggttcctgca gtggctcagc aggatggcac gtgctgggga cctggcactt ctcacaggag   80940
gtgcagggtt cccggaggag ggtgtcaggc tttggggatc atgatagact gtggttccct   81000
gtgagggatc tccaagaaca agagaaagaa actgagagcc cctgggtctg gatgcgtgag   81060
gtgtgaaggc atgcgggcgg aggagatgcc ccggagatcc aggtgtgatt cagtgcccgg   81120
tgcttaggac ttcattctgt tcagacaggg ccgtgaccaa ggaacgtgac cccctctcca   81180
cgtgcctgga gtccgcttct tggagggtgt gggdgtttcag gggttgcctc agtgaaggca   81240
ctggtcagct agtaaagttc ctcactgtgc ccgtgtgtgc cgagctcagc ccagtgcttg   81300
tcatgatctc actttggcct cccagcagcc ccatgaagta ggcatattac ttccctattt   81360
cacagtcgag gaaactgagg ctgagagatg cagtagcttg tctgaggtta tgtgggtggc   81420
aaggaggtag actctggtct ctagagctct atccaggccc tataatggcc tagagacagg   81480
gagtctggct ccgtgccctg tacccttctc tctggacctc agtttctcca tccataaaat   81540
gggattagta actcagtcca gcctccttca tggggatgtg aggaggccca gcaagccctg   81600
gacgtaactc tctgtcccca cccccgctcc ctgtagacgc tgaactcggt caccccgccg   81660
ctggacgtgg aggagtgcag catcgccctg ttgccccgga accgcgacaa gaaccgcagc   81720
atggacgtcc tgccgcccga ccgctgcctg cccttcctca tctccactga tgggactcc   81780 aacaactaca ttaatgcagc cctgactgac gtgagagctt ggggtggagt gggctctggg   81840 gctcccctte ccagcagcat cagggaaggt ccagggccca cgggaacaaa gctgaaggct   81900
ctgttggggg gacccctgcc cattctgggg aacaggcctg tgtgtgaccc tcctactcct   81960
agggagcttc cattcagggc attcaagcca gtgcccccca cactctgcct cagtgggtc   82020 tggttgtgga gttcaggcag ggctgtctcc aagattaggc ccagcagagc ctggggtagg   82080
atgagtgatt caggggactt tggctgggga gacctcgagg gtttgggat ggaactcgag   82140 acctgatgtc tggaagcagg ggagcttgtc ctggggagaa tgagctggag tctgctccag   82200
gaccaggcct gggacagtga tctctggccc cattcttccc tgggtgggca tgggccctct   82260
gagggctcag gagcctttta gaagtctctt tccctgcttc aagctcaggg gctctgcctc   82320
ctttactgag ggttgcaagc agctcaggag atgggtgctg gcattttagt ccctgctaa   82380 atggctccaa gatgctgctg tctgaggcgg gaagggtcta ggattattat ccctattcct   82440
ctgccacact ggaaccagtt cagatataga cacaggagac acgggtgg agatcatatg   82500 ttatagataa aactggagat ggagtttgag atgtgtggcc agttggtggg ccgctccttc   82560
acccctcccc gatatagccg tgcaaccgca ggccacccct cccgtcagg actggcctt   82620 tactggcagg gagcaggagc aattgagtgc acactttcca agggtaggct ggcctggaaa   82680
aagaggaagg agtggagcca agcagcctcg ctcatgggag gagtgagtga aggatgggcc   82740
agggccaggt gtgtcactgc tgcgtctctc cacgcggaaa tgagggatgc cgatgggaa   82800
```

```
ggttctccca cagcggttaa gagggagatg ggcttttgc ggcctgatgc ctggccagga   82860
actccttggc aggacagtgc gggggacagc ggggtttctt taaagagggt aaccacccag   82920
ggggcttccg ggtgtcagct gaaggggagg ggaagagctg ccctagccac tgatgagaga   82980 tgtgagggggc ccatcagtca ctgtcactca gcttggtgga tggaatgtgt gtgcccacat   83040
gctcgccggg ggacatctgg cctgctgagg ggtcaggggt cctggagggg tggcatgtag   83100
taccgggaag atctttgaac taaacttagg aagctgtgcc ctcccgccca gcccctcct    83160 tggccttggt gtgcccatct gcacattggg ggcctggaaa ggagactgtc tgagggtcct   83220
gagctggggc tccctggccc tgatgggtgg gttatcacgt ggaaaagttc tgagacagcc   83280 ctgtccctc ctgaggtcct tgatgcctct gacgtctgac cccagccatg caggtcctat     83340
tggcttggag ccaggaggcc ccatttctca gacaggccct gaactcgtca gtgagggggcc  83400 agctggagtc tttgtggtgg tcaagtctgc aaggagccct gttgggcacc caggcctgag   83460
ttttggaatc tggctgggcc tggccttgag gagttgttaa tcaggagcct tcagagagtc   83520
ctggagagag atcgctgggg gaccaggggg gctctttgtt tctctgcact gcaccttgca   83580
ggattacaaa gggcagatca atatttggtt agggcccaag tcagggtcaa ggccagaaga   83640
agccagacaa agaccagggt catgggagct tgtgccagcc cctaggtcag gaggaagact   83700
gggggacagg agaagagctc ggggaaggga gggggggacat ggcacagggt ggggcagggc  83760
aggtcaccag gggaggctgg gagctagatc tttaatggga aaggccgggg tgccagcccc   83820
cctggcagga cgagggagca gtgagcagcg tcggggcctg tcactgcctg gagagcctgg   83880
ggccccagac ccttcactta tggagttgga agggacctag agatttattc aaaatattta   83940
ttgagcccct acagggttct gggtggagac catacccctag aagctctgct ctcctgaacc   84000 ttgctttttag caggtggagt gggatagtca ggaaatatac aatgaaatgt catcaactgg   84060
aaatttctac aaaaacagcc aggcagtgtt taatgtggat ttgggtgtg tgtgggcta     84120 tttttgatga ggtggtgggg gagggcttct ttgaggaggt gataagtaaa gaccagaagg   84180
aagtgaggga gacagccata tagacatttg ggaaatttgg cctaggcagc caaaatagca   84240
gatgccgaag cgcggaggca gggagtaagc tcggccagcc tctgccttga gctcagcctc   84300
atgcccaagc tcccctcgcc atacctttgg aaacttttgc tgtttagttc tggggggtca   84360
tgggcttggt cccagaggc ctgggcccac cctgtcaacc caggcctcag tgtgccaacc    84420
aacatcagaa atggcccact ggaggcagcc tggtcctgtg gggcacaacc gtccaactca   84480
gggtgggcag tgcgggaaga cagcctgggg cagaggctca gcccaggcca ggggccggga   84540
acagggccct gctgagttcc ggtttccctg cagagctaca cacggagtgc ggccttcatc   84600
gtgaccctgc acccgctgca gagcaccacg cccgacttct ggcggctggt ctacgattac   84660
gggtgcacct ccatcgtcat gctcaaccag ctgaccagt ccaactccgc ctgggtgagg    84720
cctccactgg ccaggccaat gggccgcctg ctcccaggtc tctgtgtat tcagggccat    84780 ggtccccaaa gccaaaagtt gggtcccagc tctgccatct atttattgtg tgatgaatca   84840
tacaccttcc cagagcctca gtttcttcat ctgtaaaaca agggtgtcag atgggagatc   84900
actagttgct cttttctttt tctttttttt gagacaaggt ctcactcttt tgcccaggct   84960
ggagtgcagt ggcgcgatca cagctcacta agttgtgcag cctcgacctc ttgggcccaa   85020
gccatccttc cacctcagcc tatcgagtag ctgggactac aggctgcatc accacagctg   85080
tctgattttt tttttttttt ttttttttca gtagagacaa ggtctcactg tgttgcctgg   85140
actggtctcg aacacctggc ctcaagtgat cctcccacct tggtctccca aagaactggg   85200
```

```
attataggca tgagccactg cctctggcca cagttgctct ttattggccc cctgctaagc   85260
cagggactgc tttgcactca tggtcttatt tagaatctat aatgaccttg gagggaaggc   85320
ttcagtgaga aaattaagac ccaaagaggt tcagtgcctt ctccagggcc acatggctgg   85380
ggaggggcag agctgtgctc cccagcctca gctgcctcat tccagagctt ctgctctttt   85440
agtcactcca ctaaagcgcc catcatgggg gcctccgagg tagagtacaa ttcaagcctc   85500
ctactttctg actgtttgat ctagggtaag ttgattgacc tcttttgagt tttactttcc   85560
ttctctgtaa aatgggggcc atcataggac ctgttcttgt ggggttattg tgaggaccag   85620
gtcaggtgtg cataggatat gtggcactgc tgtgtctgct gcacagtagg catgtggtat   85680
gtggcaggga caaagatgat gagggtgaca gttgtatctg agattggccc agacactggt   85740
tcagtgacct cagcctgggg gcagcccctc tgactcccct gtttcccttt ggagctccca   85800
agaagtacag atacccagcc ttccagccct gcctgaccat gtgctttagg tctctggacc   85860
ccttcccacc ccagctttct gctgggccca ggggctagg aagatttgct gtaaaatgag   85920
tacaacagct tcttaatggc ctccttgaga agattgcatt aactgggctc tttatgagtc   85980
aggcactttg tgaaaatgac ccaggactac aggataatgg gcctcagccc tggtgcagca   86040
ggaaccatcc ttgctagggt agaggggaga ggcccagagg gaggctcaca gagatgtagt   86100
tcactgggca ctgatttgct catctgctca accaactttg cccatgaaca gctccctgca   86160
gtgggcaggg aggagacaga gggagaagag acacagcccc tcccagatct catggtccag   86220
gaggaaacag gtagaaaaac tgatagtgac agcacagagg gaaaagagct atgaaagagc   86280
tggcacaggg acagagaagt ccgggggatc atgtatcggc gatggcttcc tggaggaggt   86340
agtgtctgag ctgagatgtg tgggaagggc agaattaact aggtgaggag gtggaggaag   86400
agagacccgt ggagagggag cagcctgtgc agggttctga acgcacaggg ttgccaggac   86460
ctgaggcaaa atgaggaagg tggtgtcctc ctgtcctggg ctgtggtcag aggggattga   86520
tgagcacggt gtcttttgg gagaggatgg gagtcatttt accgacgag aaactgaggc   86580 caagagaaag gaagagcctt tcctgggctt caggcagagc tgagactaga aactgaggct   86640
caggatactt agcctggagg atgtgtgtgt gtatttgtac gtgtgtttgt gtgtgttagg   86700
tcatagggct gtacctcctc tgtccctcca cagtctggag tctgggaggg ggttgtattt   86760
aggaccctga ctccatggag gggtcctggg gcagaagtgg gggtactgaa ctgtgttgca   86820
gcatcaggga cacccacct ctgtgagctg gtgctgaagg gcagaggcag tgagagagaa   86880
ggctgggggg aggttctggg gtgggtggga gtgatccagg cctattcctg gaagcaggca   86940
gcctcatgta ggagcgtgtg aaccggttaa ggtgtagctt tctagctgca cagcagtagg   87000
catcagtgca gtttgcaaag ggttcatctt ggctgatctg aacgtgtcag tgcagaacgc   87060
attggggcag gtgggccttg cagcctgtgg gcaactggtg gtgattgggg gagctgctga   87120
aggtgagtct ggagtgagtg ggtggccag ggttcgtggg agccacaggg caagtgtgga   87180
gcccttgggg tgggcatggc tgtggggtga gccccggcca ggctctactc agctctcccc   87240
tctccgtgct tatgcccagc cctgcctgca gtactggcca gagccaggcc ggcagcaata   87300
tggcctcatg gaggtggagt ttatgtcggg cacagctgat gaagacttag tggctcgagt   87360
cttccgggtc cagaacatct ctcggtgag tggtctgagg agcccagggg aaggaccctg   87420
ggtggtggct ggggcagctt ttaatgaccc tctgtgtcat caggggcccc tgggaccctg   87480
gtgctcatgt cctccctggc tggctgcccc tgtcccagt tgcaggaggg gcacctgctg   87540
gtgcggcact tccagttcct gcgctggtct gcataccggg acacacctga ctccaagaag   87600
```

```
gccttcttgc acctgctggc tgaggtggac aagtggcagg ccgagagtgg ggatgggcgc    87660
accatcgtgc actgcctgtg agtacctgcc ctgtgggagg gcgggtggag gggttgggga    87720
gccaggggca gaggtccagt ctgaaagggt gccagctttg gctggactgc aaagctggca    87780
ccgaaacccc tgggctctta gatggctgtg gccaggatgc tgcccaacca gccaaggctg    87840
gccctggagg aatccagtga gtttccaggc tatagactca gccctgaaca actgcccagt    87900
atcctctgtg tgatgtctga cttttgccaat ttaattagag tccttggtca gaattttttta   87960 ccccatgaga ttgtggcaca cttttatgcc aatagaattc cagtctttgt tcatgcatgc    88020
acacatgtga cttttttccat ccatccatcc atccacccat ccatccatcc atccatctgc   88080
atgccccatt cataagttca tgtattcact catgtctggg tgcagtcact cctttgctcc    88140
ccactttttc atgctttcag catttactga gcctttcgag tggcaggctg ggcctactgg    88200
aagctggtgc ggagctgagt cagtccgggt ctggccccca ggggttttgg ttctggtggg    88260
aaagacccct gagaaggggga gtgagggccg catcagtctg ccattcccca ggaggcaccc    88320
cacacgtgga gtcacaggga aggagggaga ggcacggagg ggatggagct ctgtgggagg    88380
ctgtgggttt gacttggggt ttgggtacgt ttgtgcctgt gtgcccacga tgccaggtgg    88440
tgaccagtct tctcagcatt cctgttccac cttgctctct gggtacgcgc ttgctgctcc    88500
tccgcccttc tttgtcactg tctttgtctc tccgggtgtt tctcttggag tgtgtctggc    88560 ctccttttctc tcagaatccg cagtctgttt cgccttgaga atatgtcttc tgagatgtct   88620
tagcctctga tccttcttaa cctggtcctg ctcctccctc tgggttccct agccccgccc   88680
cttacctctg ggtcctctgc cccgcccttc tgagttccct agttctgccc ctcaccttgg    88740
gctctttggc cctccttagt ttcctagccc cgcccctcac ctctggactc tttggcccct    88800
cctttctggg tttcctagct ctgcccctca tctctgggct ctttgccctc ttccttctgg    88860
gttccctagc tccgcccctc tcctctaggc tctcgggccc ctcctttctg tgttctctaa    88920
ctccgcccct cacctctggg ctctctgccc caccttcta gattccctag ctccgtccct   88980
ctcctctagg ctctctgccc ctccctcgtg gttccctggc ccttttctta ccttcaggtt    89040
ccaaggcccc gcccctcagc ttttgcatct ctcattcaga aacgggggag gacgcagcgg    89100
caccttctgc gcctgcgcca cggtcctgga gatgatccgc tgccacaact tggtggacgt    89160
tttctttgct gccaaaaccc tccggaacta caaacccaac atggtggaga ccatggtgag    89220
gggctgtgtc ccgtgcccag ccacttccac cttcctggtc catgccaggc caggttcctt    89280
agcacccact ctcccatatc tgggcccccac cactgggcct tggttctagc cctgtggtcc    89340
taaaacatta ccccccatttc tcccttctcc ccgagggcgg gcctgggctc gggctcgtgc    89400
ttgccctctc actcccgtt ccctccccc cacaatactg gagttggggt caggctcatg    89460
attccctccc tctcttcctc tccccaggat cagtaccact tttgctacga tgtggccctg    89520
gagtacttgg aggggctgga gtcaagatag cgggccctg gcctggggca cccactgcac    89580
actcagggcc agacccacca tcctggactg gcgaggaaga tcagtgcctc ctgctctgcc    89640
caaacacact cccatggggc aagcactgga gtggatgctg ggctatcttg ctcccccttc    89700
cactgtgggc agggcctttc gcttgtccca tgggcgggtg gtgggccaag gaggagctta    89760
gcaagtctgc agcccagccc cacctccata gggtcctgca ggcctgtgct gagaggcctg    89820
gtgctgcctg gcagagtgac aaaggctcag gacggctggc tctgggggac tcaggccaag    89880 cccctttggca ccatcctggc ttttggcagg gatgagtgag gccctgcaga gagcatccca    89940
ggccaaggtt cccactcagc ctgcccctc tgcatgtggg tagaggatgt actgggactt    90000
```

| | |
|---|---|
| ggcatttagg attccatctg gcccagcccc tgaaggtcct ggggaagcag gtctcaattc | 90060 |
| tgaatagcca gtggggcaca ctgactgtcc tccccagggg aactgcagcg ccctcctccc | 90120 |
| cactgccccc tgcagcccct gagatatttt gctcactatc cctccccact tgcttccctg | 90180 |
| atatgtgctc tgagcttccc tgaaccagga tctgcctatt actgctgtgc cccatggggg | 90240 |
| gctccttccc tgcctgaccc actgttgcag aatgaagtca cctcgccccc ctcttccttt | 90300 |
| aatcttcagg cctcactggc ctgtcctgct cagcttgggc cagtgacaat ctgcaaggct | 90360 |
| gaacaacagc ccctggggtt gaggcccctg tggctcctgg tcaggctgcc cgttgtgggg | 90420 |
| aggggcagtg ttagagcagg gctggtcata ccctctggag ttcagaggaa gaggtaggac | 90480 |
| cagtgctttt ttgtttcttt tgttattttt ggttgggtgg gtgggaaggt ctctttaaaa | 90540 |
| tggggcaggc cacaccccca ttccgtgcct caatttcccc atctgtaaac tgtagatatg | 90600 |
| actactgacc tacctcgcag ggggctgtgg ggaggcataa gctgatgttt gtaaagcgct | 90660 |
| ttgtaaataa acgtgctctc tgaatgccac agagcagccc tgtgtgtgtc tcaccagcct | 90720 |
| gacggggcct gctcacctgc ccccagcctc cagtgcagtg ggagggccct ggagaagcct | 90780 |
| gggttctgat ctggtcctgg tttttccatt cgtaaaatgg tgggagtgtg gaccaggaca | 90840 |
| tcactcaggg tccttccact ttcagagttg gttccaaggg accctggcca ttgctgtccc | 90900 |
| catccaggcc tctgaagcag ttcctcaggt agggtatatc aactcgagat ccctgagggc | 90960 |
| cacagagctg cctctcactc cactgggggc cctggatcag gttcagctct ttctggggca | 91020 |
| gcatgggagg ctcaggcttt ggtgtcaggc agatgggccc agcagctgcg agaccctggg | 91080 |
| caagttagt | 91089 |

<210> SEQ ID NO 5
<211> LENGTH: 5732
<212> TYPE: DNA
<213> ORGANISM: M. Musculus

<400> SEQUENCE: 5

| | |
|---|---|
| gttgactact cagctgccag aacatccaat ctggctcctg caactttaga ccaacatatt | 60 |
| gtgtttgatc ttctcctgaa caacttggga gatacgtctg atcttcagct tggtacatac | 120 |
| agttgcgcag tgaatggcac ttacgtgttc attgtgcaca tgctaaagct ggcatgatta | 180 |
| atgttcgact gctatgtcaa cctgattaac aatgaggatg tcttggtgtc agctatgcca | 240 |
| acgatggtgc tccagaccgg cgccagtccc gctccgcgcg gcactgtcca ctacggctcc | 300 |
| cgctcgcctt gggctcccgg tcgggctccg gaggcgtcgc ctcccagct gcgggtctcc | 360 |
| aggacctagg cggcggccat ggcccgggct caggctctgg tcctggcgct caccttccag | 420 |
| ttctgcgcgc tgagaccga gactcccgca gctggctgca ccttcgagga ggcgagtgac | 480 |
| ccggtcgtgc cctgcgagtt cagccaggct cagtatgacg acttccaatg ggagcaagtg | 540 |
| cggatccacc ccggcacccg gacccctgaa gacctgcccc atggtgccta cttgatggtc | 600 |
| aatgcttctc agcataccc aggtcagagg gcccacatca tcttccagac cctgagcgag | 660 |
| aacgacaccc attgtgtgca gttcagctac ttcctgtaca gcagggatgg gcacagccca | 720 |
| ggcacccctgg gggtctacgt gcgcgtgaat gggggccctc tgggcagtgc cgtgtggaat | 780 |
| atgaccggat cccacggccg tcagtggcac caggctgagc tggctgtcag caccttctgg | 840 |
| cccaatgagt ttcaggtgct gtttgaggcc ctcatctccc cagaccacaa gggctacata | 900 |
| ggcttagacg acatcttgct cttcagctat ccctgcgcaa aggcccctca cttctcccgc | 960 |
| cttggggacg tggaggtcaa tgcaggccag aacgcatcct tccaatgcat ggcagcaggc | 1020 |

-continued

```
agagccgcag aggcagaaca cttcttcctg cagcgtcaga gtggagtgct ggtgcctgcg    1080
gccggggtgc ggcacatcag tcaccgtcgc ttcctggcca cttttccgct ggcctcggta    1140
ggccgctcag agcaggatct gtaccgttgc gtgtcccagg cccgcgtgg tgctggcgtc     1200
tccaactttg cagagctcat cgtcaaagag cctcccaccc ccatcgcgcc cccacagctg    1260
ctgcgtgcag gccccaccta cctcattatc cagctcaaca ccaactccat cattggcgac    1320
gggccgatcg tgcgcaagga gatcgagtac cgcatggcac ggggcccgtg ggccgaggtg    1380
cacgctgtca acctgcagac ctacaagctg tggcatctgg acccagacac tgagtatgaa    1440
atcagcgtgc tgctcacacg cccgggagat ggaggcacag gccgccctgg gccaccactg    1500
atcagccgga ccaagtgcgc agagcccacg agggccccca aaggtctggc ttttgctgag    1560
atccaggctc gccagctgac cctgcagtgg gagcccctgg gctataatgt cacacgttgt    1620
cataccctacg ctgtgtccct ttgctatcgc tacaccctgg gcggcagcca caaccagacc    1680
atccgggagt gtgtgaagat ggagcggggt gccagccgct acaccatcaa gaatctgctg    1740
ccattcagaa acatccacgt gcgtctgatt ctcacaaacc ctgaggggcg caaggagggc    1800
aaggaggtca ccttccagac agatgaagat gtgcctggtg ggattgcagc tgagtccta     1860
accttcactc cactggagga catgatcttt ctcaagtggg aggagcccca ggagcccaat    1920
ggcctcatca ctcagtatga gatcagctac caaagcattg agtcctcaga cccagcagtg    1980
aacgtgcccg gcccgagacg caccatctcc aaactccgga atgagactta ccacgtcttc    2040
tccaacctgc atcccggcac cacgtatctg ttctccgtgc gtgctcggac gagcaagggc    2100
ttcggccagg cggctctcac tgagataacc accaacatct cagctcccag ctttgattat    2160
gccgacatgc cgtcacccct gggcgagtcc gagaacacca tcactgtgct gttgaggccg    2220
gcccagggcc gaggagcccc catcagcgtc taccaggtgg ttgtggagga agagcggcca    2280
cggcgcttgc ggcgggagcc cggagctcag gactgcttct cggtacctct gacctttgag    2340
acggccctgg ctcgcggcct ggtgcactac tttgggctg aactggctgc cagcagcctg     2400
cttgaggcca tgcccttcac cgtgggtgac aaccagacct atcgtggctt ctggaaccca    2460
ccgcttgagc ccagaaaggc ctatctcatc tatttccagg cagcaagcca cctgaaaggg    2520
gaaacccgac tgaactgcat ccgaattgcc aggaaagctg cgtgcaagga gagcaagcga    2580
cccctcgaag tgtcccagag atcggaggag atggggctca tcctgggcat ctgtgcaggt    2640
ggtcttgccg tcctcattct cctcctgggg gccatcattg tcatcatccg caaagggaag    2700
ccagtgaaca tgacgaaagc cacggtcaac taccgccagg agaagactca catgatgagt    2760
gccgtggacc gcagcttcac agatcagagt actctgcagg aggatgagcg gttgggtctg    2820
tcctttatgg atgctcctgg ctatagtcct cgtggagacc agcgaagcgg tggtgtcacc    2880
gaggccagca gcctcctggg gggttctcca aggcgcccat gcggccggaa gggttctccg    2940
tatcataccg ggcagctcca ccctgcagtc cgagtggctg accttctaca gcacatcaac    3000
cagatgaaga cagccgaggg ctacggcttc aagcaggagt acgagagttt ctttgagggc    3060
tgggacgcca ccaagaagaa agacaagctc aaggcggcc gacaggagcc agtgtctgcc     3120
tatgatcgac accatgtgaa actacacccg atgctggcag accctgatgc cgactacatc    3180
tctgccaact acatagacgg ctaccacagg tcaaaccact tcatagccac tcaagggcca    3240
aagcctgaga tgatctacga tttctggcgc atggtgtggc aggaacagtg tgcgagcatc    3300
gtcatgatca ccaagctggt agaggtgggc agggtgaagt gttctcgcta ctggcctgag    3360
gactcagaca tgtatgggga catcaagatc acgctggtaa agacagagac actggctgag    3420
```

```
tatgtggtgc gcacctttgc cctggagcgg agaggttact cagcccggca tgaggtccgc    3480
cagttccatt tcacagcgtg gccagagcat ggtgtcccct accacgccac ggggctgctg    3540
gccttcatcc ggcgtgtgaa ggcttccact ccacctgatg ccgggcccat tgtcattcac    3600
tgcagtgcag gaactggccg cacaggctgc tacatcgtcc tggatgtgat gctggacatg    3660
gctgaatgtg aggggggtcgt ggacatttac aactgtgtga agaccctctg ttcccgacgg    3720
gtcaacatga tccagacgga ggaacaatat atcttcatcc acgatgcaat cttggaggcc    3780
tgcctgtgtg gggagaccac catccctgtc aacgagttca gggccaccta cagggagatg    3840
atccgcattg accctcagag caattcctcc cagcttcggg aagagttcca gacgctgaac    3900
tcggtcacgc cgccgctgga tgtggaggag tgtagcattg ccctgctgcc ccggaatcga    3960
gacaagaacc gtagcatgga tgtgctgcca ccagaccgct gcctgccctt cctcatctcc    4020
agtgatgggg accccaataa ctacatcaat gcagcactga ctgacagcta cacggagc     4080 gccgccttca tcgtgaccct gcacccgctg cagagtacca cgcccgactt ctggcggctg    4140
gtctacgact acgggtgcac ctccatcgtc atgctgaacc aacttaacca gtccaactcc    4200 gcctggcct gcttgcagta ctggccggag ccaggccgac agcagtatgg gctcatggag    4260
gtggagtttg tgtctggcac agcaaacgag gatttggtgt cccgagtgtt ccgggtgcag    4320
aactcttctc ggctgcagga gggtcacctg ctggtacggc acttccagtt tctgcgttgg    4380
tctgcttatc gggacacgcc tgactccagg aaggccttc tgcacctgtt ggctgaggtg    4440
gacaagtggc aggcagagag tggggatggg cgcaccgtgg tgcattgtct caacgggggt    4500
ggccgcagtg gcaccttctg cgcctgtgcc acggtcttgg agatgatccg ctgtcacagc    4560
ctggtggatg ttttctttgc tgccaaaaca cttcggaact acaagcccaa tatggtggag    4620
accatggatc agtatcattt ctgctacgac gtggccctgg agtacctgga ggctctggag    4680
ttgagatagc aggcgcctga cctggggcac ccagtgaaca cccagggcat ggcccatcat    4740
cccagatgag gagggcctgt ggccccaact ttgctcagcc ataattccac agggacaaca    4800
ctggaacgga cggacactgc accatcttgg tgacccccac gggaaggctg caggccaagg    4860
agaagctttg caagactgta tcagccccac ctctagaggg ccctgcagac ctgtgcagag    4920
aagctcgcct ggaccaaaat agctagtgct ggagagcaca ggccaggccc ctctgctcca    4980
tcacagtcct tggccagaaa tgaatgagtg tctgcagaga gcacccatgg tttgcaccca    5040
gtatggtcct ttctgcacgt ggtggaggct cactgggact tggcaggggc tgagtccccg    5100
agagtcctga agctgggact cttccccgtc tcgccggtgg gacccgctga gcatcctgca    5160
gctccattct ccatccccac tgcccctaca gacctggggt gctttgctcg ctttcctcct    5220
gcttctgagc ttttcctgca acaggacccg tgcctccttc ctgggctcca tccctgcctg    5280
gcccagtata tgcagaatga tatacttcag ctccttcttc ccctggcctt tgggtctcca    5340
tggttcagtc ctgctcagct tgggcctgtg acaatccaca aggctgaatc acagcccctg    5400
gggttgaggt ccctgtggct cttggtgagg ctgccactgg atcggggcag gctagaacag    5460
ggctggtgtc agctcctaga gtacagagga agaaggata cttggaatg gaggaccagt    5520 gcttttttg ttgttgttat tttgttattt ttttgatggg agggtgggaa gttctcttta    5580
taatggggta ggccacaccc ccatttcgtg cctcaatttc cccatctgta aactgtagat    5640
atgactactg acctacctca cagggggctg tggggaggtg taaggtaatg tttgtaaagc    5700
gctttgtaaa taaatgtgct ctctgaatgc ca                                 5732

<210> SEQ ID NO 6
```

```
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 6
cgtgtgtctg tgctagtccc                                              20

<210> SEQ ID NO 7
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 7
ggcaacgtga acaggtccaa                                              20

<210> SEQ ID NO 8
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 8
gcccattgct ggacatgc                                                18

<210> SEQ ID NO 9
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 9
agcccattgc tggacatgca                                              20

<210> SEQ ID NO 10
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 10
ttgtcccagt cccaggcctc                                              20

<210> SEQ ID NO 11
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 11
ctttccgttg gacccctggg                                              20

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
```
gtgcgcgcga gcccgaaatc                                               20

<210> SEQ ID NO 13
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 13
atccaagtgc tactgtagta                                               20

<210> SEQ ID NO 14
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20
<223> OTHER INFORMATION: n = A,T,C or G

<400> SEQUENCE: 14
nnnnnnnnnn nnnnnnnnnn                                               20

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
gccctccatg ctggcacagg                                               20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
agcaaaagat caatccgtta                                               20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
tacagaaggc tgggccttga                                               20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 18
atgcattctg cccccaagga                                               20

```
<210> SEQ ID NO 19
<211> LENGTH: 15
<212> TYPE: DNA
<213> ORGANISM: Artificial Sequence
<220> FEATURE:
<223> OTHER INFORMATION: Oligomeric Compound

<400> SEQUENCE: 19
agtgctgaca gccag                                                   15

<210> SEQ ID NO 20
<211> LENGTH: 15
<212> TYPE: DNA
<213> ORGANISM: Artificial Sequence
<220> FEATURE:
<223> OTHER INFORMATION: Oligomeric Compound

<400> SEQUENCE: 20
gctgacagcc agctc                                                   15

<210> SEQ ID NO 21
<211> LENGTH: 13
<212> TYPE: DNA
<213> ORGANISM: Artificial Sequence
<220> FEATURE:
<223> OTHER INFORMATION: Oligomeric Compound

<400> SEQUENCE: 21
gtgctgacag cca                                                     13

<210> SEQ ID NO 22
<211> LENGTH: 24
<212> TYPE: DNA
<213> ORGANISM: Artificial Sequence
<220> FEATURE:
<223> OTHER INFORMATION: Oligomeric Compound

<400> SEQUENCE: 22
agtgctgaca gccagctcag cctg                                         24

<210> SEQ ID NO 23
<211> LENGTH: 14
<212> TYPE: DNA
<213> ORGANISM: Artificial Sequence
<220> FEATURE:
<223> OTHER INFORMATION: Oligomeric Compound

<400> SEQUENCE: 23
gccagctcag cctg                                                    14

<210> SEQ ID NO 24
<211> LENGTH: 35
<212> TYPE: DNA
<213> ORGANISM: Artificial Sequence
<220> FEATURE:
<223> OTHER INFORMATION: Oligomeric Compound

<400> SEQUENCE: 24
agaaagtgct gacagccagc tcagcctggt gccac                             35

<210> SEQ ID NO 25
<211> LENGTH: 27
<212> TYPE: DNA
<213> ORGANISM: Artificial Sequence
<220> FEATURE:
<223> OTHER INFORMATION: Oligomeric Compound

<400> SEQUENCE: 25
```

```
ctgacagcca gctcagcctg gtgccac                                    27

<210> SEQ ID NO 26
<211> LENGTH: 23
<212> TYPE: DNA
<213> ORGANISM: Artificial Sequence
<220> FEATURE:
<223> OTHER INFORMATION: Oligomeric Compound

<400> SEQUENCE: 26
cagccagctc agcctggtgc cac                                        23

<210> SEQ ID NO 27
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 27
cagccagctc agcctgttgc                                            20

<210> SEQ ID NO 28
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 28
cagccagctc agcctggtgg                                            20

<210> SEQ ID NO 29
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 29
ttgccagctc agcctggtgc                                            20

<210> SEQ ID NO 30
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 30
caggcagctc accctggtgc                                            20

<210> SEQ ID NO 31
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 31
cagtcagcac agccttgtgc                                            20

<210> SEQ ID NO 32
<211> LENGTH: 22
<212> TYPE: DNA
<213> ORGANISM: Artificial Sequence
```

```
<220> FEATURE:
<223> OTHER INFORMATION: Primer

<400> SEQUENCE: 32
gagcctgagc gagaatgata cc                                              22

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
gggatccagt catattccac aca                                             23

<210> SEQ ID NO 34
<211> LENGTH: 21
<212> TYPE: DNA
<213> ORGANISM: Artificial Sequence
<220> FEATURE:
<223> OTHER INFORMATION: Probe

<400> SEQUENCE: 34
cgtctacgtg cgcgttaatg g                                               21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
gcccagaaag gcctatctca t                                               21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
gcaattcgga tgcagttcag t                                               21

<210> SEQ ID NO 37
<211> LENGTH: 23
<212> TYPE: DNA
<213> ORGANISM: Artificial Sequence
<220> FEATURE:
<223> OTHER INFORMATION: Probe

<400> SEQUENCE: 37
aggcagcaag ccacctgaaa ggg                                             23

<210> SEQ ID NO 38
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 38
gcacgggcca tggttggagc                                                 20
```

```
<210> SEQ ID NO 39
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 39
tcgaaggtgc agccagctgc                                          20

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 40
cctcctcgaa ggtgcagcca                                          20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
aagtagctga actgcacaca                                          20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
acaggaagta gctgaactgc                                          20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
gctgtacagg aagtagctga                                          20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
cactgacggc cgtgggatcc                                          20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
```

```
ggtgccactg acggccgtgg                                               20

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
agcctggtgc cactgacggc                                               20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
agctcagcct ggtgccactg                                               20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
cagccagctc agcctggtgc                                               20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
gctgacagcc agctcagcct                                               20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
gggcctcaaa cagcacctga                                               20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
gatgagggcc tcaaacagca                                               20

<210> SEQ ID NO 52
<211> LENGTH: 20
<212> TYPE: DNA
<213> ORGANISM: Artificial Sequence
```

```
<220> FEATURE:
<223> OTHER INFORMATION: Oligomeric Compound

<400> SEQUENCE: 52
gagttggtgt tgagctggat                                               20

<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
tgatggagtt ggtgttgagc                                               20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
gccaatgatg gagttggtgt                                               20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
cccgtcgcca atgatggagt                                               20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
acagcttgta ggtctgcagg                                               20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
tggatctcag caaaagccag                                               20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
gatggtctgg ttgtggctgc                                               20
```

```
<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
tcttgatggt gtagcggctg                                              20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
tcctccagtg gagtgaaggt                                              20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
tcatgtcctc cagtggagtg                                              20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
tggtagctga tctcatactg                                              20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
aagctgggag cagagatgtt                                              20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
gcataatcaa agctgggagc                                              20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
```
tgtcggcata atcaaagctg                                                    20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
cggcatgtcg gcataatcaa                                                    20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
ggtgacggca tgtcggcata                                                    20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
aggtctggtt gtcacccacg                                                    20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
tcctccgatc tctgggacac                                                    20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
ccatctcctc cgatctctgg                                                    20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
cctgcacaga tgcccaggat                                                    20

<210> SEQ ID NO 72
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 72
cggatgatga caatgatggc                                               20

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
ctttgcggat gatgacaatg                                               20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
gtggtctctc cctttgcgga                                               20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
ttctcctggc ggtagttgac                                               20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
gtgaagctgc ggtccacggc                                               20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
cccaggaggc tgctggcctc                                               20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
aagtggtttg acctgtggta                                               20
```

```
<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
ctatgaagtg gtttgacctg                                              20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
agtggctatg aagtggtttg                                              20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
cccttgagtg gctatgaagt                                              20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
cagcttggtg atcatgacga                                              20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
cctctccgct ccagggcaaa                                              20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
tgctctggcc acgctgtgaa                                              20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
```

```
atgggcccgg catcaggtgg                                                    20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
tgacaatggg cccggcatca                                                    20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
agcatcacat ccaggacgat                                                    20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
catgtccagc atcacatcca                                                    20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
gtctccccac acaggcaggc                                                    20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
tggtggtctc cccacacagg                                                    20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
agggatggtg gtctccccac                                                    20

<210> SEQ ID NO 92
<211> LENGTH: 20
<212> TYPE: DNA
<213> ORGANISM: Artificial Sequence
```

```
<220> FEATURE:
<223> OTHER INFORMATION: Oligomeric Compound

<400> SEQUENCE: 92
cgtgtgtagc tgtcagtcag                                                    20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
tgcagggtca cgatgaaggc                                                    20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gtagaccagc cgccagaagt                                                    20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
caggcggagt tggactggtt                                                    20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
tgccacttgt ccacctcagc                                                    20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
gttttggcag caaagaaaac                                                    20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
ggtactgatc catggtctcc                                                    20
```

```
<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
agggccccgc tatcttgact                                          20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
ggttcaggga agctcagagc                                          20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
gtatgaccag ccctgctcta                                          20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
atctacagtt tacagatggg                                          20

<210> SEQ ID NO 103
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
gtcatatcta cagtttacag                                          20

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
cagtagtcat atctacagtt                                          20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
```

```
taggtcagta gtcatatcta                                              20

<210> SEQ ID NO 106
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 106
gcacgtttat ttacaaagcg                                              20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
caccggcttc cctttgcgga                                              20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
ctggcagcgt gcaaagagag                                              20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
gtggtctctc ctggcagcgt                                              20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 110
agctacttac gggtagtagg                                              20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
atttcaaggg aatatttaca                                              20

<210> SEQ ID NO 112
<211> LENGTH: 20
<212> TYPE: DNA
<213> ORGANISM: Artificial Sequence
```

```
<220> FEATURE:
<223> OTHER INFORMATION: Oligomeric Compound

<400> SEQUENCE: 112
cctcctcagc acctgggtca                                              20

<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
cagcaatatc tcctaaagct                                              20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
ggtgcccctc ctgcaactgg                                              20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
aggtactcac aggcagtgca                                              20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
cgcaactgta tgtaccaagc                                              20

<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
atagcagtcg aacattaatc                                              20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
tcgttggcat agctgacacc                                              20
```

```
<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
gagcccgggc catggccgcc                                                  20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
tgggccggcc tcaacagcac                                                  20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
tggccgctct tcctccacaa                                                  20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
gccagggccg tctcaaaggt                                                  20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
ctcaagcagg ctgctggcag                                                  20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
tgggttccag aagccacgat                                                  20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
```
tcgcttgctc tccttgcacg                                               20

<210> SEQ ID NO 126
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 126
cttccctttg cggatgatga                                               20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
tctcgtactc ctgcttgaag                                               20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
taggcagaca ctggctcctg                                               20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
cagcgtgatc ttgatgtccc                                               20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
gtctggatca tgttgacccg                                               20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
gcgcctgcta tctcaactcc                                               20

<210> SEQ ID NO 132
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 132
cagtgtccgt ccgttccagt                                                    20

<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
tggcattcag agagcacatt                                                    20

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
ccttccctga aggttcctcc                                                    20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
tagtgcggac ctacccacga                                                    20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
```
taaagttgca ggagccagat                          20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
acaatgaaca cgtaagtgcc                          20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
gcggagcggg actggcgccg                          20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
cgggagccca aggcgagcgg                          20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
cctaggtcct ggagacccgc                          20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
gatccgcact tgctcccatt                          20

<210> SEQ ID NO 146
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 146
gatgtgggcc ctctgacctg                          20

<210> SEQ ID NO 147
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 147
gaagtagctg aactgcacac                                            20

<210> SEQ ID NO 148
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 148
aggaagtagc tgaactgcac                                            20

<210> SEQ ID NO 149
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 149
gtacaggaag tagctgaact                                            20

<210> SEQ ID NO 150
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 150
tgctgtacag gaagtagctg                                            20

<210> SEQ ID NO 151
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 151
gtgccactga cggccgtggg                                            20

<210> SEQ ID NO 152
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 152
tggtgccact gacggccgtg                                            20

<210> SEQ ID NO 153
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 153
cctggtgcca ctgacggccg                                            20
```

```
<210> SEQ ID NO 154
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 154
tcagcctggt gccactgacg                                               20

<210> SEQ ID NO 155
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 155
cagctcagcc tggtgccact                                               20

<210> SEQ ID NO 156
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 156
gtgctgacag ccagctcagc                                               20

<210> SEQ ID NO 157
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 157
ctcaaacagc acctgaaact                                               20

<210> SEQ ID NO 158
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 158
gagggcctca aacagcacct                                               20

<210> SEQ ID NO 159
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 159
atgagggcct caaacagcac                                               20

<210> SEQ ID NO 160
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 160
```
agatgagggc ctcaaacagc                                              20

<210> SEQ ID NO 161
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 161
aagcctatgt agcccttgtg                                              20

<210> SEQ ID NO 162
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 162
atagctgaag agcaagatgt                                              20

<210> SEQ ID NO 163
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 163
gacctccacg tccccaaggc                                              20

<210> SEQ ID NO 164
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 164
gcattggaag gatgcgttct                                              20

<210> SEQ ID NO 165
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 165
gaagtgttct gcctctgcgg                                              20

<210> SEQ ID NO 166
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 166
caccagcact ccactctgac                                              20

<210> SEQ ID NO 167
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 167
tgactgatgt gccgcacccc                                               20

<210> SEQ ID NO 168
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 168
aaagtggcca ggaagcgacg                                               20

<210> SEQ ID NO 169
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 169
cctgctctga gcggcctacc                                               20

<210> SEQ ID NO 170
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 170
ttggagacgc cagcaccacg                                               20

<210> SEQ ID NO 171
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 171
gggtgggagg ctctttgacg                                               20

<210> SEQ ID NO 172
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 172
gtgttgagct ggataatgag                                               20

<210> SEQ ID NO 173
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 173
tggtgttgag ctggataatg                                               20
```

```
<210> SEQ ID NO 174
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 174
tggagttggt gttgagctgg                                              20

<210> SEQ ID NO 175
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 175
gatggagttg gtgttgagct                                              20

<210> SEQ ID NO 176
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 176
atgatggagt tggtgttgag                                              20

<210> SEQ ID NO 177
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 177
cagatgccac agcttgtagg                                              20

<210> SEQ ID NO 178
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 178
agcacgctga tttcatactc                                              20

<210> SEQ ID NO 179
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 179
gtgcctccat ctcccgggcg                                              20

<210> SEQ ID NO 180
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 180
```
agcaaaagcc agacctttgg                                              20

<210> SEQ ID NO 181
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 181
tagctgatct catactgagt                                              20

<210> SEQ ID NO 182
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 182
atggtgcgtc tcgggccggg                                              20

<210> SEQ ID NO 183
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 183
gacgtggtaa gtctcattcc                                              20

<210> SEQ ID NO 184
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 184
acgtggtgcc gggatgcagg                                              20

<210> SEQ ID NO 185
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 185
tatctcagtg agagccgcct                                              20

<210> SEQ ID NO 186
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 186
aaagctggga gctgagatgt                                              20

<210> SEQ ID NO 187
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 187
gtcggcataa tcaaagctgg                                              20

<210> SEQ ID NO 188
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 188
atgtcggcat aatcaaagct                                              20

<210> SEQ ID NO 189
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 189
gcatgtcggc ataatcaaag                                              20

<210> SEQ ID NO 190
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 190
gacggcatgt cggcataatc                                              20

<210> SEQ ID NO 191
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 191
gggtgacggc atgtcggcat                                              20

<210> SEQ ID NO 192
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 192
tctcaaaggt cagaggtacc                                              20

<210> SEQ ID NO 193
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 193
gccgtctcaa aggtcagagg                                              20
```

```
<210> SEQ ID NO 194
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 194
gagccagggc cgtctcaaag                                               20

<210> SEQ ID NO 195
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 195
ccgcgagcca gggccgtctc                                               20

<210> SEQ ID NO 196
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 196
ggccgcgagc cagggccgtc                                               20

<210> SEQ ID NO 197
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 197
caggccgcga gccagggccg                                               20

<210> SEQ ID NO 198
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 198
agttcagccc caaagtagtg                                               20

<210> SEQ ID NO 199
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 199
catggcctca agcaggctgc                                               20

<210> SEQ ID NO 200
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 200
```
aggtctggtt gtcacccacg                                               20

<210> SEQ ID NO 201
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 201
ggaaatagat gagataggcc                                               20

<210> SEQ ID NO 202
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 202
ttcccctttc aggtggcttg                                               20

<210> SEQ ID NO 203
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 203
tggcaattcg gatgcagttc                                               20

<210> SEQ ID NO 204
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 204
cttgctctcc ttgcacgcag                                               20

<210> SEQ ID NO 205
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 205
tgagccccat ctcctccgat                                               20

<210> SEQ ID NO 206
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 206
gcaagaccac ctgcacagat                                               20

<210> SEQ ID NO 207
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 207
atggccccca ggaggagaat                                               20

<210> SEQ ID NO 208
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 208
actggcttcc ctttgcggat                                               20

<210> SEQ ID NO 209
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 209
ggtagttgac cgtggctttc                                               20

<210> SEQ ID NO 210
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 210
gcactcatca tgtgagtctt                                               20

<210> SEQ ID NO 211
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 211
gtactctgat ctgtgaagct                                               20

<210> SEQ ID NO 212
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 212
gacagaccca accgctcatc                                               20

<210> SEQ ID NO 213
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 213
cggtgacacc accgcttcgc                                               20
```

```
<210> SEQ ID NO 214
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 214
ttggagaacc ccccaggagg                                              20

<210> SEQ ID NO 215
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 215
atacggagaa cccttccggc                                              20

<210> SEQ ID NO 216
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 216
ggtctcccca cacaggcagg                                              20

<210> SEQ ID NO 217
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 217
aactcgttga cagggatggt                                              20

<210> SEQ ID NO 218
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 218
gatcatctcc ctgtaggtgg                                              20

<210> SEQ ID NO 219
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 219
tctggaactc ttcccgaagc                                              20

<210> SEQ ID NO 220
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 220
```
cagcagggca atgctacact                                                    20

<210> SEQ ID NO 221
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 221
gctgcattga tgtagttatt                                                    20

<210> SEQ ID NO 222
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 222
ctccggccag tactgcaagc                                                    20

<210> SEQ ID NO 223
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 223
catgagccca tactgctgtc                                                    20

<210> SEQ ID NO 224
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 224
ttgctgtgcc agacacaaac                                                    20

<210> SEQ ID NO 225
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 225
tcctgcagcc gagaagagtt                                                    20

<210> SEQ ID NO 226
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 226
cgtgtcccga taagcagacc                                                    20

<210> SEQ ID NO 227
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 227
gtgcagaaag gccttcctgg                                               20

<210> SEQ ID NO 228
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 228
tctgcacagg tctgcagggc                                               20

<210> SEQ ID NO 229
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 229
actagctatt ttggtccagg                                               20

<210> SEQ ID NO 230
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 230
ggccaaggac tgtgatggag                                               20

<210> SEQ ID NO 231
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 231
ggtgctctct gcagacactc                                               20

<210> SEQ ID NO 232
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 232
cagaaaggac catactgggt                                               20

<210> SEQ ID NO 233
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 233
ctgccaagtc ccagtgagcc                                               20
```

```
<210> SEQ ID NO 234
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 234
gcaaagcacc ccaggtctgt                                                   20

<210> SEQ ID NO 235
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 235
gcaggaaaag ctcagaagca                                                   20

<210> SEQ ID NO 236
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 236
gggatggagc ccaggaagga                                                   20

<210> SEQ ID NO 237
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 237
agctgaagta tatcattctg                                                   20

<210> SEQ ID NO 238
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 238
ccaagctgag caggactgaa                                                   20

<210> SEQ ID NO 239
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 239
cagccttgtg gattgtcaca                                                   20

<210> SEQ ID NO 240
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 240
```
ggctgtgatt cagccttgtg                                                 20

<210> SEQ ID NO 241
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 241
cagcctcacc aagagccaca                                                 20

<210> SEQ ID NO 242
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 242
ccccgatcca gtggcagcct                                                 20

<210> SEQ ID NO 243
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 243
caccagccct gttctagcct                                                 20

<210> SEQ ID NO 244
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 244
tactctagga gctgacacca                                                 20

<210> SEQ ID NO 245
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 245
gtatcccttc ttcctctgta                                                 20

<210> SEQ ID NO 246
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 246
gtcctccatt ccaaagtatc                                                 20

<210> SEQ ID NO 247
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 247
caaaaaaagc actggtcctc                                              20

<210> SEQ ID NO 248
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 248
aataacaaaa taacaacaac                                              20

<210> SEQ ID NO 249
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 249
catcaaaaaa ataacaaaat                                              20

<210> SEQ ID NO 250
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 250
aagagaactt cccaccctcc                                              20

<210> SEQ ID NO 251
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 251
ttataaagag aacttcccac                                              20

<210> SEQ ID NO 252
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 252
tcatatctac agtttacaga                                              20

<210> SEQ ID NO 253
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 253 acagcccect gtgaggtagg                                              20
```

```
<210> SEQ ID NO 254
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 254
tacaaacatt accttacacc                                               20

<210> SEQ ID NO 255
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 255
tcagagagca catttattta                                               20

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
ggcacagcaa acgaggattt                                               20

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
gcagaccaac gcagaaactg                                               20

<210> SEQ ID NO 258
<211> LENGTH: 17
<212> TYPE: DNA
<213> ORGANISM: Artificial Sequence
<220> FEATURE:
<223> OTHER INFORMATION: Probe

<400> SEQUENCE: 258
tcccgagtgt tccgggt                                                  17
```

COMPOSITIONS AND THEIR USES DIRECTED TO PTPRU

CROSS-REFERENCE TO RELATED APPLICATIONS

This application is a divisional application of and claims priority to U.S. application Ser. No. 11/915,309, with a §371 (c) date of Jun. 23, 2008, now U.S. Pat. No. 7,897,583, which is a U.S. National Stage application of PCT/US2006/020388, filed May 24, 2006, which claims the benefit of priority of U.S. Application Ser. No. 60/684,398 filed May 24, 2005, each of which is incorporated herein by reference in its entirety.

SEQUENCE LISTING

The present application is being filed along with a Sequence Listing in electronic format. The Sequence Listing is provided as a file entitled RTS0752USC1SEQ.txt, created on Jan. 11, 2011 which is 180 Kb in size. The information in the electronic format of the sequence listing is incorporated herein by reference in its entirety.

FIELD OF THE INVENTION

Disclosed herein are compounds, compositions and methods for modulating the expression of PTPRU in a cell, tissue or animal.

BACKGROUND OF THE INVENTION

Phosphorylation and dephosphorylation are ubiquitous processes within cells that greatly influence cellular phenotypes. The extent and duration of phosphorylation is regulated by the opposing action of phosphatases, which remove the phosphate moieties. Consequently, considerable attention has been devoted to the characterization of tyrosine kinases and tyrosine phosphatases and their associations with disease states (Zhang, *Crit. Rev. Biochem. Mol. Biol.*, 1998, 33, 1-52).

Protein tyrosine phosphatases are signaling molecules that regulate a variety of cellular processes, including cell growth and differentiation, cell cycle progression and growth factor signaling. A number of protein tyrosine phosphatases have been implicated as negative regulators of insulin signaling (Zhang, *Crit. Rev. Biochem. Mol. Biol.*, 1998, 33, 1-52). Characterization of the protein tyrosine phosphatase PTPRU revealed it to be a member of the type II receptor protein tyrosine phosphatase (rPTP) subfamily, which includes PTP.mu. and PTP.kappa. PTPRU contains many of the domains characteristic of this subfamily, including a transmembrane domain and two tandem intracellular protein tyrosine phosphatase domains. In addition, the presence of the extracellular immunoglobulin (Ig) domain and four tandem fibronectin-type III (FN-III) repeats, which are common to cell-adhesion receptors, suggests that PTPRU can contribute to the mechanisms of cell adhesion and homotypic cell interactions (Avraham et al., *Gene*, 1997, 204, 5-16; Crossland et al., *Biochem. J.*, 1996, 319 (Pt 1), 249-254; Thomas et al., *J. Biol. Chem.*, 1994, 269, 19953-19962; Wang et al., *Biochem. Biophys. Res. Commun.*, 1997, 231, 77-81; Wang et al., *Oncogene*, 1996, 12, 2555-2562). PRPRU also contains a MAM domain, which, along with the Ig-like domain, is required for the homophilic interactions displayed by PTP.mu. and PTP.kappa. (Avraham et al., *Gene*, 1997, 204, 5-16; Crossland et al., *Biochem. J.*, 1996, 319 (Pt 1), 249-254; Wang et al., *Biochem. Biophys. Res. Commun.*, 1997, 231, 77-81; Wang et al., *Oncogene*, 1996, 12, 2555-2562).

Owing to its simultaneous identification in several different cell types, PTPRU is known by many synonyms, including protein tyrosine phosphatase, receptor type, U, also known as PTP-RU or PTPU2; protein tyrosine phosphatase receptor omicron or PTPRO; protein tyrosine phosphatase pi; protein tyrosine phosphatase J or PTP-J; pancreatic carcinoma phosphatase 2, PCP2 or PCP-2; protein tyrosine phosphatase psi, receptor type, R-PTP-Psi, PTPPsi or pi R-PTP-Psi; glomerular epithelial protein 1 or GLEPP1; and FMI.

The expression of PTPRU is developmentally regulated. During early development expression is mainly in the brain and lung. In adults, PTPRU expression is in the kidney, lung, heart, skeletal muscle, pancreas, liver, prostate, testis, brain, bone marrow, and stem cells (Avraham et al., *Gene*, 1997, 204, 5-16; Crossland et al., *Biochem. J.*, 1996, 319 (Pt 1), 249-254; Wharram et al., *J. Clin. Invest.*, 2000, 106, 1281-1290; Beltran et al., *J. Comp. Neurol.*, 2003, 456, 384-395; Stepanek et al., *J. Cell Biol.*, 2001, 154, 867-878). PTPRU is additionally involved with megakaryopoiesis, cell adhesion and promotion of the G0/G1 cell cycle arrest in normal naïve quiescent B cells (Taniguchi et al., *Blood*, 1999, 94, 539-549; Aguiar et al., *Blood*, 1999, 94, 2403-2413; Yan et al., *Biochemistry*, 2002, 41, 15854-15860).

A number of tissue-specific forms of PTPRU have been identified. In the kidney, PTPRU is known as GLEPP1 and is highly expressed in podocytes, specialized epithelial cells that form the glomerular capillaries (Thomas et al., *J. Biol. Chem.*, 1994, 269, 19953-19962). In megakaryocytes, PTPRU is called PTPRO, alternative splicing of which yields a lymphoid tissue-specific, truncated form called PTPROt (Aguiar et al., *Blood*, 1999, 94, 2403-2413). Alternative splicing of PTPRU also yields osteoclastic protein tyrosine phosphatase or PTP-oc (Amoui et al., *J. Biol. Chem.*, 2003, 278, 44273-44280).

In addition to participation in the regulation of several essential functions, PTPRU is implicated in numerous disease conditions. Motiwala et al., have reported a correlation between PTPRU and diet dependent development of preneoplastic nodules and hepatocellular carcinoma (Motiwala et al., *Oncogene*, 2003, 22, 6319-6331). PTPRU expression was found to be altered in several cancerous cell lines (Crossland et al., *Biochem. J.*, 1996, 319 (Pt 1), 249-254; McArdle et al., *J. Invest. Dermatol.*, 2001, 117, 1255-1260; Wang et al., *Biochem. Biophys. Res. Commun.*, 1997, 231, 77-81; Wang et al., *Biochim. Biophys. Acta.*, 1999, 1450, 331-340). Furthermore, PTPRU was found to be hypermethylated in colon cancer (Mori et al., *Cancer Res.*, 2004, 64, 2434-2438).

The diverse tissue distribution and disease associations of PTPRU indicate that it can be an appropriate target for therapeutic intervention in a number of disease conditions.

Currently, there are no known therapeutic agents that effectively inhibit the synthesis and/or function of PTPRU. Consequently, there remains a long felt need for agents capable of effectively inhibiting PTPRU synthesis and/or function.

Generally, the principle behind antisense technology is that an antisense compound hybridizes to a target nucleic acid and effects the modulation of gene expression activity, or function, such as transcription or translation. The modulation of gene expression can be achieved by, for example, target RNA degradation or occupancy-based inhibition. An example of modulation of target RNA function by degradation is RNase H-based degradation of the target RNA upon hybridization with a DNA-like antisense compound. Another example of modulation of gene expression by target degradation is RNA interference (RNAi) using small interfering RNAs (siRNAs).

RNAi is a form of antisense-mediated gene silencing involving the introduction of double stranded (ds)RNA-like oligonucleotides leading to the sequence-specific reduction of targeted endogenous mRNA levels. This sequence-specificity makes antisense compounds extremely attractive as tools for target validation and gene functionalization, as well as therapeutics to selectively modulate the expression of genes involved in diseases.

SUMMARY OF THE INVENTION

Disclosed herein is the discovery PTPRU can be modulated to effect in vivo glucose levels. This newly discovered correlation between PTPRU activity and in vivo glucose levels provides a novel pathway for regulating glucose homeostasis in an animal. In one embodiment, modulators that decrease the activity of PTPRU are provided as compounds that reduce in vivo glucose levels. Preferably the PTPRU modulators are specific for PTPRU, and more preferably the modulators are antisense compounds that hybridize with a nucleic acid molecule that expresses PTPRU, thereby inhibiting expression of the nucleic acid molecule. In another embodiment, the glucose levels are blood glucose levels, which include, but are not limited to, whole blood, plasma or serum glucose levels. In a further embodiment, the in vivo blood glucose levels are reduced to treat a disease or condition associated therewith. The disease or condition can include, but is not limited to, diabetes, type II diabetes, prediabetes, obesity, metabolic syndrome or a combination thereof.

In a further aspect, PTPRU is modulated to effect the levels of HbA.sub.1c (hereinafter "HbA1c"). HbA1c is a glycosylated form of hemoglobin and is a clinical indicator of excessive blood glucose levels and diabetes. In one embodiment, modulators of PTPRU are provided as compounds that that reduce in vivo blood glucose levels and in turn reduce the levels of HbA1c. Preferably, the PTPRU modulators are specific for PTPRU, and more preferably the modulators are antisense compounds that hybridize with a nucleic acid molecule that expresses PTPRU, thereby inhibiting expression of the nucleic acid molecule.

Disclosed herein are antisense compounds targeted to and hybridizable with a nucleic acid molecule encoding PTPRU and which modulate the expression of PTPRU. In a preferred embodiment the nucleic acid molecule encoding PTPRU has a nucleotide sequence that is substantially similar to one or more of GenBank Accession Nos.: NM_005704.2, NM_133177.1, NM_133178.1 or NT_004538.15 (SEQ ID NOS: 1-4, respectively), presented in table 1, below and incorporated herein by reference. In a further aspect, the antisense compounds are targeted to and hybridizable with a region of a nucleic acid molecule encoding PTPRU. Still further, the antisense compounds are targeted to and hybridizable with a segment of a nucleic acid molecule encoding PTPRU. Still further the antisense compounds are targeted to and hybridizable with a site of a nucleic acid molecule encoding PTPRU.

Further disclosed herein are active target segments comprising segments of a nucleic acid molecule encoding PTPRU, the active target segments being accessible to antisense hybridization, and so, suitable for antisense modulation. In one embodiment, the active target segments have been discovered herein using empirical data that is presented below, wherein at least two chimeric oligonucleotides are shown to hybridize within the active target segment and reduce expression of the target nucleic acid (hereinafter, "active antisense compound"). The at least two active antisense compounds are preferably separated by about 60 nucleobases on the nucleic acid molecule encoding PTPRU. In another embodiment, antisense compounds are designed to target the active target segments and modulate expression of the nucleic acid molecule encoding PTPRU.

In one aspect there are herein provided antisense compounds comprising sequences 12 to 35 nucleotides in length comprising at least two chemical modifications selected from a modified internucleoside linkage, a modified nucleobase or a modified sugar. Provided herein are chimeric oligonucleotides comprising a deoxynucleotide mid-region flanked on each of the 5' and 3' ends by wing regions, each wing region comprising at least one high affinity nucleotide.

In one embodiment there is herein provided chimeric oligonucleotides comprising ten deoxynucleotide mid-regions flanked on each of the 5' and 3' ends with wing regions comprising five 2'-O-(2-methoxyethyl) nucleotides and wherein each internucleoside linkage of the chimeric oligonucleotide is a phosphorothioate. In another embodiment there is herein provided chimeric oligonucleotides comprising fourteen deoxynucleotide mid-regions flanked on each of the 5' and 3' ends with wing regions comprising three locked nucleic acid nucleotides and wherein each internucleoside linkage of the chimeric oligonucleotide is a phosphorothioate. In a further embodiment there are herein provided chimeric oligonucleotides comprising fourteen deoxynucleotide mid-regions flanked on each of the 5' and 3' ends by wing regions comprising two 2'-O-(2-methoxyethyl) nucleotides and wherein each internucleoside linkage of the chimeric oligonucleotide is a phosphorothioate. In a further embodiment, the antisense compounds may comprise at least one 5-methylcytosine.

Further provided herein are methods of modulating the expression of PTPRU in cells, tissues or animals comprising contacting the cells, tissues or animals with one or more of the antisense compounds. In one embodiment, the antisense compounds are contacted to the cell, tissue or animal and inhibiting the expression of PTPRU therein. The inhibition of PTPRU expression can be measured by analyzing the cells for indicators of a decrease in expression of PTPRU mRNA and/or protein by direct measurement of mRNA and/or protein levels, and/or measuring glucose levels, triglyceride levels, insulin levels, fatty acid levels, cholesterol levels, transaminase levels, electrocardiogram, glucose uptake, gluconeogenesis, insulin sensitivity and body weight In one embodiment, there are provided methods of lowering plasma glucose or plasma triglycerides using antisense compounds that inhibit PTPRU expression in cells, tissues or animals. In another embodiment, there are provided methods of improving insulin sensitivity using antisense compounds that inhibit PTPRU expression in cells, tissues or animals.

In other embodiments, the there are provided methods of ameliorating or lessening the severity of a condition in an animal comprising contacting said animal with an effective amount of an oligomeric compound that inhibits PTPRU expression in cells, tissues or animals. In an additional embodiment, the ameliorating or lessening of the severity of the condition of an animal is measured by one or more physical indicators of said condition, comprising glucose levels, triglyceride levels, insulin levels, fatty acid levels, cholesterol levels, transaminase levels, electrocardiogram, glucose uptake, gluconeogenesis, insulin sensitivity and body weight. The conditions include, but are not limited to, diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease.

Also provided is a method of use of the oligomeric compound of the instant invention for the preparation of a medicament for the prevention, amelioration, and/or treatment disease, especially a disease associated with and including at least one indicator comprising glucose levels, triglyceride levels, insulin levels, fatty acid levels, cholesterol levels, transaminase levels, electrocardiogram, glucose uptake, gluconeogenesis, insulin sensitivity and body weight.

DETAILED DESCRIPTION OF THE INVENTION

PTPRU is herein shown to effect in vivo glucose levels in mammals. This novel discovery, therefore, provides PTPRU as a novel target for modulating blood glucose levels. Provided herein are methods of modulating blood glucose levels using a modulator of PTPRU. Preferably the modulator is selective for PTPRU. Also preferably the modulator is an antisense compound that hybridizes with a nucleic acid molecule that expresses PTPRU, thereby inhibiting the expression of the nucleic acid molecule. In one aspect, the methods of modulating PTPRU are useful for treating a disease or condition associated therewith, the disease or condition including, but not being limited to, diabetes, type II diabetes, prediabetes, obesity, metabolic syndrome or a combination thereof.

Also provided herein are modulators that decrease the activity of PTPRU and in turn reduce in vivo glucose levels. Preferably the PTPRU modulators are specific for PTPRU, and more preferably the modulators are antisense compounds that hybridize with a nucleic acid molecule that expresses PTPRU, thereby inhibiting expression of the nucleic acid molecule. In another embodiment, the glucose levels are blood glucose levels, which include, but are not limited to, whole blood, plasma or serum glucose levels. In a further embodiment, the in vivo blood glucose levels are reduced to treat a disease or condition associated therewith. The disease or condition can include, but is not limited to, diabetes, type II diabetes, prediabetes, obesity, metabolic syndrome or a combination thereof.

In a further aspect, PTPRU is modulated to effect the levels of HbA.sub.1c (hereinafter "HbA1c"). HbA1c is a glycosylated form of hemoglobin and is a clinical indicator of excessive blood glucose levels and diabetes. In one embodiment, modulators of PTPRU are provided as compounds that that reduce in vivo blood glucose levels and in turn reduce the levels of HbA1c. Preferably, the PTPRU modulators are specific for PTPRU, and more preferably the modulators are antisense compounds that hybridize with a nucleic acid molecule that expresses PTPRU, thereby inhibiting expression of the nucleic acid molecule.

Moreover, PTPRU has been shown to effect triglyceride levels, insulin levels, fatty acid levels, cholesterol levels, transaminase levels, glucose uptake, gluconeogenesis and insulin sensitivity. Therefore, PTPRU is indicated in diseases and conditions related thereto and including, but not limited to, diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease. The instant invention provides antisense compounds for the prevention, amelioration, and for treatment of diseases and conditions relating to PTPRU function. As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators may be determined by subjective or objective measures which are known to those skilled in the art. As used herein, "treatment" means to administer a composition of the invention to effect an alteration or improvement of the disease or condition. Prevention, amelioration, and/or treatment may require administration of single dose or of multiple doses at regular intervals to alter the course of the condition or disease.

Disclosed herein are antisense compounds, including antisense oligonucleotides and other antisense compounds for use in modulating the expression of nucleic acid molecules encoding PTPRU. This is accomplished by providing antisense compounds that hybridize with one or more target nucleic acid molecules encoding PTPRU. As used herein, the terms "target nucleic acid" and "nucleic acid molecule encoding PTPRU" have been used for convenience to encompass RNA (including pre-mRNA and mRNA or portions thereof) transcribed from DNA encoding PTPRU, and also cDNA derived from such RNA. In a preferred embodiment, the target nucleic acid is an mRNA encoding PTPRU.

Target Nucleic Acids

"Targeting" an antisense compound to a particular target nucleic acid molecule can be a multistep process. The process usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes PTPRU and has a polynucleotide sequence that is substantially similar to one or more of SEQ ID NOS: 1-4.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Antisense compounds targeted to such variants are within the scope of the instant invention.

In accordance with the present invention are compositions and methods for modulating the expression of PTPRU. Table 1 lists the GenBank accession numbers of sequences corresponding to nucleic acid molecules encoding PTPRU (nt=nucleotide), the date the version of the sequence was entered in GenBank, and the corresponding SEQ ID NO in the instant application, when assigned, each of which is incorporated herein by reference.

TABLE 1

Gene Targets

| Species | Genbank # | Genbank Date | SEQ ID NO |
|---------|-----------|--------------|-----------|
| Human | NM_005704.2 | Mar. 26, 2002 | 1 |
| Human | NM_133177.1 | Mar. 26, 2002 | 2 |
| Human | NM_133178.1 | Mar. 26, 2002 | 3 |
| Human | nucleotides 751930 to 843018 of NT_004538.15 (replaced by | Oct. 7, 2003 | 4 |

TABLE 1-continued

Gene Targets

| Species | Genbank # | Genbank Date | SEQ ID NO |
|---|---|---|---|
| Mouse | NT_004610) U55057.1 | Nov. 1, 1996 | 5 |

Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of PTPRU. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of antisense compounds of the present invention on target nucleic acid expression can be tested in any of a variety of cell types provided that the target nucleic acid is present at measurable levels. The effect of antisense compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources, and are well known to those skilled in the art. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). Primary cells prepared by methods known in the art. Assaying Modulation of Expression Modulation of PTPRU expression can be assayed in a variety of ways known in the art. PTPRU mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by PTPRU can be quantitated in a variety of ways well known in the art, such as immunoprecipitation, Western blot analysis (immunoblotting), ELISA or fluorescence-activated cell sorting (FACS). Antibodies directed to a protein encoded by PTPRU can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997.

Active Target Segments

The locations on the target nucleic acid defined by having at least two active antisense compounds targeted thereto are referred to as "active target segments." An active target segment is defined by one of the at least two active antisense compounds hybridizing at the 5' end of the active target segment and the other hybridizing at the 3' end of the active target segment. Additional active antisense compounds may hybridize within this defined active target segment. The compounds are preferably separated by no more than about 60 nucleotides on the target sequence, more preferably no more than about 30 nucleotides on the target sequence, even more preferably the compounds are contiguous, most preferably the compounds are overlapping. There may be substantial variation in activity (e.g., as defined by percent inhibition) of the antisense compounds within an active target segment. Active antisense compounds are those that modulate the expression of their target RNA. In one of the assays provided herein, active antisense compounds inhibit expression of their target RNA at least 10%, preferably 20%. In a preferred embodiment, at least about 50%, preferably about 70% of the oligonucleotides targeted to the active target segment modulate expression of their target RNA at least 40%. In a more preferred embodiment, the level of inhibition required to define an active antisense compound is defined based on the results from the screen used to define the active target segments. One ordinarily skilled in the art will readily understand that values received from any single assay will vary in comparison to other similar assays due to assay-to-assay conditions.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural base 5-methyl cytosine and the artificial base known as a G-clamp. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid.

Those in the art understand that for an antisense compound to be active it need not be 100% complementary to the target nucleic acid site wherein it hybridizes. Often, once an antisense compound has been identified as an active antisense compound, the compounds are routinely modified to include mismatched nucleobases compared to the sequence of the target nucleic acid site. The art teaches methods for introducing mismatches into an antisense compound without substantially altering its activity. Antisense compounds may be able to tolerate up to about 20% mismatches without significant alteration of activity, particularly so when a high affinity modification accompanies the mismatches.

Identity

Antisense compounds, or a portion thereof, may have a defined percent identity to a SEQ ID NO, or a compound having a specific compound number. As used herein, a sequence is identical to the sequence disclosed herein if it has the same nucleobase pairing ability. For example, a RNA which contains uracil in place of thymidine in the disclosed sequences of the instant invention would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the invention. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the invention, the complement of an active target segment may constitute a single portion. In a preferred embodiment, the oligonucleotides of the instant invention are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA in an oocyte injection model. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358, 1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs.

Therapeutics

Modulators of PTPRU, more preferably selective modulators of PTPRU and more preferably still antisense compounds can be used to modulate the expression of PTPRU in an animal, such as a human. Modulation of PTPRU is herein disclosed as resulting in a corresponding modulation in glucose levels, therefore there are provided compositions and methods for treating conditions and disorders associated with blood glucose levels. In one non-limiting embodiment, the methods comprise the step of administering to said animal in need of therapy for a disease or condition associated with PTPRU an effective amount of an antisense compound that inhibits expression of PTPRU. A disease or condition associated with PTPRU includes, but is not limited to, diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease. The diseases or conditions are associated with clinical indicators that include, but are not limited to blood glucose levels, blood lipid levels, hepatic lipid levels, insulin levels, cholesterol levels, transaminase levels, electrocardiogram, glucose uptake, gluconeogenesis, insulin sensitivity, body weight and combinations thereof. In one embodiment, the antisense compounds of the present invention effectively inhibit the levels or function of PTPRU mRNA. Because reduction in PTPRU mRNA levels can lead to alteration in PTPRU protein products of expression as well, such resultant alterations can also be measured. Antisense compounds of the present invention that effectively inhibit the level or function of PTPRU mRNA or protein products of expression are considered an active antisense compounds. In one embodiment, the antisense compounds of the invention inhibit the expression of PTPRU causing a reduction of RNA by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of PTPRU can be measured in a bodily fluid, tissue or organ of the animal. Methods of obtaining samples for analysis, such as body fluids (e.g., blood), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the PTPRU expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; glucose levels, triglyceride levels, insulin levels, fatty acid levels, cholesterol levels, electrocardiogram, glucose uptake, gluconeogenesis, insulin sensitivity and body weight, and other markers of diabetes, type II diabetes, obesity, insulin resistance, insulin deficiency, hypercholesterolemia, hyperglycemia, hyperlipidemia, hypertriglyceridemia, hyperfattyacidemia, liver steatosis, steatohepatitis, non-alcoholic steatohepatitis, metabolic syndrome, cardiovascular disease and coronary heart disease. Additionally, the effects of treatment can be assessed using non-invasive indicators of improved disease state or condition, such as electrocardiogram, body weight, and the like.

The antisense compounds of the present invention can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are well understood by those skilled in the art. In one aspect, the compounds of the present invention inhibit the expression of PTPRU. The compounds of the invention can also be used in the manufacture of a medicament for the treatment of diseases and disorders related to PTPRU expression by restoring glucose levels, triglyceride levels, insulin levels, fatty acid levels, cholesterol levels, glucose uptake, gluconeogenesis and insulin sensitivity to non-disease state profiles. Moreover, the compounds of the invention can be used in the manufacture of a medicament for the modulation of blood glucose levels. In this aspect, the compound is preferably a modulator that is specific for PTPRU, and is more preferably an antisense compound that inhibits the expression of a nucleic acid that encodes PTPRU. Also in this aspect, the medicament is used to modulate blood glucose levels and treat diseases and conditions associated therewith. Disease and conditions associated with dysregulated blood glucose levels include, but are not limited to, diabetes, type II diabetes, prediabetes, obesity, metabolic syndrome or a combination thereof.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of PTPRU expression in the cells of bodily fluids, organs or tissues.

Kits, Research Reagents, and Diagnostics

The antisense compounds of the present invention can be utilized for diagnostics, and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the antisense compounds of the present invention, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Antisense Compounds

The term "antisense compound" refers to a polymeric structure capable of hybridizing to a region of a nucleic acid molecule. As is also used herein, the term "active antisense compound" is an antisense compound that has been determined to hybridize with the target nucleic acid and modulate its expression. Generally, antisense compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar, includes a nucleobase, modified nucleobase or a nucleobase mimetic. Preferred monomeric subunits comprise nucleosides and modified nucleosides. An antisense compound is at least partially complementary to the region of a target nucleic acid molecule to which it hybridizes and which modulates (increases or decreases) its expression. This term includes oligonucleotides, oligonucleotides, oligonucleotide analogs, oligonucleotide mimetics, antisense compounds, antisense oligomeric compounds, and chimeric combinations of these. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. In some embodiments it is desirous to take advantage of alternate antisense mechanisms (such as RNAi). Antisense compounds that use these alternate mechanisms may optionally comprise a second compound which is complementary to the antisense compound. In other words, antisense double-stranded compounds can be two strands hybridized to form double-stranded compounds or a single strand with sufficient self complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang Each strand of the siRNA duplex may be from about 12 to about 35 nucleobases. In a preferred embodiment, each strand of the siRNA duplex is about 17 to about 25 nucleobases. The two strands may be fully complementary (i.e., form a blunt ended compound), or include a 5' or 3' overhang on one or both strands. Double-stranded compounds can be made to include chemical modifications as discussed herein.

In one embodiment of the invention, the antisense compound comprises a single stranded oligonucleotide. In some embodiments of the invention the antisense compound contains chemical modifications. In a preferred embodiment, the antisense compound is a single stranded, chimeric oligonucleotide wherein the modifications of sugars, bases, and internucleoside linkages are independently selected.

The antisense compounds may comprise a length from about 12 to about 35 nucleobases (i.e. from about 12 to about 35 linked nucleosides). In other words, a single-stranded compound of the invention comprises from about 12 to about 35 nucleobases, and a double-stranded antisense compound of the invention (such as a siRNA, for example) comprises two strands, each of which is independently from about 12 to about 35 nucleobases. This includes oligonucleotides 15 to 35 and 16 to 35 nucleobases in length. Contained within the antisense compounds of the invention (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases. For convenience we describe antisense compounds, but one ordinarily skilled in the art will understand that analogues and mimetics can have a length within this same range.

Antisense compounds about 12 to 35 nucleobases in length, preferably about 15 to 35 nucleobases in length, comprising a stretch of at least eight (8), preferably at least 12, more preferably at least 15 consecutive nucleobases selected from within the active target regions are considered to be suitable antisense compounds as well.

Modifications can be made to the antisense compounds of the instant invention and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-Methoxy ethoxy (2'-MOE) sugar modifications, inverted abasic caps, deoxynucleobases, and bicyclic nucleobase analogs such as locked nucleic acids (LNA.sup.TM) and ENA.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the present invention. The terms modified nucleobase and nucleobase mimetic can overlap but generally a modified nucleobase refers to a nucleobase that is fairly similar in structure to the parent nucleobase, such as for example a 7-deaza purine or a 5-methyl cytosine, whereas a nucleobase mimetic would include more complicated structures, such as for example a tricyclic phenoxazine nucleobase mimetic. Methods for preparation of the above noted modified nucleobases are well known to those skilled in the art.

Antisense compounds may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-($CH_2$)$_2$—O-2' bridge); and substituted sugars, especially 2'-substituted sugars having a 2'-F, 2'-$OCH_2$ or a 2'-O($CH_2$)$_2$—$OCH_3$ substituent group. Sugars can also be replaced with sugar mimetic groups among others. Methods for the preparations of modified sugars are well known to those skilled in the art.

Internucleoside linking groups link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—$CH_2$-N($CH_3$)-O—$CH_2$-), thiodiester (—O—C(O)—S—), thionocarbamate (—O—C(O)(NH)—S—); siloxane (—O—Si(H)$_2$-O—); and N,N'-dimethylhydrazine (—$CH_2$-N($CH_3$)-N($CH_3$)-). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this disclosure, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

Provided are compounds having reactive phosphorus groups useful for forming internucleoside linkages including for example phosphodiester and phosphorothioate internucleoside linkages. Methods of preparation and/or purification of precursors or antisense compounds of the instant invention are not a limitation of the compositions or methods of the invention. Methods for synthesis and purification of DNA, RNA, and the antisense compounds are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound.

Chimeric antisense compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter antisense compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric antisense compounds can be further described as having a particular motif As used herein, the term "motif" refers to the orientation of modified sugar moieties and/or sugar mimetic groups in an antisense compound relative to like or differentially modified or unmodified nucleosides. As used herein, the terms "sugars", "sugar moieties" and "sugar mimetic groups" are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used herein, the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings.

As used herein, the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used herein, the term "fully modified motif" refers to an antisense compound comprising a contiguous sequence of nucleosides wherein essentially each nucleoside is a sugar modified nucleoside having uniform modification.

As used herein, the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used herein, the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. Methods of preparation of chimeric oligonucleotide compounds are well known to those skilled in the art.

As used herein, the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), .alpha. or .beta., or as (D) or (L) such as for amino acids et al. This is meant to include all such possible isomers, as well as their racemic and optically pure forms.

In one aspect, antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The compositions and methods disclosed herein not limited by the method of oligomer purification.

Salts, Prodrugs and Bioequivalents

The antisense compounds may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., phosphodiester backbone linkages) to produce the smaller active compound.

The term "pharmaceutically acceptable salts" refers to physiologically and pharmaceutically acceptable salts of the antisense compounds: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds may also be admixed, encapsulated, conjugated or otherwise associated with other molecules, molecule structures or mixtures of compounds.

The antisense compounds may also include pharmaceutical compositions and formulations. The pharmaceutical compositions of the present invention may be administered in a number of ways depending upon whether local or systemic treatment is desired and upon the area to be treated.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery).

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions provided herein can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions can contain two or more antisense compounds targeted to different regions of the same nucleic acid target. Two or more combined compounds may be used together or sequentially. Compositions of the instant invention can also be combined with other non-antisense compound therapeutic agents.

NONLIMITING DISCLOSURE AND
INCORPORATION BY REFERENCE

While certain compounds, compositions and methods have been described with specificity in accordance with certain embodiments, the following examples serve only as illustrations of the compounds and methods and are not intended to limit the claims of the invention. Each of the references, GenBank accession numbers, and the like recited in the present application is incorporated herein by reference in its entirety.

Example 1

Cell Types and Transfection Methods

Cell types—The effect of antisense compounds on target nucleic acid expression was tested in one or more of the following cell types.

A549: The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 5000 cells/well for use in oligomeric compound transfection experiments.

B16-F10: The mouse melanoma cell line B16-F10 was obtained from the American Type Culture Collection (Manassas, Va.). B16-F10 cells were routinely cultured in DMEM, high glucose (Invitrogen Life Technologies, Carlsbad, Calif.) supplemented with 10% fetal bovine serum (Invitrogen Life Technologies, Carlsbad, Calif.), Cells were routinely passaged by trypsinization and dilution when they reached approximately 90% confluence. Cells were seeded into 96-well plates (Falcon-Primaria #3872) at a density of approximately 6500 cells/well for use in oligomeric compound transfection experiments.

RAW 264.7: The mouse Abelson murine leukemia virus-induced tumor macrophage cell line is obtained from the American Type Culture Collection (ATCC) (Manassas, Va.). RAW 264.7 cells are routinely cultured in alpha-MEM (Invitrogen Corporation, Carlsbad, Calif.) supplemented with 10% fetal bovine serum (Invitrogen Corporation, Carlsbad, Calif.), penicillin 100 units per mL, and streptomycin 100 .micro.g/mL (Invitrogen Corporation, Carlsbad, Calif.). Cells are routinely passaged by trypsinization and dilution when they reach 90% confluence. Cells are seeded into 24-well plates (Falcon-353047) at a density of ~20,000 cells/cm2 for treatment with the oligomeric compounds of the invention.

For Northern blotting or other analysis, cells may be seeded onto 100 mm or other standard tissue culture plates and treated similarly, using appropriate volumes of medium and oligonucleotide.

Treatment with antisense compounds: When cells reach appropriate confluency, they are treated with 50 nM of oligonucleotide using Lipofectin™. When cells reached 65-75% confluency, they were treated with oligonucleotide. Oligonucleotide was mixed with LIPOFECTIN™ (Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 .micro.g/mL per 100 nM oligonucleotide. Final concentration of the oligonucleotide was 50 nM. This transfection mixture was incubated at room temperature for approximately 0.5 hours. For cells grown in 96-well plates, wells were washed once with 100 .micro.L OPTI-MEM™-1 and then treated with 130 .micro.L of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37.deg.C, the medium containing the transfection mixture was replaced with fresh culture medium. Cells were harvested 16-24 hours after oligonucleotide treatment.

Control Oligonucleotides

Control oligonucleotides are used to determine the optimal oligomeric compound concentration for a particular cell line. Furthermore, when antisense compounds of the invention are tested in oligomeric compound screening experiments or phenotypic assays, control oligonucleotides are tested in parallel with compounds of the invention.

The concentration of oligonucleotide used will vary from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 .micro.M to 40 .micro.M when the antisense oligonucleotide is transfected by electroporation. Representative control oligos are presented in table 17.

TABLE 17

Control oligonucleotides for cell line testing, oligomeric compound screening and phenotypic assays

| Compound # | Target Name | Species of Target | Sequence (5' to 3') | Motif | SEQ ID NO |
|---|---|---|---|---|---|
| 113131 | CD86 | Human | CGTGTGTCTGTGCTAGTCCC | 5-10-5 | 6 |
| 289865 | forkhead box O1A (rhabdomyosarcoma) | Human | GGCAACGTGAACAGGTCCAA | 5-10-5 | 7 |
| 25237 | integrin beta 3 | Human | GCCCATTGCTGGACATGC | 4-10-4 | 8 |
| 196103 | integrin beta 3 | Human | AGCCCATTGCTGGACATGCA | 5-10-5 | 9 |
| 148715 | Jagged 2 | Human; Mouse; Rat | TTGTCCCAGTCCCAGGCCTC | 5-10-5 | 10 |
| 18076 | Jun N-Terminal Kinase-1 | Human | CTTTC"CGTTGGA"C"CCCTGGG | 5-9-6 | 11 |
| 18078 | Jun N-Terminal Kinase-2 | Human | GTGCG"CG"CGAG"C"C"CGAAATC | 5-9-6 | 12 |
| 183881 | kinesin-like 1 | Human | ATCCAAGTGCTACTGTAGTA | 5-10-5 | 13 |
| 29848 | none | none | NNNNNNNNNNNNNNNNNNNN | 5-10-5 | 14 |
| 226844 | Notch (*Drosophila*) homolog 1 | Human; Mouse | GCCCTCCATGCTGGCACAGG | 5-10-5 | 15 |
| 105990 | Peroxisome proliferator-activated receptor gamma | Human | AGCAAAAGATCAATCCGTTA | 5-10-5 | 16 |
| 336806 | Raf kinase C | Human | TACAGAAGGCTGGGCCTTGA | 5-10-5 | 17 |
| 15770 | Raf kinase C | Mouse; Murine sarcoma virus; Rat | ATGCATT"CTG"C"C"C"CTAAGGA | 5-10-5 | 18 |
| 141923 | None | None | CCTTCCCTGAAGGTTCCTCC | 5-10-5 | 138 |
| 129700 | None | None | TAGTGCGGACCTACCCACGA | 5-10-5 | 139 |

Example 2

Real-time quantitative PCR analysis of PTPRU mRNA levels

Quantitation of PTPRU mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the PTPRU being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 .micro.L PCR cocktail (2.5×PCR buffer minus MgCl.sub.2, 6.6 mM MgCl.sub.2, 375 .micro.M each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 .micro.L total RNA solution (20-200 ng). The RT reaction was carried out by incubation for 30 minutes at 48.deg.C. Following a 10 minute incubation at 95.deg.0 to activate the PLATINUM® Taq, 40 cycles of a two-step PCR protocol were carried out: 95.deg.0 for 15 seconds (denaturation) followed by 60.deg.0 for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 .micro.L of RiboGreen™ working reagent (RiboGreen™ reagent diluted 1:350 in 10 mM Tris-HCl, mM EDTA, pH 7.5) was pipetted into a 96-well plate containing 30 .micro.L purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

PTPRU-specific primers and probes for use in real-time PCR

| Species | Target SEQ ID NO | Sequence Description | Sequence (5' to 3') | SEQ ID NO |
|---|---|---|---|---|
| Human | 1, 2 & 4 | Fwd Primer | GAGCCTGAGCGAGAATGATACC | 32 |
| Human | 1, 2 & 4 | Rev Primer | GGGATCCAGTCATATTCCACACA | 33 |
| Human | 1, 2 & 4 | Probe | FAM-CGTCTACGTGCGCGTTAATGG-TAMRA | 34 |
| Mouse | 5 | Fwd Primer | GCCCAGAAAGGCCTATCTCAT | 35 |
| Mouse | 5 | Rev Primer | GCAATTCGGATGCAGTTCAGT | 36 |
| Mouse | 5 | Probe | FAM-AGGCAGCAAGCCACCTGAAAGGG-TAMRA | 37 |

Example 3

Antisense Inhibition of Human PTPRU Expression by an Antisense Compounds

A series of antisense compounds was designed to target different regions of human PTPRU RNA, using published sequences or portions of published sequences as cited in Table 1. The designed antisense compounds are complementary to one or more of the target nucleic acids in Table 1. The start and stop sites on the target nucleic acids for each antisense compound are presented in Tables 3a, b and c.

TABLE 3a

SEQ ID NO 1

| Compound # | Start Site | Stop Site |
|---|---|---|
| 356182 | 128 | 147 |
| 284985 | 206 | 225 |
| 284986 | 211 | 230 |
| 284987 | 431 | 450 |
| 284988 | 436 | 455 |
| 284989 | 441 | 460 |
| 284990 | 545 | 564 |
| 284991 | 550 | 569 |
| 284992 | 555 | 574 |

TABLE 3a-continued

SEQ ID NO 1

| Compound # | Start Site | Stop Site |
|---|---|---|
| 284993 | 560 | 579 |
| 284994 | 565 | 584 |
| 284995 | 570 | 589 |
| 284996 | 610 | 629 |
| 284997 | 615 | 634 |
| 284998 | 1046 | 1065 |
| 284999 | 1051 | 1070 |
| 285000 | 1056 | 1075 |
| 285001 | 1062 | 1081 |
| 285002 | 1150 | 1169 |
| 285003 | 1304 | 1323 |
| 285004 | 1422 | 1441 |
| 285005 | 1471 | 1490 |
| 285006 | 1619 | 1638 |
| 285007 | 1624 | 1643 |
| 285008 | 1691 | 1710 |
| 356183 | 1892 | 1911 |

TABLE 3a-continued

SEQ ID NO 1

| Compound # | Start Site | Stop Site |
|---|---|---|
| 285009 | 1901 | 1920 |
| 285010 | 1906 | 1925 |
| 285011 | 1911 | 1930 |
| 285012 | 1916 | 1935 |
| 348393 | 2179 | 2198 |
| 285019 | 2348 | 2367 |
| 285020 | 2353 | 2372 |
| 285021 | 2378 | 2397 |
| 285022 | 2429 | 2448 |
| 285023 | 2434 | 2453 |
| 356184 | 2445 | 2464 |
| 285025 | 2513 | 2532 |
| 285026 | 2549 | 2568 |
| 285027 | 2669 | 2688 |
| 285030 | 2990 | 3009 |
| 285031 | 2995 | 3014 |
| 285032 | 3000 | 3019 |
| 285033 | 3006 | 3025 |
| 285034 | 3087 | 3106 |
| 285036 | 3224 | 3243 |
| 285037 | 3278 | 3297 |
| 285038 | 3359 | 3378 |
| 285039 | 3364 | 3383 |
| 285040 | 3422 | 3441 |
| 285041 | 3429 | 3448 |
| 285043 | 3566 | 3585 |

TABLE 3a-continued

| | SEQ ID NO 1 | |
|---|---|---|
| Compound # | Start Site | Stop Site |
| 285044 | 3571 | 3590 |
| 285045 | 3576 | 3595 |
| 285046 | 3845 | 3864 |
| 285047 | 3872 | 3891 |
| 285048 | 3915 | 3934 |
| 285049 | 3974 | 3993 |
| 285050 | 4220 | 4239 |
| 285051 | 4358 | 4377 |
| 356185 | 4405 | 4424 |
| 356186 | 4467 | 4486 |
| 356187 | 5114 | 5133 |
| 356188 | 5359 | 5378 |
| 285054 | 5505 | 5524 |
| 285055 | 5510 | 5529 |
| 285056 | 5515 | 5534 |
| 285057 | 5520 | 5539 |
| 356189 | 5584 | 5603 |

TABLE 3b

| | SEQ ID NO: 2 | |
|---|---|---|
| Compound # | Start Site | Stop Site |
| 356182 | 128 | 147 |
| 284985 | 206 | 225 |
| 284986 | 211 | 230 |
| 284987 | 431 | 450 |
| 284988 | 436 | 455 |
| 284989 | 441 | 460 |
| 284990 | 545 | 564 |
| 284991 | 550 | 569 |
| 284992 | 555 | 574 |
| 284993 | 560 | 579 |
| 284994 | 565 | 584 |
| 284995 | 570 | 589 |
| 284996 | 610 | 629 |
| 284997 | 615 | 634 |
| 284998 | 1046 | 1065 |
| 284999 | 1051 | 1070 |
| 285000 | 1056 | 1075 |
| 285001 | 1062 | 1081 |
| 285002 | 1150 | 1169 |
| 285003 | 1304 | 1323 |
| 285004 | 1422 | 1441 |
| 285005 | 1471 | 1490 |
| 285006 | 1619 | 1638 |
| 285007 | 1624 | 1643 |
| 285008 | 1691 | 1710 |
| 356183 | 1892 | 1911 |
| 285009 | 1901 | 1920 |
| 285010 | 1906 | 1925 |
| 285011 | 1911 | 1930 |
| 285012 | 1916 | 1935 |
| 348393 | 2179 | 2198 |
| 285019 | 2348 | 2367 |
| 285020 | 2353 | 2372 |
| 285021 | 2378 | 2397 |
| 285022 | 2429 | 2448 |
| 285023 | 2434 | 2453 |
| 356173 | 2445 | 2464 |
| 285025 | 2483 | 2502 |
| 285026 | 2519 | 2538 |
| 285027 | 2639 | 2658 |
| 285030 | 2978 | 2997 |
| 285031 | 2983 | 3002 |
| 285032 | 2988 | 3007 |
| 285033 | 2994 | 3013 |
| 285034 | 3075 | 3094 |
| 285036 | 3212 | 3231 |
| 285037 | 3266 | 3285 |

TABLE 3b-continued

| | SEQ ID NO: 2 | |
|---|---|---|
| Compound # | Start Site | Stop Site |
| 285038 | 3347 | 3366 |
| 285039 | 3352 | 3371 |
| 285040 | 3410 | 3429 |
| 285041 | 3417 | 3436 |
| 285043 | 3554 | 3573 |
| 285044 | 3559 | 3578 |
| 285045 | 3564 | 3583 |
| 285046 | 3833 | 3852 |
| 285047 | 3860 | 3879 |
| 285048 | 3903 | 3922 |
| 285049 | 3962 | 3981 |
| 285050 | 4202 | 4221 |
| 285051 | 4340 | 4359 |
| 356185 | 4387 | 4406 |
| 356186 | 4449 | 4468 |
| 356187 | 5096 | 5115 |
| 356188 | 5340 | 5359 |
| 285054 | 5486 | 5505 |
| 285055 | 5491 | 5510 |
| 285056 | 5496 | 5515 |
| 285057 | 5501 | 5520 |
| 356189 | 5565 | 5584 |

TABLE 3c

| | SEQ ID NO: 4 | |
|---|---|---|
| Compound # | Start Site | Stop Site |
| 356182 | 525 | 544 |
| 284986 | 19165 | 19184 |
| 284987 | 22483 | 22502 |
| 284988 | 22488 | 22507 |
| 284989 | 22493 | 22512 |
| 284990 | 22597 | 22616 |
| 284991 | 22602 | 22621 |
| 284992 | 22607 | 22626 |
| 284993 | 22612 | 22631 |
| 284994 | 22617 | 22636 |
| 284995 | 22622 | 22641 |
| 284997 | 23151 | 23170 |
| 284998 | 24558 | 24577 |
| 284999 | 24563 | 24582 |
| 285000 | 24568 | 24587 |
| 285001 | 24574 | 24593 |
| 285002 | 24662 | 24681 |
| 285003 | 39360 | 39379 |
| 285004 | 39478 | 39497 |
| 285005 | 39527 | 39546 |
| 285006 | 42930 | 42949 |
| 285007 | 42935 | 42954 |
| 285009 | 43927 | 43946 |
| 285010 | 43932 | 43951 |
| 285011 | 43937 | 43956 |
| 285012 | 43942 | 43961 |
| 348393 | 46739 | 46758 |
| 285019 | 48652 | 48671 |
| 285020 | 48657 | 48676 |
| 285021 | 48682 | 48701 |
| 285022 | 48733 | 48752 |
| 285023 | 48738 | 48757 |
| 356174 | 53552 | 53571 |
| 356175 | 53562 | 53581 |
| 356176 | 53592 | 53611 |
| 285025 | 55786 | 55805 |
| 285026 | 55822 | 55841 |
| 356177 | 56678 | 56697 |
| 285027 | 67770 | 67789 |
| 285030 | 74636 | 74655 |
| 285031 | 74641 | 74660 |
| 285032 | 74646 | 74665 |

TABLE 3c-continued

SEQ ID NO: 4

| Compound # | Start Site | Stop Site |
|---|---|---|
| 285034 | 75408 | 75427 |
| 285037 | 76480 | 76499 |
| 285038 | 76561 | 76580 |
| 285039 | 76566 | 76585 |
| 356178 | 76815 | 76834 |
| 356179 | 78188 | 78207 |
| 285040 | 79289 | 79308 |
| 285041 | 79296 | 79315 |
| 285043 | 79927 | 79946 |
| 285044 | 79932 | 79951 |
| 285045 | 79937 | 79956 |
| 285047 | 84592 | 84611 |
| 285048 | 84635 | 84654 |
| 285049 | 84694 | 84713 |
| 356180 | 87516 | 87535 |
| 285050 | 87619 | 87638 |
| 356181 | 87668 | 87687 |
| 285051 | 89159 | 89178 |
| 356186 | 89540 | 89559 |
| 356187 | 90187 | 90206 |
| 356188 | 90432 | 90451 |
| 285054 | 90578 | 90597 |
| 285055 | 90583 | 90602 |
| 285056 | 90588 | 90607 |
| 285057 | 90593 | 90612 |
| 356189 | 90657 | 90676 |

As stated above, antisense oligonucleotides directed to a target or more preferably to an active target segment can be from about 13 to about 80 linked nucleobases. The following Table 3d provides a non-limiting example of such antisense oligonucleotides targeting SEQ ID NO 1.

TABLE 3d

Antisense Oligonucleotides from about 13 to about 35 Nucleobases

| Sequence | Length |
|---|---|
| CAGCCAGCTCAGCCTGGTGC | 20 nucleobases (SEQ ID NO: 48) |
| AGTGCTGACAGCCAG | 15 nucleobases (SEQ ID NO: 19) |
| GCTGACAGCCAGCTC | 15 nucleobases (SEQ ID NO: 20) |
| GTGCTGACAGCCA | 13 nucleobases (SEQ ID NO: 21) |
| AGTGCTGACAGCCAGCTCAGCCTG | 24 nucleobases (SEQ ID NO: 22) |
| GCCAGCTCAGCCTG | 14 nucleobases (SEQ ID NO: 23) |
| AGAAAGTGCTGACAGCCAGCTCAGCCTGGTGCCAC | 35 nucleobases (SEQ ID NO: 24) |
| CTGACAGCCAGCTCAGCCTGGTGCCAC | 27 nucleobases (SEQ ID NO: 25) |
| CAGCCAGCTCAGCCTGGTGCCAC | 22 nucleobases (SEQ ID NO: 26) |

Antisense oligonucleotides directed to a target or more preferably to an active target segment can also contain mismatched nucleobases when compared to the target sequence. The following Table 3e provides a non-limiting example of such antisense oligonucleotides targeting nucleobases 565 to 584 of SEQ ID NO 1. Mismatched nucleobases are underlined. One ordinarily skilled in the art understands that antisense compounds can tolerate mismatches yet still retain their ability to hybridize with a target site and modulate the target nucleic acid through antisense mechanisms.

TABLE 3e

Antisense Oligonucleotides from about 1-3 Nucleobases Mismatched to the Target Sequence

| Sequence | Number of mismatches to SEQ ID NO: 1 |
|---|---|
| CAGCCAGCTCAGCCTGGTGC (SEQ ID NO: 48) | None |
| CAGCCAGCTCAGCCTGTTGC (SEQ ID NO: 27) | One mismatch |
| CAGCCAGCTCAGCCTGGTGG (SEQ ID NO: 28) | One mismatch |
| TTGCCAGCTCAGCCTGGTGC (SEQ ID NO: 29) | Two mismatches |
| CAGGCAGCTCACCCTGGTGC (SEQ ID NO: 30) | Two mismatches |
| CAGTCAGCACAGCCTTGTGC (SEQ ID NO: 31) | Three mismatches |

These antisense compounds were screened in vitro to determine the compound's ability to modulate expression of a target nucleic acid that encodes PTPRU. The compounds shown in Table 4 are all chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines.

The compounds were analyzed for their effect on gene target mRNA levels by quantitative real-time PCR as described in other examples herein, using the primer-probe set designed to hybridize to human PTPRU (Table 2). Data are averages from two experiments in which A549 cells were treated with 50 nM of the disclosed antisense compounds using LIPOFECTIN™. A reduction in expression is expressed as percent inhibition in Table 4. The control oligomeric compound used was SEQ ID NO: 12.

TABLE 4

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 356182 | 1 | 128 | GCACGGGCCATGGTTGGAGC | 53 | 38 |
| 284985 | 1 | 206 | TCGAAGGTGCAGCCAGCTGC | 62 | 39 |
| 284986 | 1 | 211 | CCTCCTCGAAGGTGCAGCCA | 81 | 40 |
| 284987 | 1 | 431 | AAGTAGCTGAACTGCACACA | 77 | 41 |
| 284988 | 1 | 436 | ACAGGAAGTAGCTGAACTGC | 81 | 42 |
| 284989 | 1 | 441 | GCTGTACAGGAAGTAGCTGA | 76 | 43 |
| 284990 | 1 | 545 | CACTGACGGCCGTGGGATCC | 62 | 44 |
| 284991 | 1 | 550 | GGTGCCACTGACGGCCGTGG | 66 | 45 |
| 284992 | 1 | 555 | AGCCTGGTGCCACTGACGGC | 73 | 46 |
| 284993 | 1 | 560 | AGCTCAGCCTGGTGCCACTG | 63 | 47 |
| 284994 | 1 | 565 | CAGCCAGCTCAGCCTGGTGC | 59 | 48 |
| 284995 | 1 | 570 | GCTGACAGCCAGCTCAGCCT | 79 | 49 |
| 284996 | 1 | 610 | GGGCCTCAAACAGCACCTGA | 77 | 50 |
| 284997 | 1 | 615 | GATGAGGGCCTCAAACAGCA | 57 | 51 |
| 284998 | 1 | 1046 | GAGTTGGTGTTGAGCTGGAT | 82 | 52 |
| 284999 | 1 | 1051 | TGATGGAGTTGGTGTTGAGC | 73 | 53 |
| 285000 | 1 | 1056 | GCCAATGATGGAGTTGGTGT | 80 | 54 |
| 285001 | 1 | 1062 | CCCGTCGCCAATGATGGAGT | 84 | 55 |
| 285002 | 1 | 1150 | ACAGCTTGTAGGTCTGCAGG | 50 | 56 |
| 285003 | 1 | 1304 | TGGATCTCAGCAAAAGCCAG | 57 | 57 |
| 285004 | 1 | 1422 | GATGGTCTGGTTGTGGCTGC | 77 | 58 |
| 285005 | 1 | 1471 | TCTTGATGGTGTAGCGGCTG | 80 | 59 |
| 285006 | 1 | 1619 | TCCTCCAGTGGAGTGAAGGT | 75 | 60 |
| 285007 | 1 | 1624 | TCATGTCCTCCAGTGGAGTG | 65 | 61 |
| 285008 | 1 | 1691 | TGGTAGCTGATCTCATACTG | 80 | 62 |
| 356183 | 1 | 1892 | AAGCTGGGAGCAGAGATGTT | 55 | 63 |
| 285009 | 1 | 1901 | GCATAATCAAAGCTGGGAGC | 80 | 64 |
| 285010 | 1 | 1906 | TGTCGGCATAATCAAAGCTG | 70 | 65 |
| 285011 | 1 | 1911 | CGGCATGTCGGCATAATCAA | 75 | 66 |
| 285012 | 1 | 1916 | GGTGACGGCATGTCGGCATA | 77 | 67 |
| 348393 | 1 | 2179 | AGGTCTGGTTGTCACCCACG | 72 | 68 |
| 285019 | 1 | 2348 | TCCTCCGATCTCTGGGACAC | 53 | 69 |
| 285020 | 1 | 2353 | CCATCTCCTCCGATCTCTGG | 74 | 70 |
| 285021 | 1 | 2378 | CCTGCACAGATGCCCAGGAT | 73 | 71 |
| 285022 | 1 | 2429 | CGGATGATGACAATGATGGC | 49 | 72 |
| 285023 | 1 | 2434 | CTTTGCGGATGATGACAATG | 54 | 73 |
| 356184 | 1 | 2445 | GTGGTCTCTCCCTTTGCGGA | 38 | 74 |

TABLE 4-continued

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 285025 | 1 | 2513 | TTCTCCTGGCGGTAGTTGAC | 40 | 75 |
| 285026 | 1 | 2549 | GTGAAGCTGCGGTCCACGGC | 76 | 76 |
| 285027 | 1 | 2669 | CCCAGGAGGCTGCTGGCCTC | 52 | 77 |
| 285030 | 1 | 2990 | AAGTGGTTTGACCTGTGGTA | 69 | 78 |
| 285031 | 1 | 2995 | CTATGAAGTGGTTTGACCTG | 34 | 79 |
| 285032 | 1 | 3000 | AGTGGCTATGAAGTGGTTTG | 76 | 80 |
| 285033 | 1 | 3006 | CCCTTGAGTGGCTATGAAGT | 61 | 81 |
| 285034 | 1 | 3087 | CAGCTTGGTGATCATGACGA | 55 | 82 |
| 285036 | 1 | 3224 | CCTCTCCGCTCCAGGGCAAA | 51 | 83 |
| 285037 | 1 | 3278 | TGCTCTGGCCACGCTGTGAA | 72 | 84 |
| 285038 | 1 | 3359 | ATGGGCCCGGCATCAGGTGG | 56 | 85 |
| 285039 | 1 | 3364 | TGACAATGGGCCCGGCATCA | 45 | 86 |
| 285040 | 1 | 3422 | AGCATCACATCCAGGACGAT | 48 | 87 |
| 285041 | 1 | 3429 | CATGTCCAGCATCACATCCA | 44 | 88 |
| 285043 | 1 | 3566 | GTCTCCCCACACAGGCAGGC | 71 | 89 |
| 285044 | 1 | 3571 | TGGTGGTCTCCCCACACAGG | 80 | 90 |
| 285045 | 1 | 3576 | AGGGATGGTGGTCTCCCCAC | 58 | 91 |
| 285046 | 1 | 3845 | CGTGTGTAGCTGTCAGTCAG | 53 | 92 |
| 285047 | 1 | 3872 | TGCAGGGTCACGATGAAGGC | 80 | 93 |
| 285048 | 1 | 3915 | GTAGACCAGCCGCCAGAAGT | 39 | 94 |
| 285049 | 1 | 3974 | CAGGCGGAGTTGGACTGGTT | 72 | 95 |
| 285050 | 1 | 4220 | TGCCACTTGTCCACCTCAGC | 56 | 96 |
| 285051 | 1 | 4358 | GTTTTGGCAGCAAAGAAAAC | 21 | 97 |
| 356185 | 1 | 4405 | GGTACTGATCCATGGTCTCC | 49 | 98 |
| 356186 | 1 | 4467 | AGGGCCCCGCTATCTTGACT | 55 | 99 |
| 356187 | 1 | 5114 | GGTTCAGGGAAGCTCAGAGC | 80 | 100 |
| 356188 | 1 | 5359 | GTATGACCAGCCCTGCTCTA | 46 | 101 |
| 285054 | 1 | 5505 | ATCTACAGTTTACAGATGGG | 51 | 102 |
| 285055 | 1 | 5510 | GTCATATCTACAGTTTACAG | 80 | 103 |
| 285056 | 1 | 5515 | CAGTAGTCATATCTACAGTT | 82 | 104 |
| 285057 | 1 | 5520 | TAGGTCAGTAGTCATATCTA | 63 | 105 |
| 356189 | 1 | 5584 | GCACGTTTATTTACAAAGCG | 85 | 106 |
| 356173 | 2 | 2445 | CACCGGCTTCCCTTTGCGGA | 56 | 107 |
| 356174 | 4 | 53552 | CTGGCAGCGTGCAAAGAGAG | 59 | 108 |
| 356175 | 4 | 53562 | GTGGTCTCTCCTGGCAGCGT | 73 | 109 |
| 356176 | 4 | 53592 | AGCTACTTACGGGTAGTAGG | 64 | 110 |
| 356177 | 4 | 56678 | ATTTCAAGGGAATATTTACA | 20 | 111 |

TABLE 4-continued

Inhibition of human PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 356178 | 4 | 76815 | CCTCCTCAGCACCTGGGTCA | 66 | 112 |
| 356179 | 4 | 78188 | CAGCAATATCTCCTAAAGCT | 55 | 113 |
| 356180 | 4 | 87516 | GGTGCCCCTCCTGCAACTGG | 67 | 114 |
| 356181 | 4 | 87668 | AGGTACTCACAGGCAGTGCA | 47 | 115 |

The screen identified active target segments within the human PTPRU mRNA sequence, specifically SEQ ID NO: 1, 2 and 4. Each active target segment was targeted by at least one active antisense oligonucleotide. These active target regions identified for SEQ ID NO: 1 include nucleotides 1046 to 1081 (Region A) with an average inhibition of 79.7%, nucleotides 5510 to 5603 (Region B) with an average inhibition of 77.3%, nucleotides 431 to 629 (Region C) with an average inhibition of 71.5%, nucleotides 431 to 589 (Region D) with an average inhibition of 70.9%, nucleotides 431 to 460 (Region E) with an average inhibition of 78.0%, nucleotides 1422 to 1710 (Region F) with an average inhibition of 75.4%, nucleotides 1422 to 1490 (Region G) with an average inhibition of 78.4%, nucleotides 206 to 230 (Region H) with an average inhibition of 71.4%, nucleotides 1619 to 1710 (Region I) with an average inhibition of 73.3% and nucleotides 1892 to 1935 (Region J) with an average inhibition of 71.4%. Each of the oligonucleotides tested within each of these regions inhibited expression of human PTPRU greater than 50% and over half of the oligonucleotides tested in this region inhibited expression by greater than 75%. Identification of these regions allows for the design of antisense oligonucleotides that modulate the expression of PTPRU.

The active target regions identified for SEQ ID NO: 2 include nucleotides 1046 to 1081 (Region AA) with an average inhibition of 79.7%, nucleotides 5491 to 5584 (Region AB) with an average inhibition of 77.3%, nucleotides 206 to 230 (Region AC) with an average inhibition of 71.4%, nucleotides 431 to 589 (Region AD) with an average inhibition of 70.8%, nucleotides 431 to 460 (Region AE) with an average inhibition of 78.0%, nucleotides 431 to 579 (Region AF) with an average inhibition of 71.3%, nucleotides 1422 to 1490 (Region AG) with an average inhibition of 78.4%, nucleotides 1619 to 1710 (Region AH) with an average inhibition of 73.3% and nucleotides 1892 to 1935 (Region AI) with an average inhibition of 71.4%.

Active target regions have also been identified for SEQ ID NO: 4. These active target regions include nucleotides 24558 to 24593 (Region BA) with an average inhibition of 79.7%, nucleotides 90583 to 90676 (Region BB) with an average inhibition of 77.3%, nucleotides 22483 to 22641 (Region BC) with an average inhibition of 70.8%, nucleotides 22483 to 22616 (Region BD) with an average inhibition of 74.1%, nucleotides 43927 to 43961 (Region BE) with an average inhibition of 75.4%, and nucleotides 53552 to 53611 (Region BF) with an average inhibition of 65.3%.

Example 4

Antisense Inhibition of Mouse PTPRU Expression by Antisense Compounds

A series of antisense compounds was designed to target different regions of mouse PTPRU, using published sequences cited in Table 1. The compounds are shown in Table 5. All compounds in Table 5 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein and using the mouse primers an probe from Table 2. Data are averages from two experiments in which B16-F10 cells were treated with 150 nM of the disclosed antisense compounds using LIPO-FECTIN™ (as described above). A reduction in expression is expressed as percent inhibition in Table 5. The control oligomeric compound used was SEQ ID NO: 12.

TABLE 5

Inhibition of mouse PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284981 | 5 | 108 | CGCAACTGTATGTACCAAGC | 12 | 116 |
| 284982 | 5 | 176 | ATAGCAGTCGAACATTAATC | 0 | 117 |
| 284983 | 5 | 225 | TCGTTGGCATAGCTGACACC | 0 | 118 |
| 284984 | 5 | 372 | GAGCCCGGGCCATGGCCGCC | 44 | 119 |
| 284985 | 5 | 448 | TCGAAGGTGCAGCCAGCTGC | 65 | 39 |
| 284986 | 5 | 453 | CCTCCTCGAAGGTGCAGCCA | 39 | 40 |

TABLE 5-continued

Inhibition of mouse PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284987 | 5 | 673 | AAGTAGCTGAACTGCACACA | 56 | 41 |
| 284988 | 5 | 678 | ACAGGAAGTAGCTGAACTGC | 100 | 42 |
| 284989 | 5 | 683 | GCTGTACAGGAAGTAGCTGA | 63 | 43 |
| 284990 | 5 | 787 | CACTGACGGCCGTGGGATCC | 60 | 44 |
| 284991 | 5 | 792 | GGTGCCACTGACGGCCGTGG | 37 | 45 |
| 284992 | 5 | 797 | AGCCTGGTGCCACTGACGGC | 79 | 46 |
| 284993 | 5 | 802 | AGCTCAGCCTGGTGCCACTG | 51 | 47 |
| 284994 | 5 | 807 | CAGCCAGCTCAGCCTGGTGC | 68 | 48 |
| 284995 | 5 | 812 | GCTGACAGCCAGCTCAGCCT | 64 | 49 |
| 284996 | 5 | 852 | GGGCCTCAAACAGCACCTGA | 74 | 50 |
| 284997 | 5 | 857 | GATGAGGGCCTCAAACAGCA | 68 | 51 |
| 284999 | 5 | 1293 | TGATGGAGTTGGTGTTGAGC | 39 | 53 |
| 285000 | 5 | 1298 | GCCAATGATGGAGTTGGTGT | 63 | 54 |
| 285001 | 5 | 1304 | CCCGTCGCCAATGATGGAGT | 64 | 55 |
| 285002 | 5 | 1392 | ACAGCTTGTAGGTCTGCAGG | 67 | 56 |
| 285003 | 5 | 1546 | TGGATCTCAGCAAAAGCCAG | 71 | 57 |
| 285004 | 5 | 1664 | GATGGTCTGGTTGTGGCTGC | 53 | 58 |
| 285005 | 5 | 1713 | TCTTGATGGTGTAGCGGCTG | 60 | 59 |
| 285006 | 5 | 1861 | TCCTCCAGTGGAGTGAAGGT | 52 | 60 |
| 285007 | 5 | 1866 | TCATGTCCTCCAGTGGAGTG | 56 | 61 |
| 285008 | 5 | 1933 | TGGTAGCTGATCTCATACTG | 62 | 62 |
| 285009 | 5 | 2143 | GCATAATCAAAGCTGGGAGC | 71 | 64 |
| 285010 | 5 | 2148 | TGTCGGCATAATCAAAGCTG | 56 | 65 |
| 285011 | 5 | 2153 | CGGCATGTCGGCATAATCAA | 75 | 66 |
| 285012 | 5 | 2158 | GGTGACGGCATGTCGGCATA | 60 | 67 |
| 285013 | 5 | 2206 | TGGGCCGGCCTCAACAGCAC | 50 | 120 |
| 285014 | 5 | 2261 | TGGCCGCTCTTCCTCCACAA | 67 | 121 |
| 285015 | 5 | 2332 | GCCAGGGCCGTCTCAAAGGT | 79 | 122 |
| 285016 | 5 | 2387 | CTCAAGCAGGCTGCTGGCAG | 60 | 123 |
| 285017 | 5 | 2441 | TGGGTTCCAGAAGCCACGAT | 50 | 124 |
| 285018 | 5 | 2561 | TCGCTTGCTCTCCTTGCACG | 69 | 125 |
| 285019 | 5 | 2590 | TCCTCCGATCTCTGGGACAC | 40 | 69 |
| 285020 | 5 | 2595 | CCATCTCCTCCGATCTCTGG | 30 | 70 |
| 285021 | 5 | 2620 | CCTGCACAGATGCCCAGGAT | 64 | 71 |
| 285022 | 5 | 2671 | CGGATGATGACAATGATGGC | 24 | 72 |
| 285023 | 5 | 2676 | CTTTGCGGATGATGACAATG | 36 | 73 |
| 285024 | 5 | 2681 | CTTCCCTTTGCGGATGATGA | 58 | 126 |

TABLE 5-continued

Inhibition of mouse PTPRU mRNA levels by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 285025 | 5 | 2725 | TTCTCCTGGCGGTAGTTGAC | 40 | 75 |
| 285026 | 5 | 2761 | GTGAAGCTGCGGTCCACGGC | 55 | 76 |
| 285027 | 5 | 2881 | CCCAGGAGGCTGCTGGCCTC | 44 | 77 |
| 285028 | 5 | 3027 | TCTCGTACTCCTGCTTGAAG | 49 | 127 |
| 285029 | 5 | 3103 | TAGGCAGACACTGGCTCCTG | 55 | 128 |
| 285030 | 5 | 3202 | AAGTGGTTTGACCTGTGGTA | 57 | 78 |
| 285031 | 5 | 3207 | CTATGAAGTGGTTTGACCTG | 33 | 79 |
| 285032 | 5 | 3212 | AGTGGCTATGAAGTGGTTTG | 42 | 80 |
| 285033 | 5 | 3218 | CCCTTGAGTGGCTATGAAGT | 38 | 81 |
| 285034 | 5 | 3299 | CAGCTTGGTGATCATGACGA | 51 | 82 |
| 285035 | 5 | 3377 | CAGCGTGATCTTGATGTCCC | 53 | 129 |
| 285036 | 5 | 3436 | CCTCTCCGCTCCAGGGCAAA | 17 | 83 |
| 285037 | 5 | 3490 | TGCTCTGGCCACGCTGTGAA | 26 | 84 |
| 285038 | 5 | 3571 | ATGGGCCCGGCATCAGGTGG | 26 | 85 |
| 285039 | 5 | 3576 | TGACAATGGGCCCGGCATCA | 54 | 86 |
| 285040 | 5 | 3634 | AGCATCACATCCAGGACGAT | 54 | 87 |
| 285041 | 5 | 3641 | CATGTCCAGCATCACATCCA | 37 | 88 |
| 285042 | 5 | 3718 | GTCTGGATCATGTTGACCCG | 38 | 130 |
| 285043 | 5 | 3778 | GTCTCCCCACACAGGCAGGC | 72 | 89 |
| 285044 | 5 | 3783 | TGGTGGTCTCCCCACACAGG | 28 | 90 |
| 285045 | 5 | 3788 | AGGGATGGTGGTCTCCCCAC | 27 | 91 |
| 285046 | 5 | 4057 | CGTGTGTAGCTGTCAGTCAG | 42 | 92 |
| 285047 | 5 | 4084 | TGCAGGGTCACGATGAAGGC | 28 | 93 |
| 285048 | 5 | 4127 | GTAGACCAGCCGCCAGAAGT | 28 | 94 |
| 285049 | 5 | 4186 | CAGGCGGAGTTGGACTGGTT | 55 | 95 |
| 285050 | 5 | 4432 | TGCCACTTGTCCACCTCAGC | 74 | 96 |
| 285051 | 5 | 4570 | GTTTTGGCAGCAAAGAAAAC | 44 | 97 |
| 285052 | 5 | 4677 | GCGCCTGCTATCTCAACTCC | 67 | 131 |
| 285053 | 5 | 4800 | CAGTGTCCGTCCGTTCCAGT | 44 | 132 |
| 285054 | 5 | 5621 | ATCTACAGTTTACAGATGGG | 48 | 102 |
| 285055 | 5 | 5626 | GTCATATCTACAGTTTACAG | 45 | 103 |
| 285056 | 5 | 5631 | CAGTAGTCATATCTACAGTT | 44 | 104 |
| 285057 | 5 | 5636 | TAGGTCAGTAGTCATATCTA | 36 | 105 |
| 285058 | 5 | 5713 | TGGCATTCAGAGAGCACATT | 33 | 133 |

Example 5

Antisense Inhibition of PTPRU by Chimeric Phosphorothioate Oligonucleotides Having 2'-MOE Wings and a Deoxy Gap

Dose Response Studies

In a further embodiment of the present invention, oligonucleotides were selected for dose-response studies. A549 cells were treated with 10, 20, 40, or 80 nM of PTPRU antisense oligonucleotides Compound #285001, Compound #285008, Compound #285056 or Compound #356189. Control oligonucleotide Compound #141923 also was included in this study. Target mRNA levels were measured as described in other examples herein. Untreated cells served as the control to which the data were normalized.

Results of these studies are shown in Table 6. Data are averages from three experiments and are expressed as percent inhibition relative to untreated control.

TABLE 6

Inhibition of PTPRU mRNA expression in A549 Cells

| Compound # | SEQ ID NO | % Inhibition Dose of oligonucleotide | | | |
|---|---|---|---|---|---|
| | | 10 nM | 20 nM | 40 nM | 80 nM |
| 285001 | 55 | 46 | 64 | 78 | 81 |
| 285008 | 62 | 38 | 56 | 62 | 70 |
| 285056 | 104 | 36 | 60 | 71 | 74 |
| 356189 | 106 | 38 | 52 | 61 | 57 |
| 141923 | 138 | 4 | 5 | 0 | 0 |

A second screen was performed to test dose response with additional PTPRU oligonucleotides. A549 cells were treated with 10, 20, 40, or 80 nM of PTPRU antisense oligonucleotides Compound #284986, Compound #284995, Compound #284998 and Compound #285000. Control oligonucleotides Compound #129700 and Compound #141923 also were included in this study. Target mRNA levels were measured as described in other examples herein. Untreated cells served as the control to which the data were normalized.

Results of these studies are shown in Table 7. Data are averages from three experiments and are expressed as percent inhibition relative to untreated control.

TABLE 7

Inhibition of PTPRU mRNA expression in A549 Cells

| Compound # | SEQ ID NO | % Inhibition Dose of oligonucleotide | | | |
|---|---|---|---|---|---|
| | | 10 nM | 20 nM | 40 nM | 80 nM |
| 284986 | 40 | 31 | 54 | 66 | 71 |
| 284995 | 49 | 46 | 55 | 69 | 82 |
| 284998 | 52 | 30 | 56 | 72 | 81 |
| 285000 | 54 | 33 | 48 | 61 | 51 |
| 141923 | 138 | 0 | 0 | 0 | 0 |
| 129700 | 139 | 0 | 0 | 0 | 0 |

As shown in Table 6 and Table 7, each of the PTPRU antisense oligonucleotides tested were effective at reducing PTPRU mRNA levels in a dose-dependent manner.

Example 6

Antisense Inhibition of Mouse PTPRU Expression by Antisense Compounds

A Second Screen of Antisense Compounds in RAW Cells

In accordance with the present invention, a second series of antisense compounds was designed to target regions of mouse PTPRU, using published sequences cited in Table 1. The compounds are shown in Table 8. All compounds in Table 8 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the following primer-probe set designed to hybridize to mouse PTPRU:

Forward primer: GGCACAGCAAACGAGGATTT (incorporated herein as SEQ ID NO: 256)

Reverse primer: GCAGACCAACGCAGAAACTG (incorporated herein as SEQ ID NO: 257)

And the PCR probe was: FAM-TCCCGAGTGTTCCGGGT-MGB (incorporated herein as SEQ ID NO: 258), where FAM is the fluorescent dye and MGB is the quencher dye. Data are averages from three experiments in which RAW 264.7 cells were treated with 100 nM of the disclosed antisense compounds using LIPOFECTIN™. A reduction in expression is expressed as percent inhibition in Table 8.

TABLE 8

Inhibition of mouse PTPRU mRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 284988 | 5 | 678 | ACAGGAAGTAGCTGAACTGC | 4 | 42 |
| 284992 | 5 | 797 | AGCCTGGTGCCACTGACGGC | 23 | 46 |
| 284998 | 5 | 1288 | GAGTTGGTGTTGAGCTGGAT | 19 | 52 |
| 285015 | 5 | 2332 | GCCAGGGCCGTCTCAAAGGT | 35 | 122 |

TABLE 8-continued

Inhibition of mouse PTPRU mRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 348312 | 5 | 29 | TAAAGTTGCAGGAGCCAGAT | 19 | 140 |
| 348314 | 5 | 136 | ACAATGAACACGTAAGTGCC | 3 | 141 |
| 348315 | 5 | 258 | GCGGAGCGGGACTGGCGCCG | 0 | 142 |
| 348316 | 5 | 300 | CGGGAGCCCAAGGCGAGCGG | 26 | 143 |
| 348317 | 5 | 351 | CCTAGGTCCTGGAGACCCGC | 8 | 144 |
| 348320 | 5 | 527 | GATCCGCACTTGCTCCCATT | 50 | 145 |
| 348321 | 5 | 620 | GATGTGGGCCCTCTGACCTG | 12 | 146 |
| 348324 | 5 | 674 | GAAGTAGCTGAACTGCACAC | 0 | 147 |
| 348325 | 5 | 676 | AGGAAGTAGCTGAACTGCAC | 0 | 148 |
| 348326 | 5 | 680 | GTACAGGAAGTAGCTGAACT | 28 | 149 |
| 348328 | 5 | 684 | TGCTGTACAGGAAGTAGCTG | 0 | 150 |
| 348329 | 5 | 791 | GTGCCACTGACGGCCGTGGG | 0 | 151 |
| 348330 | 5 | 793 | TGGTGCCACTGACGGCCGTG | 0 | 152 |
| 348331 | 5 | 795 | CCTGGTGCCACTGACGGCCG | 0 | 153 |
| 348332 | 5 | 799 | TCAGCCTGGTGCCACTGACG | 16 | 154 |
| 348334 | 5 | 803 | CAGCTCAGCCTGGTGCCACT | 15 | 155 |
| 348336 | 5 | 814 | GTGCTGACAGCCAGCTCAGC | 0 | 156 |
| 348340 | 5 | 848 | CTCAAACAGCACCTGAAACT | 20 | 157 |
| 348342 | 5 | 854 | GAGGGCCTCAAACAGCACCT | 48 | 158 |
| 348343 | 5 | 856 | ATGAGGGCCTCAAACAGCAC | 26 | 159 |
| 348344 | 5 | 858 | AGATGAGGGCCTCAAACAGC | 0 | 160 |
| 348345 | 5 | 886 | AAGCCTATGTAGCCCTTGTG | 60 | 161 |
| 348346 | 5 | 911 | ATAGCTGAAGAGCAAGATGT | 11 | 162 |
| 348347 | 5 | 959 | GACCTCCACGTCCCCAAGGC | 0 | 163 |
| 348348 | 5 | 989 | GCATTGGAAGGATGCGTTCT | 47 | 164 |
| 348349 | 5 | 1025 | GAAGTGTTCTGCCTCTGCGG | 2 | 165 |
| 348350 | 5 | 1055 | CACCAGCACTCCACTCTGAC | 1 | 166 |
| 348351 | 5 | 1084 | TGACTGATGTGCCGCACCCC | 0 | 167 |
| 348352 | 5 | 1105 | AAAGTGGCCAGGAAGCGACG | 0 | 168 |
| 348353 | 5 | 1137 | CCTGCTCTGAGCGGCCTACC | 0 | 169 |
| 348354 | 5 | 1186 | TTGGAGACGCCAGCACCACG | 7 | 170 |
| 348355 | 5 | 1221 | GGGTGGGAGGCTCTTTGACG | 0 | 171 |
| 348356 | 5 | 1282 | GTGTTGAGCTGGATAATGAG | 0 | 172 |
| 348357 | 5 | 1284 | TGGTGTTGAGCTGGATAATG | 0 | 173 |
| 348359 | 5 | 1290 | TGGAGTTGGTGTTGAGCTGG | 3 | 174 |
| 348360 | 5 | 1292 | GATGGAGTTGGTGTTGAGCT | 28 | 175 |
| 348361 | 5 | 1294 | ATGATGGAGTTGGTGTTGAG | 3 | 176 |

TABLE 8-continued

Inhibition of mouse PTPRU mRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 348362 | 5 | 1400 | CAGATGCCACAGCTTGTAGG | 30 | 177 |
| 348363 | 5 | 1432 | AGCACGCTGATTTCATACTC | 0 | 178 |
| 348364 | 5 | 1459 | GTGCCTCCATCTCCCGGGCG | 11 | 179 |
| 348366 | 5 | 1538 | AGCAAAAGCCAGACCTTTGG | 0 | 180 |
| 348367 | 5 | 1930 | TAGCTGATCTCATACTGAGT | 39 | 181 |
| 348369 | 5 | 1987 | ATGGTGCGTCTCGGGCCGGG | 0 | 182 |
| 348370 | 5 | 2018 | GACGTGGTAAGTCTCATTCC | 0 | 183 |
| 348371 | 5 | 2046 | ACGTGGTGCCGGGATGCAGG | 30 | 184 |
| 348373 | 5 | 2108 | TATCTCAGTGAGAGCCGCCT | 9 | 185 |
| 348374 | 5 | 2135 | AAAGCTGGGAGCTGAGATGT | 0 | 186 |
| 348375 | 5 | 2147 | GTCGGCATAATCAAAGCTGG | 0 | 187 |
| 348376 | 5 | 2149 | ATGTCGGCATAATCAAAGCT | 38 | 188 |
| 348377 | 5 | 2151 | GCATGTCGGCATAATCAAAG | 33 | 189 |
| 348378 | 5 | 2155 | GACGGCATGTCGGCATAATC | 6 | 190 |
| 348380 | 5 | 2159 | GGGTGACGGCATGTCGGCAT | 39 | 191 |
| 348381 | 5 | 2322 | TCTCAAAGGTCAGAGGTACC | 22 | 192 |
| 348383 | 5 | 2326 | GCCGTCTCAAAGGTCAGAGG | 28 | 193 |
| 348386 | 5 | 2334 | GAGCCAGGGCCGTCTCAAAG | 5 | 194 |
| 348388 | 5 | 2338 | CCGCGAGCCAGGGCCGTCTC | 12 | 195 |
| 348389 | 5 | 2340 | GGCCGCGAGCCAGGGCCGTC | 0 | 196 |
| 348390 | 5 | 2342 | CAGGCCGCGAGCCAGGGCCG | 6 | 197 |
| 348391 | 5 | 2365 | AGTTCAGCCCCAAAGTAGTG | 0 | 198 |
| 348392 | 5 | 2393 | CATGGCCTCAAGCAGGCTGC | 0 | 199 |
| 348393 | 5 | 2421 | AGGTCTGGTTGTCACCCACG | 0 | 200 |
| 348395 | 5 | 2478 | GGAAATAGATGAGATAGGCC | 0 | 201 |
| 348396 | 5 | 2504 | TTCCCCTTTCAGGTGGCTTG | 0 | 202 |
| 348397 | 5 | 2532 | TGGCAATTCGGATGCAGTTC | 0 | 203 |
| 348398 | 5 | 2558 | CTTGCTCTCCTTGCACGCAG | 21 | 204 |
| 348399 | 5 | 2601 | TGAGCCCCATCTCCTCCGAT | 41 | 205 |
| 348400 | 5 | 2629 | GCAAGACCACCTGCACAGAT | 42 | 206 |
| 348401 | 5 | 2656 | ATGGCCCCAGGAGGAGAAT | 19 | 207 |
| 348402 | 5 | 2686 | ACTGGCTTCCCTTTGCGGAT | 53 | 208 |
| 348403 | 5 | 2715 | GGTAGTTGACCGTGGCTTTC | 0 | 209 |
| 348404 | 5 | 2743 | GCACTCATCATGTGAGTCTT | 18 | 210 |
| 348405 | 5 | 2773 | GTACTCTGATCTGTGAAGCT | 27 | 211 |
| 348406 | 5 | 2803 | GACAGACCCAACCGCTCATC | 16 | 212 |
| 348408 | 5 | 2862 | CGGTGACACCACCGCTTCGC | 30 | 213 |

TABLE 8-continued

Inhibition of mouse PTPRU mRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
| --- | --- | --- | --- | --- | --- |
| 348409 | 5 | 2892 | TTGGAGAACCCCCCAGGAGG | 50 | 214 |
| 348410 | 5 | 2924 | ATACGGAGAACCCTTCCGGC | 0 | 215 |
| 348411 | 5 | 3779 | GGTCTCCCCACACAGGCAGG | 39 | 216 |
| 348412 | 5 | 3799 | AACTCGTTGACAGGGATGGT | 1 | 217 |
| 348413 | 5 | 3824 | GATCATCTCCCTGTAGGTGG | 23 | 218 |
| 348415 | 5 | 3873 | TCTGGAACTCTTCCCGAAGC | 16 | 219 |
| 348417 | 5 | 3929 | CAGCAGGGCAATGCTACACT | 5 | 220 |
| 348419 | 5 | 4036 | GCTGCATTGATGTAGTTATT | 0 | 221 |
| 348420 | 5 | 4211 | CTCCGGCCAGTACTGCAAGC | 0 | 222 |
| 348421 | 5 | 4238 | CATGAGCCCATACTGCTGTC | 0 | 223 |
| 348422 | 5 | 4266 | TTGCTGTGCCAGACACAAAC | 0 | 224 |
| 348424 | 5 | 4321 | TCCTGCAGCCGAGAAGAGTT | 75 | 225 |
| 348426 | 5 | 4379 | CGTGTCCCGATAAGCAGACC | 15 | 226 |
| 348427 | 5 | 4406 | GTGCAGAAAGGCCTTCCTGG | 55 | 227 |
| 348428 | 5 | 4900 | TCTGCACAGGTCTGCAGGGC | 6 | 228 |
| 348429 | 5 | 4928 | ACTAGCTATTTTGGTCCAGG | 0 | 229 |
| 348430 | 5 | 4976 | GGCCAAGGACTGTGATGGAG | 4 | 230 |
| 348431 | 5 | 5006 | GGTGCTCTCTGCAGACACTC | 19 | 231 |
| 348432 | 5 | 5036 | CAGAAAGGACCATACTGGGT | 35 | 232 |
| 348433 | 5 | 5067 | CTGCCAAGTCCCAGTGAGCC | 20 | 233 |
| 348435 | 5 | 5188 | GCAAAGCACCCCAGGTCTGT | 30 | 234 |
| 348436 | 5 | 5220 | GCAGGAAAAGCTCAGAAGCA | 0 | 235 |
| 348437 | 5 | 5255 | GGGATGGAGCCCAGGAAGGA | 13 | 236 |
| 348438 | 5 | 5293 | AGCTGAAGTATATCATTCTG | 18 | 237 |
| 348439 | 5 | 5344 | CCAAGCTGAGCAGGACTGAA | 0 | 238 |
| 348440 | 5 | 5367 | CAGCCTTGTGGATTGTCACA | 31 | 239 |
| 348441 | 5 | 5377 | GGCTGTGATTCAGCCTTGTG | 0 | 240 |
| 348442 | 5 | 5414 | CAGCCTCACCAAGAGCCACA | 0 | 241 |
| 348443 | 5 | 5428 | CCCCGATCCAGTGGCAGCCT | 32 | 242 |
| 348444 | 5 | 5449 | CACCAGCCCTGTTCTAGCCT | 29 | 243 |
| 348445 | 5 | 5464 | TACTCTAGGAGCTGACACCA | 0 | 244 |
| 348446 | 5 | 5482 | GTATCCCTTCTTCCTCTGTA | 0 | 245 |
| 348447 | 5 | 5497 | GTCCTCCATTCCAAAGTATC | 27 | 246 |
| 348448 | 5 | 5511 | CAAAAAAGCACTGGTCCTC | 27 | 247 |
| 348449 | 5 | 5530 | AATAACAAAATAACAACAAC | 3 | 248 |
| 348450 | 5 | 5539 | CATCAAAAAAATAACAAAAT | 10 | 249 |
| 348451 | 5 | 5559 | AAGAGAACTTCCCACCCTCC | 24 | 250 |

TABLE 8-continued

Inhibition of mouse PTPRU mRNA levels in RAW cells by chimeric oligonucleotides having 2'-MOE wings and deoxy gap

| Compound # | Target SEQ ID NO | Target Site | Sequence (5' to 3') | % Inhibition | SEQ ID NO |
|---|---|---|---|---|---|
| 348452 | 5 | 5564 | TTATAAAGAGAACTTCCCAC | 5 | 251 |
| 348453 | 5 | 5625 | TCATATCTACAGTTTACAGA | 0 | 252 |
| 348454 | 5 | 5652 | ACAGCCCCTGTGAGGTAGG | 17 | 253 |
| 348455 | 5 | 5677 | TACAAACATTACCTTACACC | 0 | 254 |
| 348456 | 5 | 5707 | TCAGAGAGCACATTTATTTA | 0 | 255 |

In a further embodiment of the present invention, seven PTPRU oligonucleotides were selected for dose-response studies. RAW cells were treated with 5, 10, 25, 50, 100 or 200 nM of PTPRU antisense oligonucleotides Compound #348343, Compound #348345, Compound #349348, Compound #348400, Compound #348424, Compound #343427 or Compound #284996. Control oligonucleotide Compound #141923 also was included in this study. Target mRNA levels were measured as described in other examples herein. Untreated cells served as the control to which the data were normalized.

Results of these studies are shown in Table 9. Data are averages from three experiments and are expressed as percent inhibition relative to untreated control for the oligonucleotide doses shown below.

TABLE 9

% Inhibition of PTPRU mRNA expression in RAW Cells

| Compound # | SEQ ID NO | 5 nM | 10 nM | 25 nM | 50 nM | 100 nM | 200 nM |
|---|---|---|---|---|---|---|---|
| 348343 | 159 | 42 | 23 | 23 | 50 | 72 | 70 |
| 348345 | 161 | 28 | 36 | 1 | 39 | 48 | 68 |
| 348348 | 164 | 0 | 0 | 0 | 19 | 30 | 51 |
| 348400 | 206 | 0 | 0 | 23 | 45 | 59 | 73 |
| 348424 | 225 | 8 | 31 | 9 | 30 | 46 | 54 |
| 348427 | 227 | 0 | 16 | 7 | 0 | 30 | 64 |
| 284996 | 50 | 0 | 0 | 24 | 50 | 65 | 70 |
| 141923 | 138 | 31 | 44 | 47 | 10 | 17 | 3 |

As shown in Table 9, each of the PTPRU antisense oligonucleotides tested demonstrated a dose-responsive effect on PTPRU mRNA inhibition at doses of 10 or 25 nM and greater.

In a further embodiment of the present invention, four PTPRU oligonucleotides were selected for in vivo studies in lean mice. Six-week old male C57BL/6J-Lepr ob/ob +/− mice (Jackson Laboratory, Bar Harbor, Me.) were subcutaneously injected with PTPRU antisense oligonucleotide Compound #284996, Compound #349345, Compound #348424 or Compound #348427 at a dose of 50 mg/kg two times per week for two weeks (four total doses). Saline-injected animals served as controls. Each treatment group was comprised of five animals. After the treatment period, mice were sacrificed and target levels were evaluated in liver. RNA isolation and target mRNA expression level quantitation were performed using RIBOGREEN™ as described by other examples herein. Results are shown in Table 10 as percent inhibition of PTPRU mRNA as compared to saline treated control.

TABLE 10

Inhibition of PTPRU expression in liver of lean mice treated with PTPRU antisense oligonucleotide

| Treatment | SEQ ID NO | % Inhibition |
|---|---|---|
| Compound # 284996 | 50 | 63 |
| Compound # 348345 | 161 | 77 |
| Compound # 348424 | 225 | 82 |
| Compound # 348427 | 227 | 64 |

These results demonstrate that PTPRU antisense oligonucleotides effectively reduce PTPRU expression in cell culture and in vivo.

Example 7

Impaired Insulin Receptor Signaling in ob/ob and db/db Mice

Leptin is a hormone produced by fat that regulates appetite. Deficiencies in this hormone in both humans and non-human animals leads to obesity. ob/ob mice have a mutation in the leptin gene and db/db mice have a mutation in the leptin receptor gene. Both mutations result in obesity and hyperglycemia. As such, both types of mice are a useful model for the investigation of obesity and diabetes and treatments designed to treat these conditions. db/db mice, which have lower circulating levels of insulin and are more hyperglycemic than ob/ob mice, are often used as a rodent model of type 2 diabetes.

To characterize insulin receptor signaling in ob/ob and db/db mice, the activation states of selected proteins within the insulin receptor pathway were determined following insulin administration. Three of the key players in the insulin receptor signaling pathway are the insulin receptor .beta. subunit (IR-.beta.), PI3-Kinase and Akt. When activated, PI3-Kinase converts 4,5-PIP.sub.2 to 3,4,5-PIP.sub.3 and IR-.beta. and Akt are tyrosine phosphorylated.

Control, C57BL/6J-Lepr ob/ob mice (Jackson Laboratory, Bar Harbor, Me.) or C57B1/6J-Lepr db/db mice (Jackson Laboratory, Bar Harbor, Me.) were injected with 2 U/kg of insulin. After 2, 5, 15 and 30 minutes, animals were sacrificed and liver samples were harvested and processed for PI3-Kinase activity and western blot analysis according to standard procedures. Briefly, to detect PI3-Kinase activity, liver samples were homogenized and immunoprecipitated with anti-IRS-1 antibody (1.5 .micro.g/mg protein) (Upstate Cell Signaling Solutions, Charlottesville, Va.). After washing the immunecomplex pellet, the sample was incubated at 30.deg.0 for 15-30 minutes with .gamma.-.sup.32P-ATP and phosphatidyl inositol substrate. Lipid was then extracted and phosphorylated lipid (PIP.sub.) was resolved by thin-layer chromatography. Plates were exposed to film and the signal was quantitated. To detect phospho-IR-.beta., liver homogenates were immunoprecipitated with anti-phosphotyrosine antibody (4G10, 1.5 .micro.g/mg protein; Upstate Cell Signaling Solutions) and immunoprecipitated protein was subjected to western blotting using anti-IR-.beta. antibody (Santa Cruz Biotechnology, Inc., Santa Cruz, Calif.). To detect phosphorylated Akt, lysates were subjected to western blot using anti-p-Akt.sup.473antibody (Cell Signaling Technology, Beverly, Mass.).

In normal control mice, PI3-Kinase activity was detected as early as 2 minutes following insulin injection, but was greatest at 15 minutes. In both ob/ob and db/db mice, little to no PI3-Kinase activity was detected in response to insulin. Similarly, western blot analysis demonstrated that IR-.beta. and Aid phosphorylation increases in response to insulin in control mice, with a peak around 15 minutes after injection. In contrast, ob/ob and db/db mice exhibit little to IR-.beta. and Aid phosphorylation in response to insulin administration. Thus, these results demonstrate that ob/ob and db/db mice have deficiencies in insulin receptor signaling.

Example 8

Effects of Antisense Inhibition of PTPRU

In Vivo Study in ob/ob Mice

In accordance with the present invention, the antisense compounds of the invention were tested in the ob/ob model of obesity and diabetes.

Six-week old male C57BL/6J-Lepr ob/ob mice (Jackson Laboratory, Bar Harbor, Me.) were subcutaneously injected with PTPRU antisense oligonucleotide Compound #284996 (SEQ ID NO: 50) at a dose of 25 mg/kg two times per week for 4 weeks (eight total doses). Saline-injected animals served as controls. Each treatment group was comprised of six animals. After the treatment period, mice were sacrificed and target levels were evaluated in liver. RNA isolation and target mRNA expression level quantitation were performed using RIBOGREEN™ as described by other examples herein. As compared to saline-treated control animals, treatment with Compound #284996 resulted in a 60% reduction in PTPRU expression.

The effects of target inhibition on glucose metabolism were evaluated in ob/ob mice treated with PTPRU antisense oligonucleotide Compound #284996. Plasma glucose was measured prior 3 days prior to the start of treatment and at 12, 19 and 26 days following the first dose. Glucose levels were measured by routine clinical methods using a YSI glucose analyzer (YSI Scientific, Yellow Springs, Ohio). Average plasma glucose levels (in mg/dL) for each treatment group are shown in Table 11.

TABLE 11

Effect of PTPRU antisense oligonucleotide on plasma glucose levels in ob/ob mice

| Treatment | Day −3 (mg/dL) | Day 12 (mg/dL) | Day 19 (mg/dL) | Day 26 (mg/dL) |
|---|---|---|---|---|
| Saline | 375 | 420 | 432 | 427 |
| Compound # 284996 | 374 | 425 | 375 | 303 |

As shown in Table 11, treatment with PTPRU antisense oligonucleotide significantly reduces plasma glucose levels of ob/ob mice.

To assess the effects of inhibition of target mRNA on triglyceride levels, the ob/ob mice were further evaluated 3 days prior to the start of treatment and at 12, 19 and 26 days following the first dose of oligonucleotide for plasma triglycerides (TRIG). Triglycerides were measured by routine clinical analyzer instruments (e.g. Olympus Clinical Analyzer, Melville, N.Y.). Average levels of TRIG (mg/dL) measured for each treatment group are shown in Table 12.

TABLE 12

Triglyceride levels of ob/ob mice treated with PTPRU antisense oligonucleotide

| Treatment | Day −3 | Day 12 | Day 19 | Day 26 |
|---|---|---|---|---|
| Saline | 145 | 192 | 152 | 125 |
| Compound # 284996 | 125 | 140 | 114 | 117 |

As shown in Table 12, treatment with PTPRU antisense oligonucleotide resulted in a reduction in plasma triglyceride levels.

Antisense oligonucleotide-treated and saline control ob/ob mice were further evaluated for PI3-Kinase activity and IR-.beta. phosphorylation following insulin administration as described in other examples herein. As expected, in saline control ob/ob mice, PI3-Kinase activation and IR-.beta. phosphorylation were not observed in response to insulin treatment. In contrast, treatment with antisense oligonucleotide to PTPRU resulted in greater activation of PI3-Kinase and IR-.beta. phosphorylation relative to mice that did not receive insulin. Taken together, these results demonstrate that PTPRU antisense oligonucleotide treatment lowers plasma glucose and triglyceride levels of ob/ob mice and increases insulin responsiveness in these animals.

Example 9

Effects of Antisense Inhibition of PTPRU

A Second In Vivo Study in ob/ob Mice

In accordance with the present invention, a second study of PTPRU antisense inhibition was performed in ob/ob mice. Six-week old male C57BL/6J-Lepr ob/ob mice (Jackson Laboratory, Bar Harbor, Me.) were subcutaneously injected with PTPRU antisense oligonucleotide Compound #284996 (SEQ ID NO: 50) or Compound #285015 (SEQ ID NO: 122) at a dose of 25 mg/kg two times per week for 4 weeks (eight total doses). Saline-injected animals served as controls. Each treatment group was comprised of six animals. After the treatment period, mice were sacrificed and target levels were evaluated in liver. RNA isolation and target mRNA expression level quantitation were performed using RIBOGREEN™ as described by other examples herein. As compared to saline-treated control animals, treatment with Compound #284996 and Compound #285015 resulted in a 53% and 34% reduction, respectively, in PTPRU expression.

The effects of target inhibition on glucose metabolism were evaluated in ob/ob mice treated with PTPRU antisense oligonucleotides Compound #284996 and Compound #285015. Plasma glucose was measured prior to the start of treatment (Week 0) and at Week 2 and Week 4. Glucose levels were measured by routine clinical methods using a YSI glucose analyzer (YSI Scientific, Yellow Springs, Ohio). Average plasma glucose levels (in mg/dL) for each treatment group are shown in Table 13.

TABLE 13

Effect of PTPRU antisense oligonucleotide on plasma glucose levels in ob/ob mice

| Treatment | Week 0 (mg/dL) | Week 2 (mg/dL) | Week 4 (mg/dL) |
|---|---|---|---|
| Saline | 375 | 450 | 430 |
| Compound # 284996 | 359 | 306 | 239 |
| Compound # 285015 | 359 | 314 | 243 |

As shown in Table 13, treatment with PTPRU antisense oligonucleotide significantly reduces plasma glucose levels of ob/ob mice.

To assess triglyceride levels after inhibition of target mRNA, the ob/ob mice were further evaluated at the termination of treatment for plasma triglycerides (TRIG). Triglycerides were measured by routine clinical analyzer instruments (e.g. Olympus Clinical Analyzer, Melville, N.Y.). Average levels of TRIG (mg/dL) measured for each treatment group are shown in Table 14.

TABLE 14

Effects of PTPRU antisense oligonucleotide treatment on triglyceride levels in ob/ob mice

| Treatment | TRIG (mg/dL) |
|---|---|
| Saline | 218 |
| Compound # 284996 | 110 |
| Compound # 285015 | 93 |

Taken together, the results of these studies demonstrate that PTPRU antisense oligonucleotides reduce target mRNA levels in vivo and lead to a reduction in plasma glucose and triglyceride levels in ob/ob mice.

Example 10

Effects of Antisense Inhibition of PTPRU

In Vivo Study in db/db Mice

In accordance with the present invention, the antisense compounds of the invention were tested in the db/db model of obesity and diabetes. Six-week old male C57BL/6J-Lepr db/db mice (Jackson Laboratory, Bar Harbor, Me.) were subcutaneously injected with PTPRU antisense oligonucleotide Compound #284996 (SEQ ID NO: 50) or Compound #285015 (SEQ ID NO: 122) at a dose of 25 mg/kg two times per week for 4 weeks (eight total doses). Saline-injected animals served as controls. Each treatment group was comprised of six animals. After the treatment period, mice were sacrificed and target levels were evaluated in liver. RNA isolation and target mRNA expression level quantitation were performed using RIBOGREEN™ as described by other examples herein. As compared to saline-treated control animals, treatment with Compound #284996 and Compound #285015 resulted in a 45% and 31% reduction, respectively, in PTPRU expression.

The effects of target inhibition on glucose metabolism were evaluated in db/db mice treated with PTPRU antisense oligonucleotides Compound #284996 and Compound #285015. Plasma glucose was measured prior to the start of treatment (Week 0) and at Week 2 and Week 4. Glucose levels were measured by routine clinical methods using a YSI glucose analyzer (YSI Scientific, Yellow Springs, Ohio). Average plasma glucose levels (in mg/dL) for each treatment group are shown in Table 15.

TABLE 15

Effect of PTPRU antisense oligonucleotide on plasma glucose levels in db/db mice

| Treatment | Week 0 (mg/dL) | Week 2 (mg/dL) | Week 4 (mg/dL) |
|---|---|---|---|
| Saline | 382 | 479 | 545 |
| Compound # 284996 | 383 | 395 | 464 |
| Compound # 285015 | 380 | 411 | 442 |

As shown in Table 15, treatment with PTPRU antisense oligonucleotide significantly reduces plasma glucose levels of db/db mice.

To assess triglyceride levels after inhibition of target mRNA, the db/db mice were further evaluated at the termination of treatment for plasma triglycerides (TRIG). Triglycerides were measured by routine clinical analyzer instruments (e.g. Olympus Clinical Analyzer, Melville, N.Y.). Average levels of TRIG (mg/dL) measured for each treatment group are shown in Table 16.

TABLE 16

Effects of PTPRU antisense oligonucleotide treatment on triglyceride levels in db/db mice

| Treatment | TRIG (mg/dL) |
|---|---|
| Saline | 311 |
| Compound # 284996 | 200 |
| Compound # 285015 | 295 |

Taken together, the results of these studies demonstrate that PTPRU antisense oligonucleotides reduce target mRNA levels in vivo and lead to a reduction in plasma glucose and triglyceride levels in diabetic animals.

Various modifications of the disclosed compositions and methods will be apparent to those skilled in the art from the foregoing description. Such modifications are also intended to fall within the scope of the appended claims. The appended claims cover all such equivalent variations as fall within the true spirit and scope of the invention. Each of the patents, applications, printed publications, and other published documents mentioned or referred to in this specification are herein incorporated by reference in their entirety.

What is claimed is:

1. A compound comprising a modified oligonucleotide consisting of 15-35 linked nucleosides and having a nucleobase sequence that is at least 90% complementary to SEQ ID NO: 1 as measured over the entirety of the oligonucleotide and wherein the oligonucleotide inhibits the expression of PTPRU.

2. The compound of claim 1 wherein the oligonucleotide has a nucleobase sequence comprising at least 12 contiguous nucleobases complementary to an active target segment of SEQ ID NO:1 selected from the group consisting of Region A, Region B, Region C, Region D, Region E, Region F, Region G, Region H, Region I and Region J.

3. The compound of claim 2, wherein the oligonucleotide has a nucleobase sequence comprising at least 20 contiguous nucleobases complementary to an active target segment of SEQ ID NO:1 selected from the group consisting of Region A, Region B, Region C, Region D, Region E, Region F, Region G, Region H, Region I and Region J.

4. The compound of claim 2, wherein the active target segment is selected from the group consisting of Region C, Region F, and Region G.

5. The compound of claim 2, wherein the active target segment is Region C.

6. The compound of claim 1, wherein the oligonucleotide has a nucleobase sequence that is at least 95% complementary to SEQ ID NO: 1 as measured over the entirety of the oligonucleotide.

7. The compound of claim 1, wherein the oligonucleotide has a nucleobase sequence that is 100% complementary to SEQ ID NO: 1 as measured over the entirety of the oligonucleotide.

8. The compound of claim 1, wherein the oligonucleotide consists of 15 to 30 linked nucleosides.

9. The compound of claim 1, wherein the oligonucleotide consists of 18 to 22 linked nucleosides.

10. The compound of claim 1, wherein the modified oligonucleotide consists of 20 linked nucleosides.

11. The compound of claim 1, wherein at least one internucleoside linkage is a modified internucleoside linkage.

12. The compound of claim 11, wherein each internucleoside linkage is a phosphorothioate internucleoside linkage.

13. The compound of claim 1, wherein at least one nucleoside comprises a modified sugar.

14. The compound of claim 13, wherein at least one modified sugar is a bicyclic sugar.

15. The compound of claim 13, wherein at least one modified sugar comprises a 2'-O-methoxyethyl or a 4'-$(CH_2)_n$—O-2' bridge, wherein n is 1 or 2.

16. The compound of claim 1, wherein at least one nucleoside comprises a modified nucleobase.

17. The compound of claim 16, wherein the modified nucleobase is a 5-methylcytosine.

18. The compound of claim 1, wherein the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

19. The compound of claim 1, wherein the modified oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each cytosine in said modified oligonucleotide is a 5-methylcytosine, and wherein each internucleoside linkage of said modified oligonucleotide is a phosphorothioate linkage.

20. The compound of claim 19, wherein the modified oligonucleotide consists of 20 linked nucleosides.

21. A pharmaceutical composition comprising the compound of claim 1 and a pharmaceutically acceptable penetration enhancer, carrier, or diluent.

22. The composition of claim 21, wherein the modified oligonucleotide consists of 20 linked nucleosides.

\* \* \* \* \*